(12) United States Patent
Peytavi et al.

(10) Patent No.: US 10,427,158 B2
(45) Date of Patent: Oct. 1, 2019

(54) FLUIDIC CENTRIPETAL DEVICE

(71) Applicants: UNIVERSITÉ LAVAL, Québec (CA); GENEPOC INC., Québec (CA)

(72) Inventors: Régis Peytavi, Cabestany (FR); Sébastien Chapdelaine, Saint-Nicolas (CA)

(73) Assignees: UNIVERSITÉ LAVAL, Québec (CA); Meridian Bioscience Canada Inc., Québec (CA)

( * ) Notice: Subject to any disclaimer, the term of this patent is extended or adjusted under 35 U.S.C. 154(b) by 265 days.

(21) Appl. No.: 15/260,565

(22) Filed: Sep. 9, 2016

(65) Prior Publication Data

US 2017/0056878 A1    Mar. 2, 2017

Related U.S. Application Data

(62) Division of application No. 14/003,640, filed as application No. PCT/IB2012/051076 on Mar. 7, 2012, now Pat. No. 9,562,262.

(Continued)

(51) Int. Cl.
*G01N 21/64*    (2006.01)
*G01N 21/07*    (2006.01)
(Continued)

(52) U.S. Cl.
CPC ........ *B01L 3/50273* (2013.01); *B01F 3/0861* (2013.01); *B01F 13/0059* (2013.01);
(Continued)

(58) Field of Classification Search
None
See application file for complete search history.

(56) References Cited

U.S. PATENT DOCUMENTS 3,970,245 A    7/1976    Aeschlimann
4,456,581 A    6/1984    Edelmann et al.
(Continued)

FOREIGN PATENT DOCUMENTS

CA    2717939 A1    4/2011
EP    0608006 A2    7/1994
(Continued)

OTHER PUBLICATIONS

Communication under Rule 71(3) EPC dated Oct. 25, 2016, issued in Application No. 12 754 898.0, 7 pages.
(Continued)

*Primary Examiner* — Jill A Warden
*Assistant Examiner* — Brittany I Fisher
(74) *Attorney, Agent, or Firm* — Meunier Carlin & Curfman LLC

(57) ABSTRACT

A fluidic centripetal apparatus for testing components of a biological material in a fluid is presented. The fluidic centripetal device is adapted to be received within a rotatable holder. The apparatus comprises a fluidic component layer having fluidic features on at least a front face and a bottom component layer bonded to a rear of the fluidic component layer thereby creating a fluidic network through which the fluid flows under centripetal force. In one embodiment, the fluidic feature may be a bottom-fillable chamber coupled to an entry channel for receiving the fluid, the chamber inlet being provided at an outer side of the bottom-fillable chamber. In another embodiment, the fluidic feature may be a retention chamber coupled to an entry channel for receiving the fluid, a container wholly provided in the retention chamber and containing a liquid diluent, the container maintaining the liquid diluent in the container until it releases it in the retention chamber upon application of an external force to the container, thereby restoring the fluidic
(Continued)

connection between the liquid diluent and the fluid in the retention chamber. Additionally, the retention chamber can have a flow decoupling receptacle for receiving the fluid, located at the outer side of the retention chamber and interrupting a fluidic connection between the entry and exit of the retention chamber. A test apparatus and a testing method using a fluidic centripetal device for testing components of a biological material in a fluid are also provided.

29 Claims, 36 Drawing Sheets

Specification includes a Sequence Listing.

Related U.S. Application Data

(60) Provisional application No. 61/450,373, filed on Mar. 8, 2011.

(51) Int. Cl.

| | | |
|---|---|---|
| *G01N 21/03* | (2006.01) | |
| *B01F 3/08* | (2006.01) | |
| *B01F 15/02* | (2006.01) | |
| *B01F 13/00* | (2006.01) | |
| *B01L 7/00* | (2006.01) | |
| *B01L 3/00* | (2006.01) | |
| *G01N 35/00* | (2006.01) | |
| *C12Q 1/686* | (2018.01) | |
| *B01L 9/00* | (2006.01) | |
| *G01N 35/04* | (2006.01) | |

(52) U.S. Cl.
CPC ...... *B01F 15/0212* (2013.01); *B01F 15/0233* (2013.01); *B01L 3/502715* (2013.01); *B01L 3/502746* (2013.01); *B01L 7/525* (2013.01); *C12Q 1/686* (2013.01); *G01N 21/07* (2013.01); *G01N 21/645* (2013.01); *G01N 35/00029* (2013.01); *G01N 35/00871* (2013.01); *B01F 2215/0037* (2013.01); *B01L 9/527* (2013.01); *B01L 2200/027* (2013.01); *B01L 2200/028* (2013.01); *B01L 2200/0605* (2013.01); *B01L 2200/0631* (2013.01); *B01L 2200/0668* (2013.01); *B01L 2200/0684* (2013.01); *B01L 2200/147* (2013.01); *B01L 2200/16* (2013.01); *B01L 2300/023* (2013.01); *B01L 2300/043* (2013.01); *B01L 2300/069* (2013.01); *B01L 2300/0609* (2013.01); *B01L 2300/0681* (2013.01); *B01L 2300/0803* (2013.01); *B01L 2300/087* (2013.01); *B01L 2300/0867* (2013.01); *B01L 2300/18* (2013.01); *B01L 2400/043* (2013.01); *B01L 2400/0409* (2013.01); *B01L 2400/0677* (2013.01); *B01L 2400/0683* (2013.01); *B01L 2400/082* (2013.01); *G01N 21/0332* (2013.01); *G01N 2021/0325* (2013.01); *G01N 2035/0091* (2013.01); *G01N 2035/00158* (2013.01); *G01N 2035/00495* (2013.01); *G01N 2035/0451* (2013.01)

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,923,978 A | 5/1990 | McCormick |
| 4,965,188 A | 10/1990 | Mullis et al. |
| 5,038,852 A | 8/1991 | Johnson et al. |
| D329,902 S | 9/1992 | Kim |
| 5,230,866 A | 7/1993 | Shade et al. |
| 5,304,348 A | 4/1994 | Burd et al. |
| 5,333,675 A | 8/1994 | Mullis et al. |
| 5,457,053 A | 10/1995 | Burd et al. |
| 5,475,610 A | 12/1995 | Atwood et al. |
| 5,591,643 A | 1/1997 | Schembri |
| 5,602,756 A | 2/1997 | Atwood et al. |
| 5,639,428 A | 6/1997 | Cottingham |
| 5,656,493 A | 8/1997 | Mullis et al. |
| 5,871,908 A | 2/1999 | Henco et al. |
| D415,840 S | 10/1999 | Lamond et al. |
| 6,063,589 A | 5/2000 | Kellogg et al. |
| 6,100,084 A | 8/2000 | Miles et al. |
| 6,143,248 A | 11/2000 | Kellogg et al. |
| 6,174,670 B1 | 1/2001 | Wittwer et al. |
| 6,245,514 B1 | 6/2001 | Wittwer |
| 6,210,882 B1 | 8/2001 | Landers et al. |
| 6,302,134 B1 | 10/2001 | Kellogg et al. |
| 6,303,305 B1 | 10/2001 | Wittwer et al. |
| 6,391,264 B2 | 5/2002 | Hammer et al. |
| 6,431,476 B1 | 8/2002 | Taylor et al. |
| 6,440,725 B1 | 8/2002 | Pourahmadi et al. |
| 6,485,690 B1 | 11/2002 | Pfost et al. |
| 6,503,720 B2 | 1/2003 | Wittwer et al. |
| 6,527,432 B2 | 3/2003 | Kellogg et al. |
| 6,565,815 B1 | 5/2003 | Chang et al. |
| 6,569,627 B2 | 5/2003 | Wittwer et al. |
| 6,627,159 B1 | 9/2003 | Bedingham et al. |
| 6,632,399 B1 | 10/2003 | Kellogg et al. |
| 6,635,492 B2 | 10/2003 | Gunter |
| 6,691,041 B2 | 2/2004 | Sagner et al. |
| 6,703,236 B2 | 3/2004 | Atwood |
| 6,706,519 B1 | 3/2004 | Kellogg et al. |
| 6,720,187 B2 | 4/2004 | Bedingham et al. |
| 6,734,401 B2 | 5/2004 | Bedingham et al. |
| 6,776,965 B2 | 8/2004 | Wyzgol et al. |
| 6,780,617 B2 | 8/2004 | Chen |
| 6,787,338 B2 | 9/2004 | Wittwer et al. |
| 6,814,934 B1 | 11/2004 | Higuchi |
| 6,818,435 B2 | 11/2004 | Carvalho et al. |
| 6,855,553 B1 | 2/2005 | Bedingham et al. |
| 6,889,468 B2 | 5/2005 | Bedingham et al. |
| 6,964,862 B2 | 11/2005 | Chen |
| 6,987,253 B2 | 1/2006 | Bedingham et al. |
| 7,079,468 B2 | 7/2006 | Worthington et al. |
| 7,081,226 B1 | 7/2006 | Wittwer et al. |
| 7,152,616 B2 | 12/2006 | Zucchelli et al. |
| 7,164,107 B2 | 1/2007 | Bedingham et al. |
| 7,238,269 B2 | 7/2007 | Gason et al. |
| 7,238,321 B2 | 7/2007 | Wittwer et al. |
| 7,322,254 B2 | 1/2008 | Bedingham et al. |
| 7,323,660 B2 | 1/2008 | Bedingham et al. |
| 7,332,126 B2 | 2/2008 | Tooke et al. |
| 7,332,326 B1 | 2/2008 | Kellogg et al. |
| D564,667 S | 3/2008 | Bedingham et al. |
| D569,526 S | 5/2008 | Duffy et al. |
| 7,387,887 B2 | 6/2008 | Wittwer et al. |
| 7,396,508 B1 | 7/2008 | Richards et al. |
| 7,402,817 B2 | 7/2008 | Gavrilov et al. |
| 7,435,933 B2 | 10/2008 | Bedingham et al. |
| 7,476,361 B2 | 1/2009 | Kellogg et al. |
| 7,494,771 B2 | 2/2009 | Picard et al. |
| 7,507,575 B2 | 3/2009 | Bedingham et al. |
| 7,527,763 B2 | 5/2009 | Bedingham et al. |
| 7,648,835 B2 | 1/2010 | Breidford et al. |
| 7,649,358 B2 | 1/2010 | Toumazou et al. |
| D612,276 S | 3/2010 | Duffy et al. |
| 7,709,249 B2 | 5/2010 | Bedingham et al. |
| D617,909 S | 6/2010 | Taniguchi et al. |
| 7,727,473 B2 | 6/2010 | Ching et al. |
| 7,754,148 B2 | 7/2010 | Yu et al. |
| 7,763,210 B2 | 7/2010 | Bedingham et al. |
| 7,767,937 B2 | 8/2010 | Bedingham et al. |
| 7,776,267 B2 | 8/2010 | Lee et al. |
| 7,785,535 B2 | 8/2010 | Chen et al. |
| 7,790,110 B2 | 9/2010 | Cho et al. |
| 7,794,799 B1 | 9/2010 | Kim et al. |
| 7,833,486 B2 | 11/2010 | Fielden et al. |

(56) References Cited

U.S. PATENT DOCUMENTS

| | | |
|---|---|---|
| 7,837,948 B2 | 11/2010 | Park |
| 7,888,015 B2 | 2/2011 | Toumazou et al. |
| 7,935,319 B2 | 5/2011 | Andersson et al. |
| 7,998,708 B2 | 8/2011 | Handique et al. |
| 8,043,581 B2 | 10/2011 | Ganesan |
| 8,057,758 B2 | 11/2011 | Bedingham et al. |
| 8,088,616 B2 | 1/2012 | Handique |
| 8,105,551 B2 | 1/2012 | Park et al. |
| 8,133,671 B2 | 3/2012 | Williams et al. |
| D663,041 S | 7/2012 | Henssler et al. |
| 8,268,603 B2 | 9/2012 | Taylor et al. |
| 8,415,103 B2 | 4/2013 | Handique |
| 8,441,629 B2 | 5/2013 | Kolesnychenko et al. |
| 8,450,101 B2 | 5/2013 | Gomi et al. |
| 8,482,734 B2 | 7/2013 | Ducrée |
| D689,193 S | 9/2013 | Shinohara et al. |
| D705,437 S | 5/2014 | Chamberlin et al. |
| 2005/0136545 A1 | 6/2005 | Schmid et al. |
| 2005/0142571 A1 | 6/2005 | Parthasarathy et al. |
| 2005/0202471 A1 | 9/2005 | Tooke et al. |
| 2005/0244837 A1 | 11/2005 | McMillan |
| 2006/0088844 A1 | 4/2006 | Xu |
| 2006/0278287 A1 | 12/2006 | Fielden et al. |
| 2006/0281192 A1 | 12/2006 | Harding et al. |
| 2007/0007270 A1 | 1/2007 | Bedingham et al. |
| 2007/0009382 A1 | 1/2007 | Bedingham et al. |
| 2007/0009391 A1 | 1/2007 | Bedingham et al. |
| 2007/0010007 A1 | 1/2007 | Aysta et al. |
| 2007/0125942 A1 | 6/2007 | Kido |
| 2007/0263049 A1 | 11/2007 | Preckel et al. |
| 2007/0280859 A1 | 12/2007 | Kido et al. |
| 2007/0292858 A1 | 12/2007 | Chen et al. |
| 2008/0038737 A1 | 2/2008 | Smith et al. |
| 2008/0073546 A1 | 3/2008 | Andersson et al. |
| 2008/0101993 A1 | 5/2008 | Andersson et al. |
| 2008/0149840 A1 | 6/2008 | Handique et al. |
| 2008/0193336 A1 | 8/2008 | Cho et al. |
| 2008/0305006 A1 | 12/2008 | Cho et al. |
| 2009/0035847 A1 | 2/2009 | Cho et al. |
| 2010/0009431 A1 | 1/2010 | Cho et al. |
| 2010/0044918 A1 | 2/2010 | Lee et al. |
| 2010/0093105 A1 | 4/2010 | Lee et al. |
| 2010/0105029 A1 | 4/2010 | Ririe et al. |
| 2010/0167304 A1 | 7/2010 | Bedingham et al. |
| 2010/0221728 A1 | 9/2010 | Namkoong et al. |
| 2010/0245815 A1 | 9/2010 | Ducree |
| 2010/0255589 A1* | 10/2010 | Saiki .................... G01N 33/02 436/45 |
| 2010/0290955 A1 | 11/2010 | Cho et al. |
| 2011/0020194 A1 | 1/2011 | Lee et al. |
| 2011/0097280 A1 | 4/2011 | Dees et al. |
| 2011/0189701 A1 | 8/2011 | Kim |
| 2011/0201101 A1 | 8/2011 | Lee et al. |
| 2011/0210257 A9 | 9/2011 | Handique et al. |
| 2011/0269151 A1 | 11/2011 | Kim |

FOREIGN PATENT DOCUMENTS

| | | |
|---|---|---|
| EP | 1407051 B1 | 4/2006 |
| EP | 2198965 A1 | 6/2010 |
| EP | 2283924 | 2/2011 |
| JP | S1234360 | 10/1986 |
| JP | 5149958 | 6/1993 |
| JP | 5508709 | 12/1993 |
| JP | 10501340 | 2/1998 |
| JP | 3061414 | 4/2000 |
| JP | 2001502793 | 2/2001 |
| JP | 2003270252 | 9/2003 |
| JP | 2003533681 | 11/2003 |
| JP | 2005326432 | 11/2005 |
| JP | 2007500850 | 1/2007 |
| JP | 2007198949 | 8/2007 |
| JP | 200861649 | 3/2008 |
| JP | 2009500627 | 1/2009 |
| JP | 2009148735 | 7/2009 |
| JP | 201127421 | 2/2011 |
| KR | 20080071786 A | 8/2008 |
| WO | 9118656 | 12/1991 |
| WO | 9533986 | 12/1995 |
| WO | 9813684 | 4/1998 |
| WO | 0040750 A1 | 7/2000 |
| WO | 0187486 | 11/2001 |
| WO | 2004050242 A2 | 6/2004 |
| WO | 2007001084 | 1/2007 |
| WO | 2007005854 | 1/2007 |
| WO | 2007005854 A2 | 1/2007 |
| WO | 2008134470 A2 | 11/2008 |
| WO | 2009003985 A1 | 1/2009 |
| WO | 2012120463 | 9/2012 |

OTHER PUBLICATIONS

Siegrist et al., "Microfluidics for IVD Analysis: Triumphs and Hurdles of Centrifugal Platforms. Part 1 : Molecular fundamentals", IVD Technology, Jan. 2010, 9 pages, Available on the Internet at www.ivdtechnology.com/print/1176 on Jan. 27, 2014.

Siegrist et al., "Microfluidics for IVD Analysis: Triumphs and Hurdles of Centrifugal Platforms. Part 2 : Centrifugal mirofluidics", IVD Technology, Jan. 2010, 9 pages, Available on the internet at www.ivdtechnology.com/print/1396 on Jan. 27, 2014.

Siegrist et al., "Microfluidics for IVD Analysis: Triumphs and Hurdles of Centrifugal Platforms. Part 3 : Challenges and solutions", IVD Technology, Sping 2010, pp. 22-26, IVD Technology DX Directions, USA.

Focke et al., "Centrifugal microfluidic system for primary amplification and secondary real-time PCR†", Lab on a Chip, 2010, pp. 3210-3212, vol. 10, The Royal Society of Chemistry, UK.

Mark et al., "Aliquoting Structure for Centrifugal Microfluidics Based on a New Pneumatic Valve", MEMS 2008, Jan. 13-17, 2008, pp. 611-614, IEEE, Tucson, AZ.

Kido et al., "A novel, compact disk-like centrifugal microfluidics system for cell lysis and sample homogenization", Colloids and Surfaces B: Biointerfaces, Mar. 2007, pp. 44-51, vol. 58, Elsevier, USA.

Lutz et al., "Isothermal Polymerase Amplification in a Centrifugal Microfluidic Foil Cartbridge", Procedia Chemistry, 2009, pp. 529-531, vol. 1, Elsevier, USA.

Bostick et al., "Portable Centrifugal Analyzer for the Determination of Rapid Reaction Kinetics", Analytical Chemistry, Feb. 1980, pp. 300-306, vol. 52, No. 2, American Chemical Society, Tennessee.

Ducrée et al., "The centrifugal microfluidic Bio-Disk platform", Journal of Micromechanics and Microengineering, 2007, pp. S103-S115, vol. 17, IOPscience, UK.

Abi-Samra et al., "Infrared controlled waxes for liquid handling and storage on a CDmicrofluidic Platform", Lab on a Chip, 2011, pp. 723-726, vol. 11, The Royal Society of Chemistry, UK.

Hakenberg, "Re-design and validation of a centrifugal microfluidic lysis, switching and aliquoting structure", Diploma Thesis, Aug. 2008-Jan. 2009, 72 pages, Albert—Ludwigs—University Freiburg, Germany.

Glide et al., Manufacturing obstacles in IVD product development, IVD Technology, Jan. 2010, pp. 1-8. Available on the internet at www.ivdtechnology.com/print/1395 on Nov. 19, 2012.

Partial European Search Report and Written Opinion issued in corresponding application No. 17187723.6 dated Dec. 15, 2017.

* cited by examiner

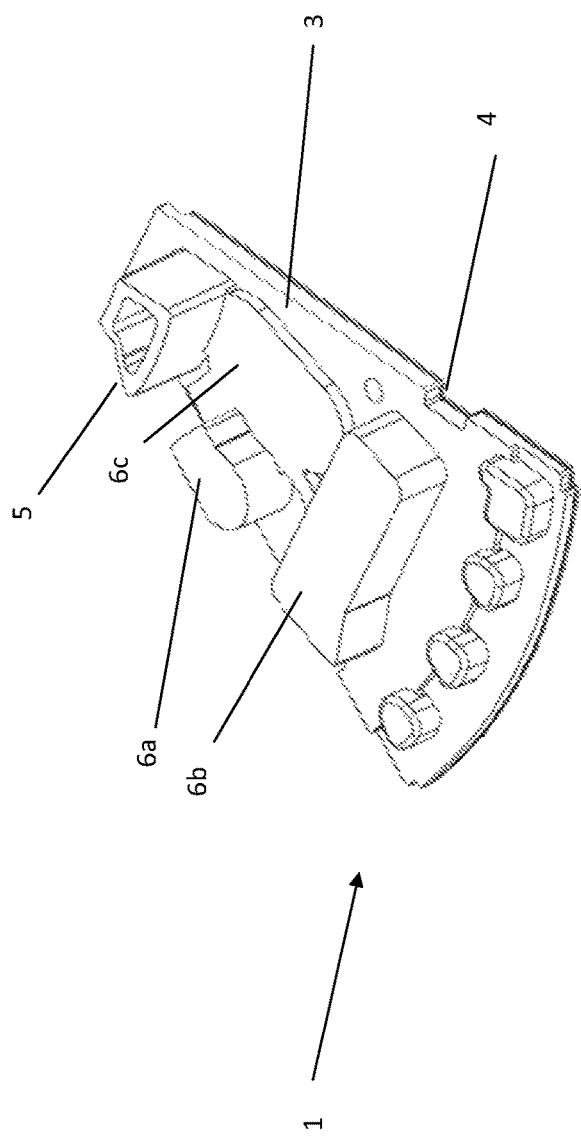
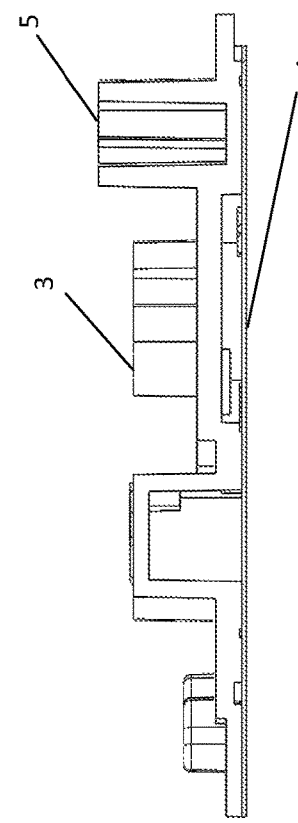
Fig. 1C
Fig. 1D

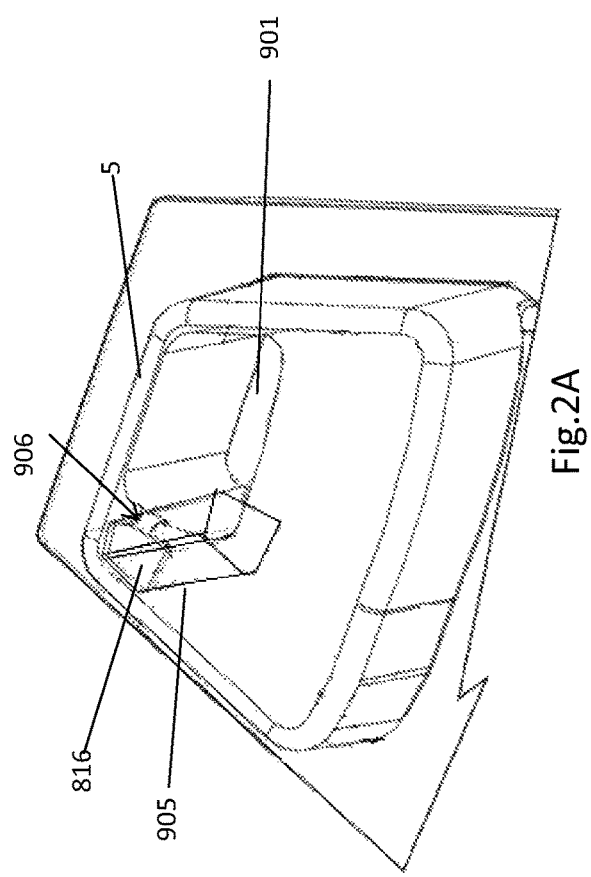
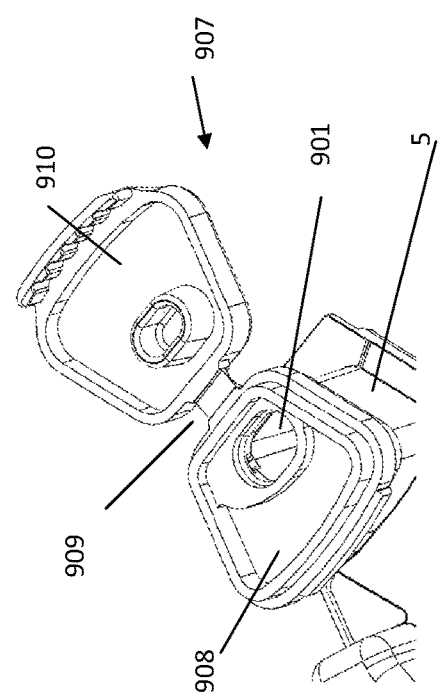
Fig. 2A
Fig. 2B

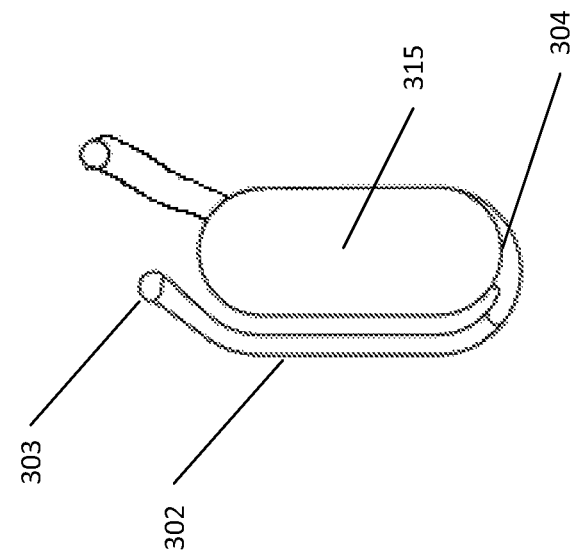
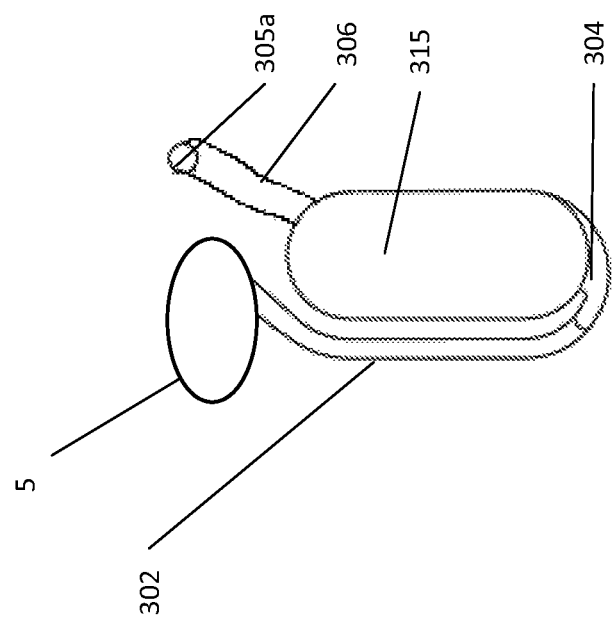

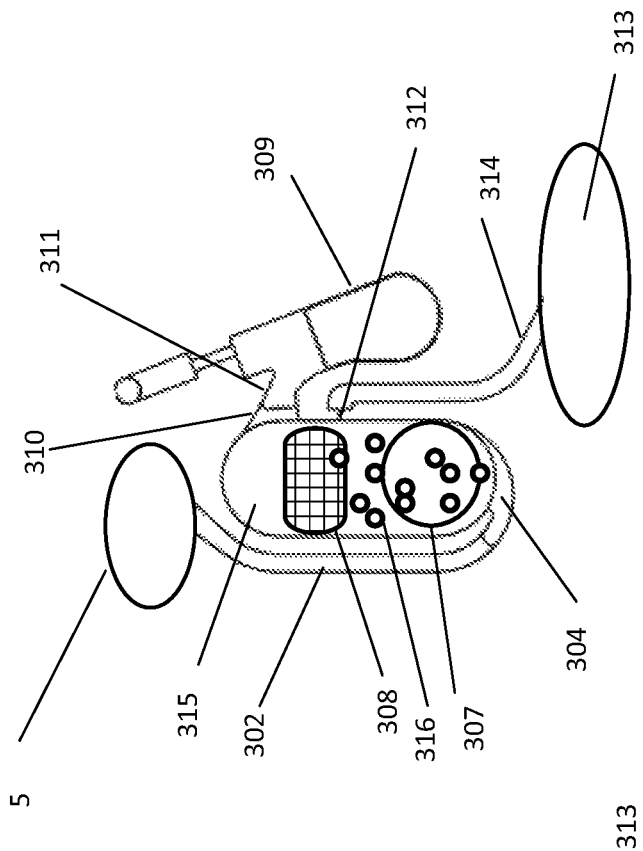
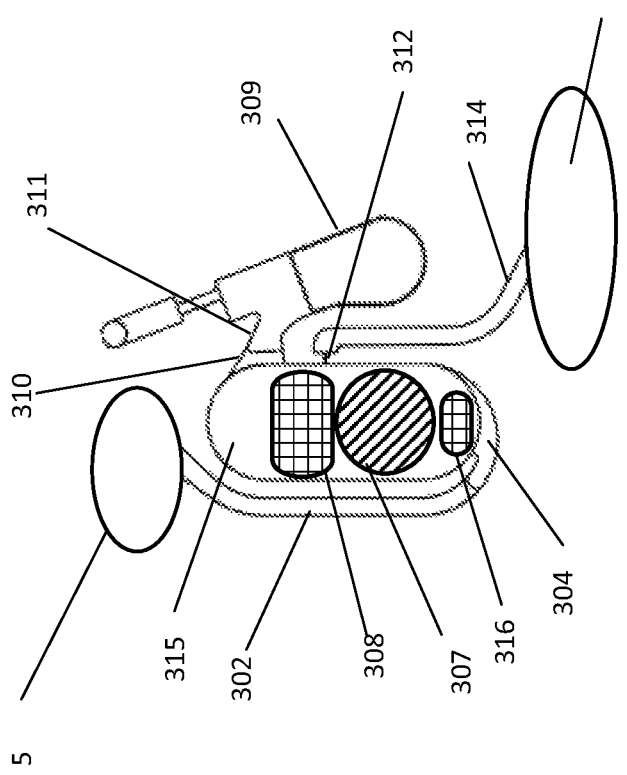

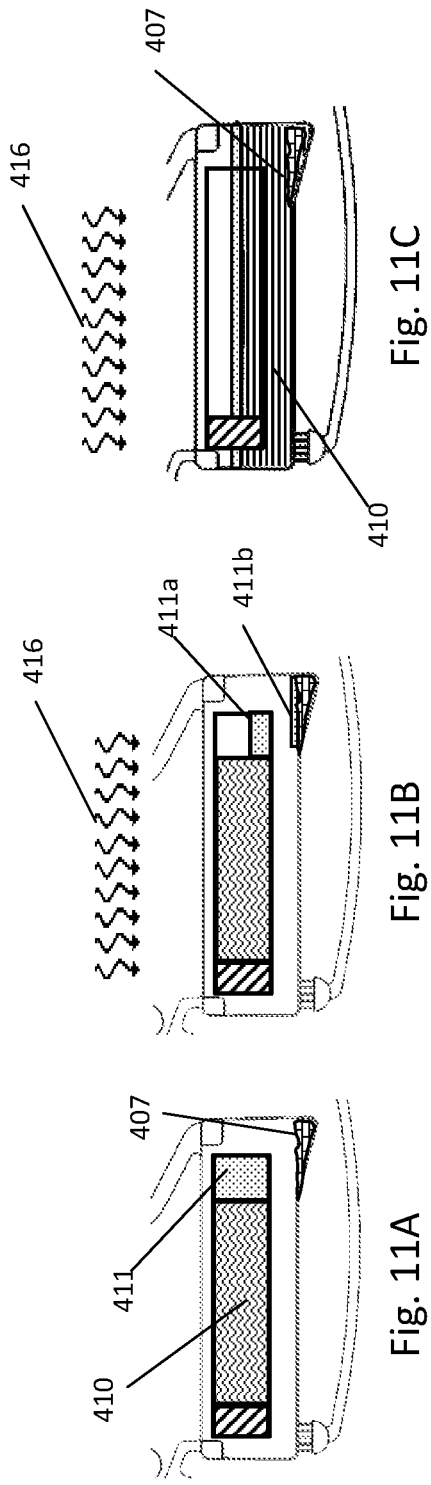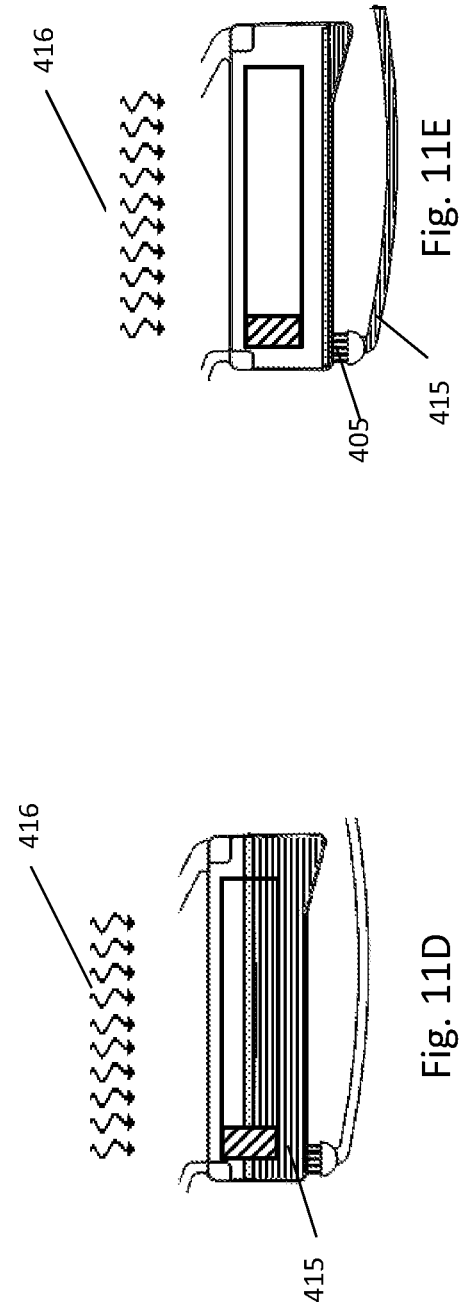

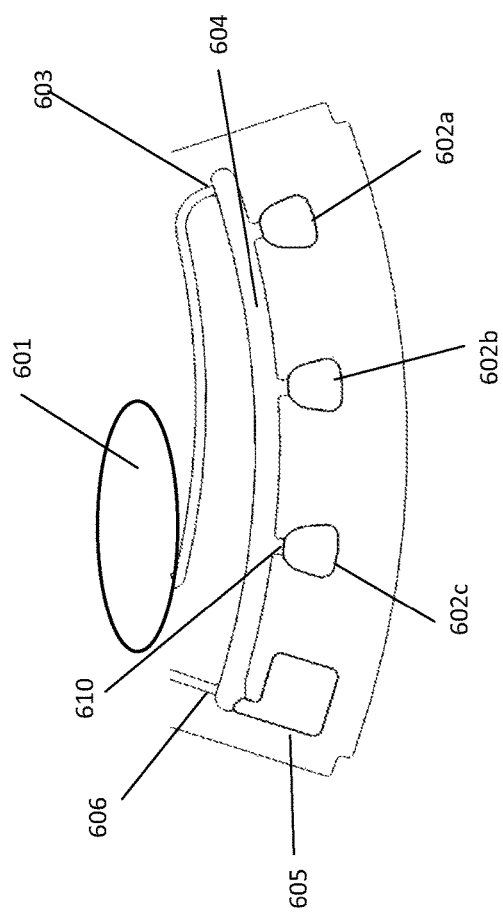
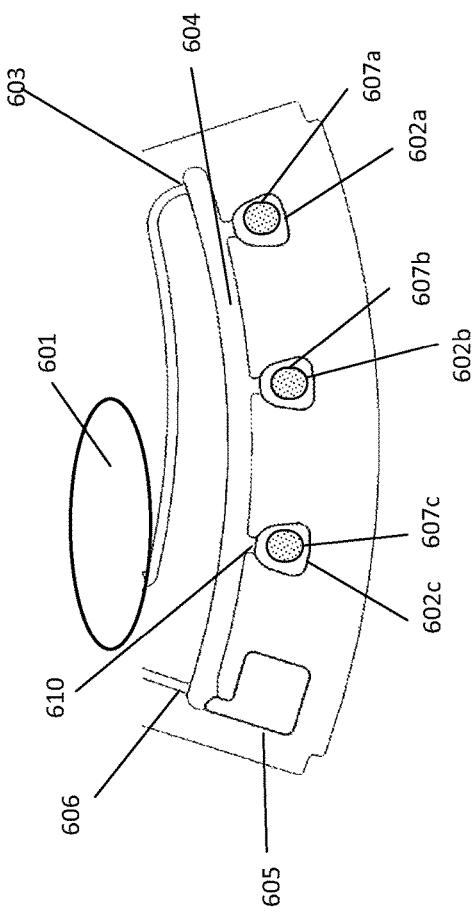
Fig. 14A
Fig. 14B

FLUIDIC CENTRIPETAL DEVICE

CROSS-REFERENCE TO RELATED APPLICATIONS

The present application is a Divisional of U.S. Ser. No. 14/003,640 entitled "FLUIDIC CENTRIPETAL DEVICE" filed Sep. 10, 2013, which is a national phase entry of PCT Application No. PCT/IB2012/051076, entitled "FLUIDIC CENTRIPETAL DEVICE" filed on Mar. 7, 2012, which in turn claims priority of U.S. provisional Appl. No. 61/450,373 filed on Mar. 8, 2011, the specifications of which are hereby incorporated by reference.

TECHNICAL FIELD

The invention relates to fluidic centripetal devices.

BACKGROUND OF THE ART

Molecular diagnostics comprise the detection of molecular compounds useful to identify diseases, species, individuals, etc. These molecular compounds can be, for example, ions, sugars, metabolites, fatty acids, amino acids, nucleic acids, proteins, or lipids. Nucleic acid testing (NAT) comprises the identification of specific nucleic acids from pathogens, or the identification of specific nucleic acid sequences related to diseases such as cancer, genetic diseases, genetic signature of species or individuals or markers for personalized medicine. NAT protocols often start with a sample preparation step where cells are lysed to free their nucleic acids. The nucleic acids are then specifically prepared in order to be ready for a target amplification procedure such as for example polymerase chain reaction (PCR) or isothermal amplification Recombinase Polymerase Amplification (RPA) or other nucleic acid amplification methods. Target amplification produces amplicons which can be analyzed in real time, meaning during the amplification, or at the end of the amplification in an agarose gel or on a microarray for example. Amplification procedures also exist for amplifying a signal generated by the detection of the analyte and these signal amplification approaches can also be associated with target amplification procedures. These technologies require complex protocols carried out by highly qualified personnel in dedicated facilities. For these reasons, not all laboratories, hospitals or healthcare facilities can run molecular diagnostics.

There is a need to automate complex molecular diagnostic protocols. Some approaches rely on high-throughput robotic units which are usually very expensive and can require a lot of space. There is a growing need to develop more compact instruments and mobile instrumentations such as Point-of-Care (POC) diagnostics and to miniaturize and integrate the steps of an assay—from sample preparation to answer—onto a single disposable device (ex: lab-on-a-chip devices or micro Total Analysis Systems: µTAS).

One of the main difficult steps to integrate into a disposable microfluidic system is sample preparation. Sample preparation usually starts with a cell lysis step which can be chemical and/or mechanical. Then to remove or at least control potential inhibitors of the testing process, nucleic acids can be purified. The most common techniques used to purify nucleic acids are based on solid-phase adsorption of the nucleic acids under specific conditions of pH and salt. Enzymatic reaction inhibitors such as proteins, metals and other molecules are washed away from the nucleic acids adsorbed onto the solid phase. Nucleic acids are then recovered from the solid phase by using an appropriate elution solution. The whole process requires different solutions, which need to be stored and released, a solid phase matrix and different reaction chambers. This complicates the process to integrate into a compact disposable microfluidic cartridge.

In the development of fluidic devices, there is a need to displace fluids in and out of the different processing areas in a controlled manner. Pumping and valving components are usually used.

Some have developed fluidic units enabling the automation of molecular diagnostics. For example, there exists a sample preparation cartridge with a rotary valve and a piston pump to move the fluids in the different reservoirs. There also exists mechanical lysis using ultrasounds and hard particles. Other devices use a flexible plastic assembly to lyse cells and transfer the fluids between container sectors by compressing the flexible material at a specific location. These fluidic units require several actuators to be able to perform the tasks.

The use of centripetal platforms provides a simple and effective format for the implementation of pumping and valving options. When spinning, centrifugally-induced fluid pressure causes fluid flow inside the fluidic device.

Centripetal pumping provides many advantages over other alternative pumping methods such as a syringe, piston, peristaltic, or electro-osmotic pumping. Centripetal pumping has lower electrical power requirements (the only active actuation being that needed for rotation), is independent of fluid pH or ionic strength, and does not need any external fluidic interconnections or tubing. Consequently, different assay steps requiring different sample and buffer properties (e.g., surface energy, pH) can be combined into a single fluidic centripetal device.

Another advantage of centripetal pumping is that a valve can be implemented by the geometric design of the fluidic microchannels in such a way that capillary forces balance the centripetal force due to disc rotation. By designing microfluidic structures with capillary valves of different shapes and at different positions relative to the fluidic centripetal device rotation center, the liquid flow can be interrupted and resumed by controlling the rotational speed.

Since most analytical processes for biological material require several steps, passive valving may be difficult to implement robustly. For more robustness, there is a need to implement active valves in a centripetal device. For example, it is possible to block a microfluidic channel using a phase-change material such as paraffin wax plug. This valve type is independent of the rotational speed and can be actuated by heat. For example, a plug of heat generating particles and phase-change materials can also be used. The particles absorb the electromagnetic waves from an external device (e.g. laser, IR lamp) and the phase-change material melts with the heat generated by the particles. Phase-change material valves have been described to block a fluidic channel (U.S. Pat. No. 7,837,948) and used on a centripetal nucleic acid testing device (Publ. EP 2375256).

Some active valve approaches for centripetal devices are based on actuation by an electromagnetic wave. For example, a valve closure at a desired location can be opened without contact through laser ablation and without piercing the external layer of the microfluidic device (see for example Publ. EP 1930635, PCT Pat. Appl. Publ. No. WO2004/050242, US Pat. Appl. Publ. US 2009/0189089, U.S. Pat. Nos. 7,709,249, 7,323,660).

The actuation of a phase-change material valve can be done by using electrodes which form a resistive heater onto the substrate itself. The electrodes generate heat at a specific region of interest in the microfluidic network to melt the phase-change material.

There still remains a need for an improved fluidic centripetal device with sample flow control.

SUMMARY

The fluidic centripetal device described herein could allow combining simplified structures and actuators ensuring sample preparation, volume metering, controlled displacement of volumes in a minimum of chambers and channels while permitting the storage of both dried and wet reagents required for multiplex amplification and detection of nucleic acids.

The described fluidic centripetal device is well suited to be implemented in point of care or bench top systems to simultaneously process multiple samples and yield rapid results.

According to a first aspect of the invention, there is provided a fluidic centripetal device in which the combined macrostructures and microstructures ensure a simplified sample preparation method. The fluids can be moved using centripetal force applied to a rotor which provides centripetal force. The process is simplified in order to minimize the use of liquids and robustly use simple valving.

According to a second aspect of the invention, there is provided a method to extract and prepare nucleic acids in order to control potential inhibitors present in a sample which can interfere with the amplification and/or detection. In addition, the fluidic circuit can provide pre and post lysis measurement of the sample volume. This allows volume definition. The volume definition can be achieved by subtracting a liquid volume defined by the difference between 2 meniscuses. This allows use of a simple collection device instead of the usual high precision micropettor required to precisely measure small volumes introduced into the fluidic centripetal device, which greatly facilitates manipulation by the operator.

According to a third aspect of the invention, there is provided a fluidic centripetal device combining sample preparation and multiplex real-time nucleic acid amplification detection. The fluidic centripetal device includes a intake receptacle in fluidic communication with a bottom-filling chamber (which can be used for homogenization, cell lysis, control of inhibitors and concentration of microbes) in fluidic communication with a retention chamber in fluidic communication with a detection area which can use a distribution channel to split the sample in two or more detection chambers, if required, for amplification and detection. The channels and chambers of the fluidic centripetal device can be self-vented by a close loop system providing air displacement while keeping the system close thus helping to prevent contamination.

According to a fourth aspect of the invention, there is provided an instrument to control the functions of the fluidic centripetal device. The system comprises mechanical components such as a motor to rotate the fluidic centripetal device, magnets to move the translocatable member in the fluidic centripetal device, thermal elements to control the temperature of the fluidic device, optical components to measure fluorescence signals and an electronic and human machine interface, for example with a touch screen device.

In one embodiment, the instrument provides an air temperature control in multiple zones of the fluidic centripetal device.

In one embodiment, the instrument provides a temperature control in multiple zones on a centripetal device by placing thermal elements in contact with the rotating fluidic centripetal device.

According to a broad aspect, there is provided a fluidic centripetal device for testing components of a biological material in a fluid sample, the apparatus comprising a fluidic component layer with a substantially flat back side, the fluidic component layer having a shape adapted to be received within a rotatable holder, the rotatable holder having a center of rotation and an outer edge, the fluidic component layer radially extending between the center of rotation and the outer edge, an inner side of the fluidic component layer being located towards the center of rotation and an outer side of the fluidic component layer being located towards the outer edge, the fluidic component layer being shaped to include: a sample intake receptacle for receiving the sample, the sample intake receptacle extending outwardly from the fluidic component layer and being located near the inner side, the sample intake receptacle ending in a sample outlet; an entry channel for circulating the fluid sample, the entry channel being coupled to the sample outlet at one end and to a chamber inlet at another end; a bottom-fillable chamber coupled to the entry channel at the chamber inlet for receiving the fluid sample, the chamber inlet being provided at an outer side of the bottom-fillable chamber.

In one embodiment, the apparatus further comprises a cap for the sample intake receptacle for closing access to the sample intake receptacle.

In one embodiment, the bottom-fillable chamber is oblong shaped and radially extends between the inner side and the outer side.

In one embodiment, the bottom-fillable chamber includes at least one translocatable member that translocates within the bottom-fillable chamber in response to an external fluctuating magnetic field.

In one embodiment, the translocatable member that translocates in response to a fluctuating magnetic field is comprised of paramagnetic material.

In one embodiment, the translocatable member that translocates in response to a fluctuating magnetic field is a disk or a sphere.

In one embodiment, the translocatable member is ferromagnetic.

In one embodiment, the bottom-fillable chamber further comprises at least one object that does not react in response to a fluctuating magnetic field.

In one embodiment, the object is at least one of a bead, a glass bead, a zirconium bead, a resin, and a bead and resin slurry.

In one embodiment, the object is coated with a chelating material adapted to interact with components of the sample.

In one embodiment, each the object and the translocatable member are greater in size than a size of the chamber inlet.

In one embodiment, the bottom-fillable chamber is a homogenization chamber.

In one embodiment, the bottom-fillable chamber is a lysis chamber.

In one embodiment, the bottom-fillable chamber is a clarification chamber.

In one embodiment, the bottom-fillable chamber is a target concentrating chamber.

In one embodiment, the apparatus further comprises an overflow chamber coupled to a surplus outlet for the bottom-fillable chamber, the surplus outlet allowing exit of part of the fluid sample from the bottom-fillable chamber to the overflow chamber.

In one embodiment, the surplus outlet is provided near the inner side of the bottom-fillable chamber.

In one embodiment, the surplus outlet is provided on one longitudinal side of the bottom-fillable chamber.

In one embodiment, the apparatus further comprises an exit outlet for the bottom-fillable chamber, the exit outlet allowing exit of the sample from the bottom-fillable chamber.

In one embodiment, the exit outlet is located on one longitudinal side of the bottom-fillable chamber.

In one embodiment, each the object and the translocatable member are greater in size than a size of the exit outlet.

In one embodiment, the surplus outlet is located closer to the inner side than the exit outlet.

In one embodiment, the apparatus further comprises a retention chamber, the retention chamber being coupled to the exit outlet at an inner side of the retention chamber, the retention chamber being located closer to the outer side of the fluidic component layer than the bottom-fillable chamber.

In one embodiment, the retention chamber is coupled to the exit outlet via a transfer channel, the transfer channel for circulating at least a portion of the fluid sample from the bottom-fillable chamber to the retention chamber.

In one embodiment, the apparatus further comprises a container wholly provided in the retention chamber and containing a liquid reactant, the container being adapted to maintain the liquid reactant in the container and to release the liquid reactant in the retention chamber upon application of an external force to the retention chamber.

According to a broad aspect, there is provided a fluidic centripetal device for mixing a liquid reactant with a fluid sample, the apparatus comprising a fluidic component layer with a substantially flat back side, the fluidic component layer having a shape adapted to be received within a rotatable holder, the rotatable holder having a center of rotation and an outer edge, the fluidic component layer radially extending between the center of rotation and the outer edge, an inner side of the fluidic component layer being located towards the center of rotation and an outer side of the fluidic component layer being located towards the outer edge, the fluidic component layer being molded to include: a sample intake receptacle for receiving the sample, the sample intake receptacle extending outwardly from the fluidic component layer and being located near the inner side, the sample intake receptacle ending in a sample outlet; a retention chamber coupled to the sample intake receptacle for receiving the fluid sample into the retention chamber; a container wholly provided in the retention chamber and containing a liquid reactant, the container being adapted to maintain the liquid reactant in the container and to release the liquid reactant in the retention chamber upon application of an external force to the retention chamber.

In one embodiment, the apparatus further comprises an entry channel for circulating the fluid sample from the sample outlet to a retention chamber inlet of the retention chamber.

In one embodiment, the retention chamber has a receptacle for receiving the fluid sample.

In one embodiment, the receptacle is located at the outer side of the retention chamber.

In one embodiment, a capacity volume of the receptacle is at least equal to a capacity volume of the sample transferred to the retention chamber.

In one embodiment, the receptacle includes a dried reactant.

In one embodiment, the dried reactant is an inhibitor control reagent.

In one embodiment, the retention chamber is a dilution chamber.

In one embodiment, the receptacle of the retention chamber is emptied upon release of the diluent.

In one embodiment, the container is made of one of glass, capillary glass, polymeric thermoplastic and or heat sensitive material.

In one embodiment, the liquid reactant is a dilution agent.

In one embodiment, the liquid reactant is one of water, buffer, ion, polymer, protein, sugar, nucleic acid, and/or a-dryable part of a solution.

In one embodiment, the container has a cap made of a heat-sensitive material adapted to be melted at a melt temperature, allowing the liquid reactant to travel from within the container to outside of the container in the retention chamber.

In one embodiment, the container is made of heat sensitive material.

In one embodiment, the external force is one of mechanical, electrical, electromagnetic, heat, shock and acoustic force.

In one embodiment, the container has a releasable opening.

In one embodiment, the retention chamber has a distribution outlet for the retention chamber, the distribution outlet being located at an outer side of the retention chamber, the distribution outlet being coupled to a transversal distribution channel at an inner side of the transversal distribution channel at a first transversal end of the distribution channel, the transversal distribution channel having a series of at least one cuvette provided at an outer side of the transversal distribution channel.

In one embodiment, the distribution outlet is coupled to the distribution channel via a transfer channel.

In one embodiment, the cuvettes include a dried reagent.

In one embodiment, the dried reagent is for amplification, and can include an enzyme.

In one embodiment, the cuvettes include a set of primers.

In one embodiment, the dried reagent in the cuvette is cover by a film of heat sensitive or phase-change material having a lower density than water.

In one embodiment, the heat sensitive material is a wax.

In one embodiment, the cuvette is adapted to be optically queried for at least one parameter.

In one embodiment, the cuvette has a cuvette body with at least one optically transparent window in the cuvette body, the optically transparent windows being aligned with a light path of a light source adapted to project light of a predetermined wavelength along the light path.

In one embodiment, the parameter is one of fluorescence, absorbance, and colorimetry.

In one embodiment, the parameter is fluorescence and wherein cuvette includes one of a fluorescing solution in the cuvette, fluorophore covered particles in a solution in the cuvette, fluorophore particles on an inner wall of the cuvette.

In one embodiment, the cuvette is a detection chamber.

In one embodiment, the cuvette is an amplification chamber.

In one embodiment, the cuvette is a nucleic acid amplification chamber.

In one embodiment, the transversal distribution channel includes a waste chamber at a second transversal end of the distribution channel.

In one embodiment, the waste chamber includes a heat-activated seal adapted to seal entry of the cuvette coupled to the distribution channel.

In one embodiment, the heat-activated seal is a wax.

In one embodiment, at least one of the chamber inlet, the surplus outlet, the exit outlet, the distribution outlet including an anti-backflow valve.

In one embodiment, at least one of the chamber inlet, the surplus outlet, the exit outlet, the distribution outlet including a burst valve, the burst valve opening at a predetermined centripetal force applied on the apparatus.

In one embodiment, the anti-backflow valve and the burst valve is provided in a single anti-backflow burst valve.

In one embodiment, the fluidic component layer is made of a plastic material.

In one embodiment, the plastic material is one of polycarbonate, polypropylene, PDMS, COC, SU-8 material.

In one embodiment, the fluidic component layer is sealed on the substantially flat back side with a sheet of plastic material.

In one embodiment, the sheet of plastic material is one of polycarbonate, polypropylene, PDMS, COC, SU-8 material.

In one embodiment, the fluidic component layer is sealed with the sheet of plastic material via bonding methods such as adhesive, pressure sensitive adhesive material, heat transfer, solvent bonding, uv-curable adhesive, ultrasound bonding, laser welding, RF bonding.

In one embodiment, burst valves burst characteristic is a combination of its distance from the center of rotation, the plastic material constituting the support plate, the material constituting the sealing and the geometry of the valve itself molded into the plastic material.

In one embodiment, the distribution channel, the cuvettes and the waste chamber are provided on a portion of the support member plate which extends beyond the outer edge of the rotatable holder.

In one embodiment, the fluidic component layer is rectangular.

In one embodiment, the holder is a disk.

In one embodiment, the shape of the fluidic component layer is a tapered section of a ring.

In one embodiment, the tapered section of a ring is a fraction of a ring.

In one embodiment, the tapered section of a ring is one eighth of a ring.

In one embodiment, the apparatus further comprises vent outlets for at least one of the overflow chamber, the retention chamber and the distribution channel, the vent outlets being connected to a self-venting channel.

In one embodiment, the self-venting channel is coupled to the sample intake receptacle at an inner side of the sample intake receptacle.

In one embodiment, the fluidic component layer is adapted to be at least partly heated.

In one embodiment, the fluidic component layer is adapted to be temperature-controlled.

In one embodiment, the fluidic component layer is adapted to be divided in at least two distinct temperature-controllable sections.

In one embodiment, a first of the two distinct temperature controllable sections includes the bottom-fillable chamber and the retention chamber.

In one embodiment, a first of the two distinct temperature controllable sections includes at least the retention chamber.

In one embodiment, the first section includes the sample intake receptacle, the entry channel, the overflow chamber and the metering channel.

In one embodiment, a second of the two distinct temperature controllable sections includes at least the distribution channel and the cuvettes.

In one embodiment, the second of the two sections includes the overflow chamber and a portion of the transfer channel.

In one embodiment, the fluid sample is at least one of blood, nasal pharyngeal aspiration, oral fluid, liquid from resuspended oral swab, liquid from resuspended nasal swab, liquid resuspended from anal swab, liquid resuspended from vaginal swab, saliva, urine (pure or diluted).

According to a broad aspect, there is provided a test apparatus using a fluidic centripetal device for testing components of a biological material in a fluid sample, the apparatus comprising at least one of the fluidic centripetal device; a rotor assembly; a holder for receiving the at least one of the fluidic centripetal device using the fluidic component layer, the holder being coupled to the rotor; a motor for rotating the rotor assembly; a speed controller for the motor for controlling at least one of a duration, acceleration and a speed of rotation of the rotor assembly; a temperature conditioning sub-system for controlling a temperature of at least a portion of the micro-fluidic centripetal device; an excitation sub-system for exciting the sample of the fluidic centripetal device and obtaining a test result; a user interface for receiving a user command and for sending a command to at least one of the speed controller, the temperature conditioning sub-system and the excitation sub-system.

In one embodiment, the holder is a rotor assembly comprising a bottom part of a rotor receiving the fluidic centripetal device and a snap ring to fix the fluidic centripetal device.

In one embodiment, the test apparatus further comprises an enclosure for the test apparatus having a base, walls and a hinged lid, the enclosure enclosing the rotor assembly, the holder, the motor, the temperature conditioning sub-system and the excitation sub-system.

In one embodiment, the test apparatus further comprises permanent magnets provided under the rotor.

In one embodiment, the temperature conditioning sub-system controls a temperature of two zones of the fluidic centripetal device.

In one embodiment, the test apparatus further comprises compartments created by at least one of the enclosure, enclosure separation wall, rotor assembly, rotor insulation wall, holder, lid insulation and the lid insulation wall.

In one embodiment, the test apparatus further comprises insulating materials that can be used to control the heat transfer between compartments.

In one embodiment, the temperature conditioning sub-system comprises a thermal element located one of above and under a heating zone.

In one embodiment, the thermal element is a resistive heating coil.

In one embodiment, the test apparatus further comprises a thermocouple inside each heating zone to measure individual temperature of each zone.

In one embodiment, the test apparatus further comprises a blower which forces room temperature air to enter in the heating zone.

In one embodiment, the test apparatus further comprises an outlet gate to eject hot air outside the heating zone.

In one embodiment, the excitation sub-system includes a light source, and optical elements to shape an excitation beam.

In one embodiment, the excitation sub-system includes a detection module to collect light emitted by species of interest within the fluidic centripetal device.

According to a broad aspect, there is provided a testing method using a fluidic centripetal device for testing components of a biological material in a fluid sample, the method comprising providing at least one of the fluidic centripetal device; providing a test apparatus; providing a fluid sample with biological material; loading the fluid sample in the sample intake receptacle of the fluidic centripetal device; placing the fluidic centripetal device in the holder of the test apparatus; providing a user command to commence a test sequence; rotating the rotor assembly at a first speed to transfer the fluid sample from the sample intake receptacle to the bottom-fillable chamber.

In one embodiment, the rotation further includes evacuating part of the sample into the overflow chamber.

In one embodiment, the testing method further comprises rotating the rotor assembly at a second speed to activate movement of the translocating member inside the bottom-fillable chamber.

In one embodiment, the testing method further comprises rotating the rotor assembly at a third speed to clarify the sample and burst the metering outlet, wherein a metered volume of the sample transfers to the retention chamber.

In one embodiment, the metered volume transfers to the receptacle of the retention chamber.

In one embodiment, the testing method further comprises rotating the rotor assembly at a fourth speed.

In one embodiment, the testing method further comprises heating the retention chamber, thereby releasing the liquid reactant from the container.

In one embodiment, the testing method further comprises rotating the rotor assembly at a fifth speed to burst the retention chamber outlet.

In one embodiment, the testing method further comprises keeping the cuvettes at a temperature below 65° C.

In an example embodiment, the testing method further comprises keeping the cuvettes at a temperature below 35° C.

In one embodiment, the testing method further comprises heating the cuvettes at a first temperature.

In one embodiment, the testing method further comprises heating the cuvettes at a second temperature.

In one embodiment, the testing method further comprises cycling temperature of the cuvettes between a high, a low and a medium test temperature.

In one embodiment, the testing method further comprises taking fluorescence measurement at least one excitation wavelength at the end of each cycle of temperature.

In one embodiment, the testing method further comprises logging fluorescence measurements.

According to a broad aspect, there is provided a testing method using a fluidic centripetal device for testing components of a biological material in a fluid sample, the method comprising providing at least one of the fluidic centripetal device; providing a test apparatus; providing a fluid sample with biological material; loading the fluid sample in the sample intake receptacle of the fluidic centripetal device; placing the fluidic centripetal device in the holder of the test apparatus; providing a user command to commence a test sequence; rotate the rotor assembly at a first speed to transfer the fluid sample from the sample intake receptacle to the retention chamber; heating the retention chamber, thereby releasing the liquid reactant from the container.

In one embodiment, the method comprises rotating the rotor assembly at a fifth speed to burst the retention chamber outlet.

In one embodiment, the sample transfers to the receptacle of the retention chamber.

According to another broad aspect of the present invention, there is provided a fluidic centripetal apparatus for testing components of a biological material in a fluid. The fluidic centripetal device is adapted to be received within a rotatable holder. The apparatus comprises a fluidic component layer having fluidic features on at least a front face and a bottom component layer bonded to a rear of the fluidic component layer thereby creating a fluidic network through which the fluid flows under centripetal force. A test apparatus and a testing method using a fluidic centripetal device for testing components of a biological material in a fluid are also provided.

In one embodiment, the fluidic feature may be a bottom-fillable chamber coupled to an entry channel for receiving the fluid, the chamber inlet being provided at an outer side of the bottom-fillable chamber.

In another embodiment, the fluidic feature may be a retention chamber coupled to an entry channel for receiving the fluid, a container wholly provided in the retention chamber and containing a liquid diluent, the container maintaining the liquid diluent in the container until it releases it in the retention chamber upon application of an external force to the container, thereby restoring the fluidic connection between the liquid diluent and the fluid in the retention chamber.

Additionally, the retention chamber can have a flow decoupling receptacle for receiving the fluid, located at the outer side of the retention chamber and interrupting a fluidic connection between the entry and exit of the retention chamber.

According to another broad aspect of the present invention, there is provided a fluidic centripetal apparatus for testing components of a biological material in a fluid, the fluidic centripetal device having a shape adapted to be received within a rotatable holder, the rotatable holder having a center of rotation and an outer edge, the fluidic centripetal device extending radially between the center of rotation and the outer edge, an inner side of the fluidic centripetal device being located towards the center of rotation and an outer side of the fluidic centripetal device being located towards the outer edge, the apparatus comprising: a fluidic component layer having fluidic features on at least a front face, the fluidic features including an entry channel for circulating the fluid, the entry channel being coupled to a chamber inlet; a bottom-fillable chamber coupled to the entry channel at the chamber inlet for receiving the fluid, the chamber inlet being provided at an outer side of the bottom-fillable chamber; and a bottom component layer bonded to a rear of the fluidic component layer thereby creating a fluidic network through which the fluid flows under centripetal force.

In one embodiment, the fluidic centripetal apparatus further comprises a intake receptacle for receiving the fluid, the intake receptacle extending outwardly from the fluidic component layer on a front face of the fluidic component layer and being located near the inner side, the intake receptacle ending in a intake receptacle outlet, the entry channel being coupled to the intake receptacle outlet at an end opposed to the chamber inlet.

In one embodiment, the bottom-fillable chamber includes at least one translocatable member that translocates within the bottom-fillable chamber in response to an external fluctuating magnetic field.

In one embodiment, the bottom-fillable chamber comprises at least one object irresponsive to a fluctuating magnetic field and wherein the object is at least one of a bead, a zeolite, a particle, a filtration particle, a glass bead, a zirconium bead, a resin, a bead and resin slurry.

In one embodiment, at least one of the object and the translocatable member is coated with at least one of a chelating and a ligant material adapted to interact with components of the fluid.

In one embodiment, the fluidic centripetal apparatus further comprises an overflow chamber coupled to a surplus outlet for the bottom-fillable chamber, the surplus outlet allowing exit of part of the fluid from the bottom-fillable chamber to the overflow chamber, wherein the surplus outlet is provided near the inner side of the bottom-fillable chamber on a longitudinal side of the bottom-fillable chamber.

In one embodiment, the fluidic centripetal apparatus further comprises an exit outlet for the bottom-fillable chamber, the exit outlet allowing exit of the fluid from the bottom-fillable chamber, wherein the exit outlet is located on the one longitudinal side of the bottom-fillable chamber, the exit outlet being located closer to the outer side of the bottom-fillable chamber than the surplus outlet, a metering volume of the bottom-fillable chamber being defined between the exit outlet and the surplus outlet.

In one embodiment, the fluidic centripetal apparatus further comprises exit outlet for the bottom-fillable chamber, the exit outlet allowing exit of the fluid from the bottom-fillable chamber, wherein the exit outlet is located on one longitudinal side of the bottom-fillable chamber.

In one embodiment, the fluidic centripetal apparatus further comprises a burst valve at the exit outlet, the burst valve opening at a predetermined centripetal force applied on the apparatus, the burst valve preventing the fluid from exiting the bottom-fillable chamber until the opening.

In one embodiment, the fluidic centripetal apparatus further comprises a retention chamber, the retention chamber being coupled to the exit outlet at an inner side of the retention chamber, the retention chamber being located closer to the outer side of the fluidic component layer than the bottom-fillable chamber, wherein the retention chamber is coupled to the exit outlet via a metering channel, the metering channel for circulating at least a portion of the fluid from the bottom-fillable chamber to the retention chamber.

In one embodiment, the fluidic centripetal apparatus further comprises a container wholly provided in the retention chamber and containing a liquid diluent, the container being adapted to maintain the liquid diluent in the container and to release the liquid diluent in the retention chamber upon application of an external force to the container, wherein the external force is one of mechanical, electrical, electromagnetic, heat, shock and acoustic force, thereby restoring the fluidic connection between the liquid diluent and the fluid in the retention chamber.

A fluidic centripetal apparatus for testing components of a biological material in a fluid, the fluidic centripetal device having a shape adapted to be received within a rotatable holder, the rotatable holder having a center of rotation and an outer edge, the fluidic centripetal device extending radially between the center of rotation and the outer edge, an inner side of the fluidic centripetal device being located towards the center of rotation and an outer side of the fluidic centripetal device being located towards the outer edge, the apparatus comprising: a fluidic component layer having fluidic features on at least a front face, the fluidic features including an entry channel for circulating the fluid, the entry channel being coupled to an intake receptacle outlet; a retention chamber, the retention chamber being coupled to the entry channel via the intake receptacle outlet for receiving the fluid into the retention chamber; a container wholly provided in the retention chamber and containing a liquid diluent, the container being adapted to maintain the liquid diluent in the container and to release the liquid diluent in the retention chamber upon application of an external force to the container, wherein the external force is one of mechanical, electrical, electromagnetic, heat, shock and acoustic force, thereby restoring the fluidic connection between the liquid diluent and the fluid in the retention chamber; and a bottom component layer bonded to a rear of the fluidic component layer thereby creating a fluidic network through which the fluid flows under centripetal force.

In one embodiment, the retention chamber has a flow decoupling receptacle for receiving the fluid, wherein the flow decoupling receptacle is located at the outer side of the retention chamber, the flow decoupling receptacle interrupting a fluidic connection between the intake receptacle outlet and a distribution outlet of the retention chamber.

In one embodiment, the flow decoupling receptacle includes a dried reactant.

In one embodiment, the retention chamber has a distribution outlet for the retention chamber, the distribution outlet being located at an outer side of the retention chamber, the distribution outlet being coupled to a transversal distribution channel at an inner side of the transversal distribution channel at a first transversal end of the distribution channel, the transversal distribution channel having a series of at least one cuvette provided at an outer side of the transversal distribution channel.

In one embodiment, at least one of the cuvettes includes at least one of a dried reagent and a phase-change material.

In one embodiment, the cuvette is adapted to be optically queried for at least one parameter; the parameter is one of fluorescence, absorbance, and colorimetry.

In one embodiment, the transversal distribution channel includes a waste chamber at a second transversal end of the distribution channel.

In one embodiment, the waste chamber includes a phase-change material.

In one embodiment, the distribution channel, the cuvettes and the waste chamber are provided on a portion of the fluidic layer component which extends beyond the outer edge of the rotatable holder.

In one embodiment, the fluidic component layer is adapted to be divided in at least two distinct temperature-controllable sections, wherein a first of the two distinct temperature controllable sections includes at least the retention chamber and a second of the two distinct temperature controllable sections includes at least the distribution channel and the cuvettes.

A fluidic centripetal apparatus for testing components of a biological material in a fluid, the fluidic centripetal device having a shape adapted to be received within a rotatable holder, the rotatable holder having a center of rotation and an outer edge, the fluidic centripetal device extending radially between the center of rotation and the outer edge, an inner side of the fluidic centripetal device being located towards the center of rotation and an outer side of the fluidic centripetal device being located towards the outer edge, the apparatus comprising: a fluidic component layer having fluidic features on at least a front face, the fluidic features including an intake receptacle for receiving the fluid, the intake receptacle extending outwardly from the fluidic component layer on a front face of the fluidic component layer and being located near the inner side, the intake receptacle ending in a intake receptacle outlet; an entry channel for circulating the fluid, the entry channel being coupled to the intake receptacle outlet at one end and to a chamber inlet at another end; a bottom-fillable chamber coupled to the entry channel at the chamber inlet for receiving the fluid, the chamber inlet being provided at an outer side of the bottom-fillable chamber; and a retention chamber, the retention chamber being coupled to the bottom-fillable chamber for receiving the fluid into the retention chamber; a distribution outlet for the retention chamber, the distribution outlet being located at an outer side of the retention chamber; a transversal distribution channel having a series of at least one cuvette provided at an outer side of the transversal distribution channel, the distribution outlet being coupled to the transversal distribution channel at an inner side of the transversal distribution channel at a first transversal end of the distribution channel, a waste chamber at a second transversal end of the distribution channel; and a bottom component layer bonded to a rear of the fluidic component layer thereby creating a fluidic network through which the fluid flows under centripetal force.

A test apparatus using a fluidic centripetal device for testing components of a biological material in a fluid, the apparatus comprising: at least one of the fluidic centripetal device; a rotor assembly; a holder for receiving the at least one of the fluidic centripetal device using the fluidic component layer, the holder being coupled to the rotor; a motor for rotating the rotor assembly; a speed controller for the motor for controlling at least one of a duration and a speed of rotation of the rotor assembly; a temperature conditioning sub-system for controlling a temperature of at least a portion of the micro-fluidic centripetal device; a detection sub-system for detecting a characteristic of the fluid; a user interface for receiving a user command and for sending a command to at least one of the speed controller, the temperature conditioning sub-system, the excitation sub-system and the detection sub-system.

In one embodiment, the temperature conditioning sub-system controls a temperature of at least two zones of the fluidic centripetal device.

A testing method using a fluidic centripetal device for testing components of a biological material in a fluid, the method comprising: providing at least one of the fluidic centripetal device; providing a test apparatus; providing a fluid with biological material; loading the fluid in the intake receptacle of the fluidic centripetal device; placing the fluidic centripetal device in the holder of the test apparatus; providing a user command to commence a test sequence; rotate the rotor assembly at a first speed to transfer the fluid from the intake receptacle to the bottom-fillable chamber.

DEFINITIONS

In this specification, the term "fluidic centripetal device" is intended to mean a fluidic network with fluid motivated by the action of the rotation.

In this specification, the term "Macro" in the expressions "Macro Structure" and "Macro Geometry" is intended to mean a fluidic centripetal device feature larger than 1 mm. In particular, "Macro Structure" dimensions are, for example, from about 1 mm to about 10 mm.

In this specification, the term "Micro" in the expressions "Micro Structure" and "Micro Geometry" is intended to mean a fluidic centripetal device feature smaller than 1 mm. In particular, "Micro Structure" dimensions about 1 μm to about 1 mm.

In this specification, the term "Sample", is intended to mean any fluid, solution or mixture suspension to be analyzed. In particular "sample" may be a "biological" sample or "raw biological sample" and is intended to mean any biological species of interest from blood, blood component, nasal and or pharyngeal and or oral bodily fluid, liquid from resuspended nasal and or oral and or pharyngeal swab, liquid resuspended from anal/vaginal swab, saliva, wound exudate, feces, and urine.

In this specification, the term "Diluent" is intended to mean a determined amount of fluid which may serve to dilute a sample.

In this specification, the term "Receptacle" is intended to mean a fluidic centripetal device feature designed to receive a certain amount of fluid.

In this specification, the term "Channel" is intended to mean a microstructure or macrostructure path of a fluidic centripetal device allowing fluid flow between fluidic centripetal device chambers, receptacles, and sample receptacles.

In this specification, the term "Inlet" is intended to mean an opening to a fluidic centripetal device chamber allowing fluid to enter.

In this specification, the term "Outlet" is intended to mean an opening to a fluidic centripetal device chamber allowing fluid to exit.

In this specification, the term "burst valve" or "fluidic valve" are used interchangeably and are intended to mean a microstructure on a fluidic centripetal device which has the main function of helping to prevent the liquid from flowing below a certain amount of pressure applied on the liquid, typically by centripetal force created by rotation of the fluidic centripetal device. The fluid flow through the "burst valve" when the pressure overcome the force produce by the surface tension of the liquid.

BRIEF DESCRIPTION OF THE DRAWINGS

Having thus generally described the nature of the invention, reference will be made to the accompanying drawings, showing by way of illustration example embodiments thereof and in which:

FIG. 1C depicts an oblique view of a fluidic centripetal device; FIG. 1D is a section view of a fluidic centripetal device;

FIG. 2A illustrates a fluidic vent connected to the intake receptacle; FIG. 2B illustrates a cap for the intake receptacle described in FIG. 2A;

FIG. 3A illustrates the fluidic construction of a bottom-filling chamber; FIG. 3B illustrates an alternative construction of the bottom-filling chamber with a port connection;

FIG. 7B illustrates an alternative construction of the bottom-filling chamber including a translocatable member, dried reagents, filter, overflow chamber and a metering outlet; FIG. 7C illustrates the alternative construction of FIG. 7B after filter dissociation by a translocatable member;

FIG. 11A illustrates liquid container in a retention chamber receptacle before heating; FIG. 11B illustrates fluid contained in a retention chamber receptacle during the beginning of the heating process; FIG. 11C illustrates release of the liquid from the fluid container inside the retention chamber; FIG. 11D illustrates mixing of the lysate with the fluid released from the liquid container; FIG. 11E illustrates the translocation of the diluted lysate from the retention chamber toward chamber 513;

FIG. 14A depicts fluidic construction of detection cuvettes of a fluidic centripetal device; FIG. 14B illustrates an alternative construction of the detection cuvette with pre-stored dried reagents.

It will be noted that throughout the appended drawings, like features are identified by like reference numerals.

DETAILED DESCRIPTION

Fluidic Centripetal Device Structure Assembly

Figure 1A:
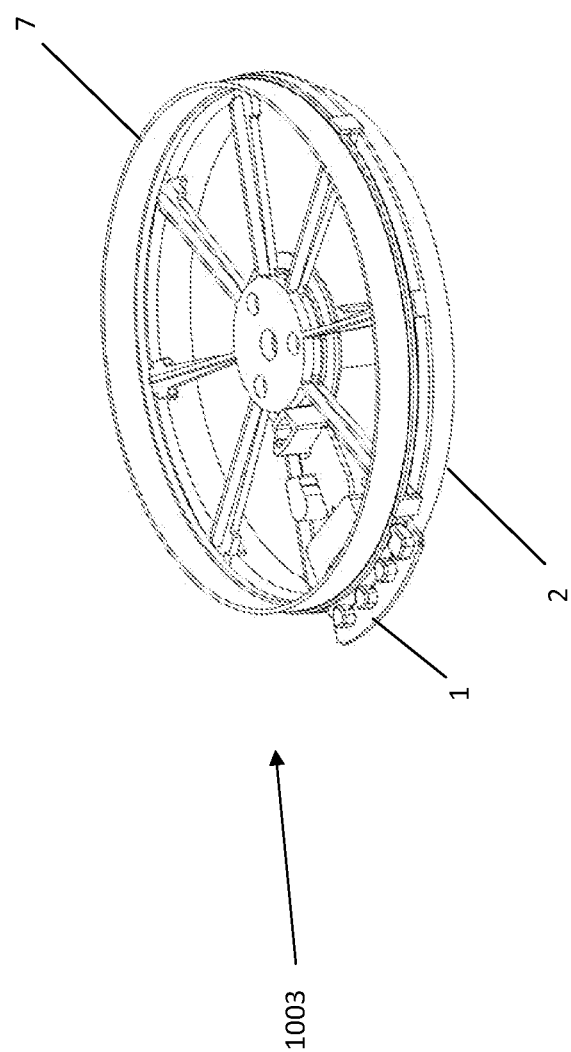
FIG. 1A is a perspective view of a rotor assembly holding a fluidic centripetal device.
Figure 1B:
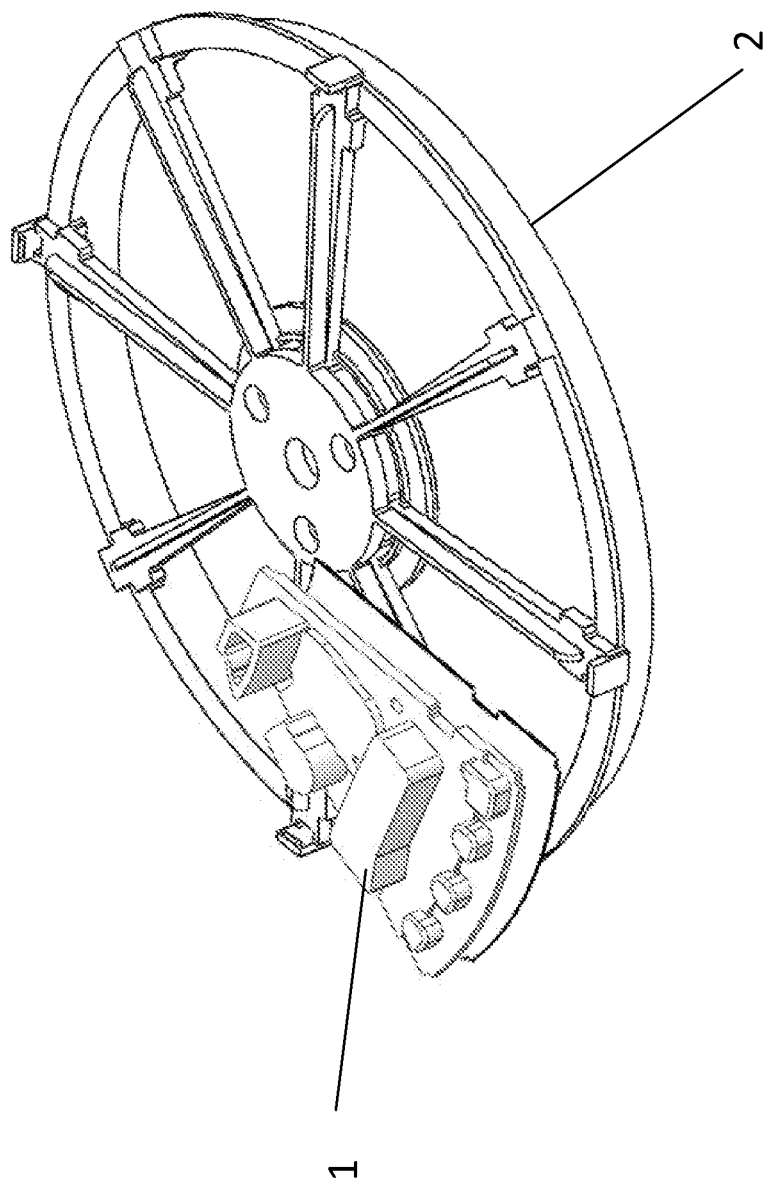
FIG. 1B depicts an exploded, oblique view of a fluidic centripetal device in a bottom part of a rotor.

FIG. 1A and FIG. 1B show an example rotor assembly 1003. An example bottom part of rotor 2 shaped to receive up to eight fluidic centripetal devices 1. Rotor assembly includes a bottom part rotor 2 and snap ring 7 to retain the fluidic centripetal device 1 inserted therebetween. The snap ring top rotor assembly body part was removed in FIG. 1B.

Fluidic centripetal device 1 is composed of at least two component layers. As shown in FIGS. 1C and 1D, a fluidic layer has features on the bottom face and/or the upper face of the fluidic centripetal device 1. The fluidic layer 3 is composed of intake receptacle 5, chambers 6a, 6b, 6c, channels and fluidic valves. It will be understood that the fluidic layer 3 can be made by using several layers bonded together. The thin bottom layer 4 is bonded to the fluidic layer 3. The bottom surface of the fluidic layer 3, when mated to the thin bottom layer 4, forms a fluidic network of enclosed reservoirs, channels and valves through which fluid flows under the centripetal force.

The fluidic layer 3 and thin bottom layer 4 can be made of thermoplastic material. The thermoplastic material may be at least one of cyclic olefin copolymer (COC), polycarbonate (PC), polystyrene (PS), polyoxymethylene (POM), perfluoralkoxy (PFA), polyvinylchloride (PVC), polypropylene (PP), polymethyl-methacrylate (PMMA), cyclic olefin copolymer (COC), polyamide (PA), polysulfone (PSU), polyvinylidene (PVDF) as well as other materials known to those skilled in the art. They may be used with unmodified surface or modified surface. The surface modification may be applied to one or both faces or on a specific region of interest on one or both faces.

Several mating techniques to assemble the fluidic centripetal device fluidic layer 3 with the flat bottom layer 4 are available such as thermal bonding, radio frequency bonding, laser welding, ultrasonic bonding, adhesion or pressure sensitive adhesion and other techniques known to those skilled in the art.

In an example embodiment, the mating technique allows to incorporate dried or liquids reagent within the fluidic centripetal device prior to assembly.

In another example embodiment, the mating technique is at a temperature from about 4° C. to about 80° C.

In one example embodiment, the rotation of the fluidic centripetal device is created by placing the fluidic centripetal device on a dedicated rotor 2, which is rotated about a center of rotation. The rotor 2 has a center of rotation and an outer edge, in this case, a circumference. The fluidic centripetal device 1 radially extends between the center of rotation and the outer edge. It even extends beyond the outer edge in the example shown. An inner side of the fluidic centripetal device 1 is located towards the center of rotation and an outer side of the fluidic centripetal device 1 is located towards the outer edge.

The fluidic centripetal device can be a portion of a disc having an internal diameter of about 5 mm and an external diameter from about 20 mm to about 50 mm. The portion of a disc can be ⅛ of a disc. There are no limitations to the shape of the fluidic centripetal device and to the number of fluidic centripetal devices a rotor can receive.

In an alternative embodiment, the fluidic centripetal device has a disc shape and the rotor is adapted to receive a single fluidic centripetal device.

In another alternative embodiment, the shape of the fluidic centripetal device corresponds to a standard microscope slide of 25 mm×75 mm. The rotor may be adapted to receive between 2 to 12 microscope slides.

Fluidic Layer

FIG. 1C illustrates the upper face structure of the fluidic layer 3 including the intake receptacle 5 for receiving a sample and several reservoirs 6a, 6b, 6c. The shape of each reservoir is adapted to requirements and functions implemented in the fluidic centripetal device 1.

FIG. 1D illustrates a section view of the fluidic layer 3 with the thin bottom layer 4. In an example embodiment, the design of fluidic layer 3 may be adapted to the injection molding process. It may be advantageous, for some applications, to respect a uniform wall thickness. For example, a wall thickness could be from about 0.7 to 1.2 mm. It may be advantageous, for some applications, to ensure a constant draft angle. The vertical faces can have a draft angle from about 0.5° to 5°.

Intake Receptacle, Vented Channels and Fluidic Centripetal Device Sample Inlet Cap FIGS. 2A and 2B illustrate an example embodiment of an intake receptacle. The intake receptacle 5 is fluidly connected to a chamber 901. The vented outlet 816 is connected to the outlet channel and vented chamber 905.

In one embodiment, the vented chamber 905 is connected to intake receptacle 5 with the inlet vent connection 906 on the upper face of the fluidic centripetal device near the inner portion of intake receptacle 5.

In an example embodiment, a cover 907 includes base piece 908 in direct contact with the intake receptacle 5, a flexible connecting arm 909, and a cap 910 linked to base piece 908 by connecting arm 909. Cover 907 can be placed in a closed configuration with the cap 910 secured on the base piece 908 or can be placed in an open configuration as shown in FIG. 2B. In this particular embodiment, base piece 908 is designed to allow communication between vented chamber 905 and chamber 901 via inlet vent connection 906 even when cover 907 is in closed configuration.

In an alternative embodiment (not illustrated), vented chamber 905 is disconnected from chamber 901 (inlet vent connection 906 is absent). The air venting is provided by a hole provided on base piece 908 of cover 907 which allows air communication between chamber 901 and vented chamber 905 via the free cavity formed between base piece 908 and cap 910 when cover 907 is in the closed configuration.

Bottom-Fillable Chamber

FIGS. 3A and 3B illustrate the bottom-fillable chamber of the fluidic network. In this example, the intake receptacle 5 is fluidly connected to the bottom-fillable chamber 315 with the entry channel 302. The connection between the intake receptacle and the entry channel may be optionally done via a port connection 303 or the outlet of the intake receptacle may be directly connected to the entry channel.

In one embodiment, specific solid phase chromatography material (such as ion exchange material) can be placed into the receptacle 5. During centrifugation to fill the bottom-fillable chamber, the solid phase chromatography material will fill the channel 302 enabling the formation of an exclusion column able to adsorb some nucleic acid amplification inhibitor from the crude sample.

The bottom inlet 304 of the bottom-fillable chamber 315 is located at the outer side of the bottom-fillable chamber 315. Since flow of the sample will be from the intake receptacle 5 to the outer side of the bottom-fillable chamber, the outer side of the bottom-fillable chamber is referred to as the bottom of the bottom-fillable chamber. A vent channel 305a is connected to the chamber outlet 306 at the inner side of the bottom-fillable chamber.

Dimension of the chamber is comprised between several centimeters in width, several centimeters in height and several millimeters in depth. In an example embodiment, the chamber 315 dimension is comprised between 1 cm wide, 2 cm high and 2 mm deep. In another example embodiment, the dimensions are 0.5 cm wide, 1.5 cm high and 1.3 mm deep.

Reagents and Translocatable Member

Figure 4B:
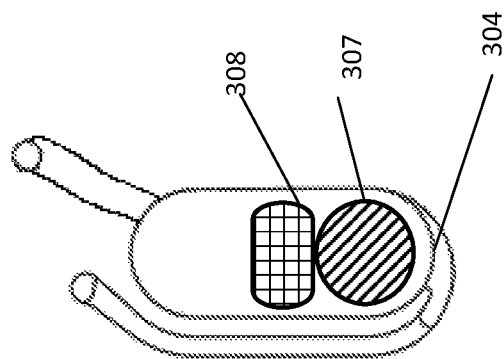
FIG. 4B illustrates an alternative construction of the bottom-filling chamber including a translocatable member and dried reagents.
Figure 4A:
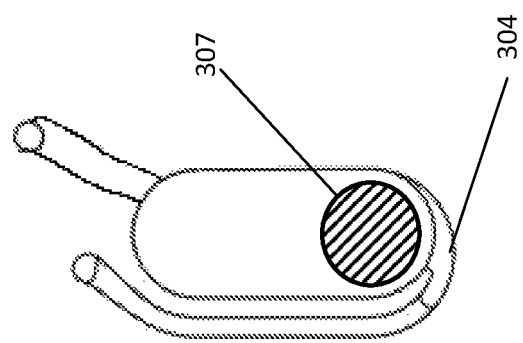
FIG. 4A illustrates an alternative construction of the bottom-filling chamber including a translocatable member.

Referring now to FIGS. 4A and 4B, the bottom-fillable chamber may optionally contain a translocatable member object 307. The translocatable member can be ferromagnetic and can move in the chamber in response to a fluctuating magnetic field. In an example embodiment, the fluctuation magnetic field is generated by the rotation of the fluidic centripetal device above fixed magnets placed alternatively in a radial position corresponding to the inner and the outer edges of the bottom-fillable chamber. In another embodiment, the fluctuation magnetic field is generated by the rotation of magnets above a fixed fluidic centripetal device.

In an example embodiment, fixed magnets are permanent magnets made of rare-earth magnetic material. In another embodiment, they are electromagnets.

The chamber may also optionally contain solid material 308 that does not respond to a magnetic field. The solid material can be used to provide a chemical or biochemical reaction and may include salt, buffer or enzyme. The solid material can be used to purify the sample by adsorbing enzymatic inhibitors and may include a chromatography matrix, a solid support for affinity binding, a solid phase extraction, a chelating material, anionic and cationic resins and different types of zeolite. The solid material can be used for cell breakage and may include hard matrix. The solid material can be used for process control and may include bacterial cells or spores. The solid material can be used to concentrate the lysate using hygrometric matrix to absorb liquids. The solid material can be functionalized with ligands such as specific antibodies and can be used to capture targets inside the bottom-fillable chamber. The solid material can be a filter able to stop or trap target microbes inside the bottom-fillable chamber. The solid material can be functionalized with ion exchange moieties able to adsorb target microbes at its surface, immobilizing them inside the bottom-fillable chamber. These different solid materials can be used alone or in combination.

When the solid materials are hard matrix for cell wall and membrane disruption, the material can be made of silica or zirconium beads with diameters from about 50 μm to about 200 μm. The beads can be optionally coated with chelating agent for absorption of the enzymatic inhibitors.

In one example embodiment, the translocatable object is a metallic disc and the solid material is composed of hard beads mixed with anionic and cationic resin and spores.

Overflow

Figure 5:
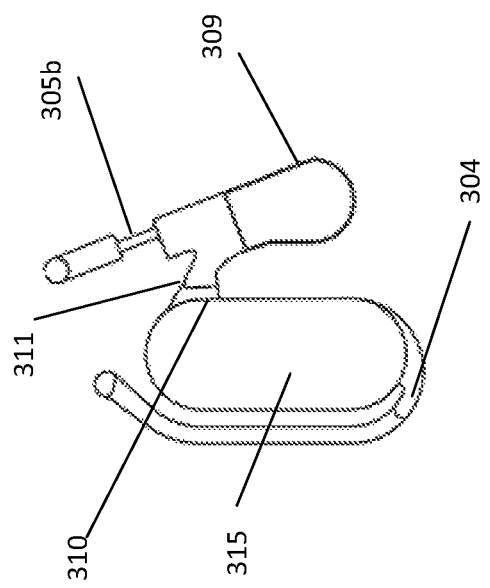
FIG. 5 illustrates an alternative construction of the bottom-filling chamber including an overflow chamber.

FIG. 5 illustrates another fluidic interconnection of the bottom-fillable chamber which includes an overflow chamber 309 fluidly connected to the overflow outlet 310 of the bottom-fillable chamber by the overflow channel 311. The overflow channel is placed near the inner portion of the chamber on one of the longitudinal sides of the chamber. The overflow chamber is located towards the outer edge of the fluidic centripetal device with respect to the overflow outlet 310 and the overflow chamber is vented through the vent channel 305b. This configuration allows making volume definition in the bottom-fillable chamber while simultaneously venting the bottom-fillable chamber and the overflow chamber 309. The volume of the overflow chamber is comprised between 100 μl and several milliliters. In an example embodiment, the volume of the overflow chamber is comprised between 150 to 200 μl.

Metering

Figure 6:
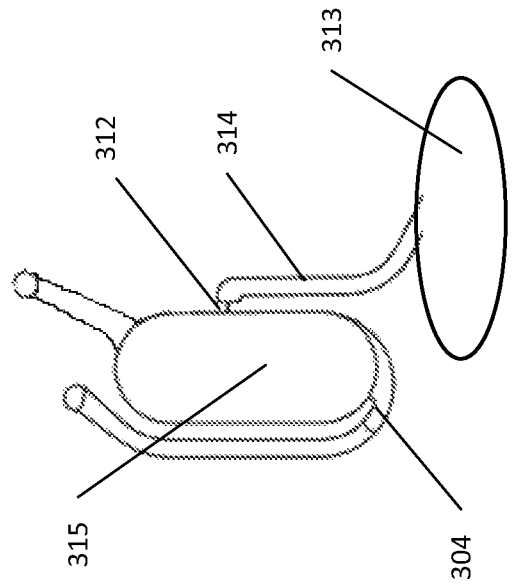
FIG. 6 illustrates an alternative construction of the bottom-filling chamber including a metering outlet.

FIG. 6 illustrates an optional exit outlet 312 to the bottom-fillable chamber to fluidly connect the bottom-fillable chamber to a subsequent chamber 313 with the transfer channel 314. The exit outlet is located on one of the longitudinal sides of the bottom-fillable chamber. The exit outlet can be a burst valve having micrometric dimension. The dimension of the micrometric valve can be from 1 to 100 μm deep, 10 μm to 1 mm wide and a few microns to a few millimeters long. In an example embodiment, the dimension of the micrometric valve is comprised between 30 to 75 μm deep, 70 to 120 μm wide and 0.5 to 1.5 mm long. The exit outlet can be placed at any distance between the inner and outer edges of the bottom-fillable chamber as long as the exit outlet is placed in an outer position with respect to the overflow outlet. The distance between the exit outlet and the overflow outlet will define the volume to be metered and sent to the next chamber.

The volume of fluid metered by the exit outlet can be comprised between 10 to and 50 μl. In an example embodiment, the volume defined is 20 μl.

Figure 7A:
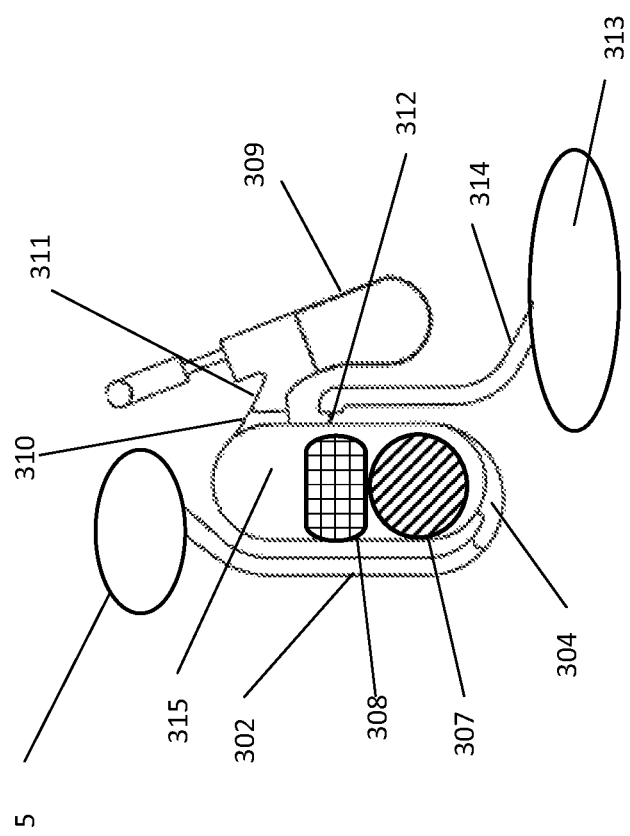
FIG. 7A illustrates an alternative construction of the bottom-filling chamber including a translocatable member, dried reagents, overflow chamber and a metering outlet.
Figure 8A:
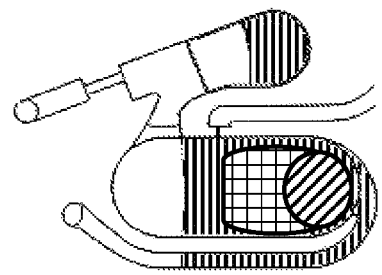
FIG. 8A illustrates the filling of the bottom-filling chamber shown in FIG. 7A.
Figure 8B:
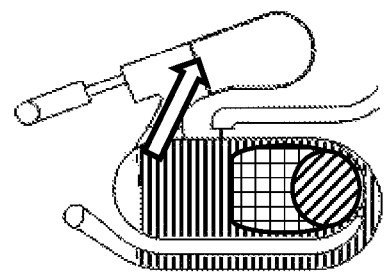
FIG. 8B illustrates the translocation of the liquid overflow toward the element 309.
Figure 8C:
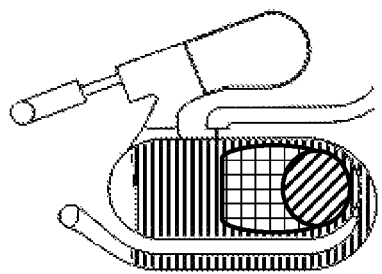
FIG. 8C illustrates the volume definition step.
Figure 8D:
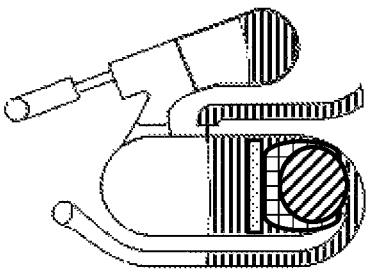
FIG. 8D illustrates the translocation of the translocatable element.
Figure 8E:
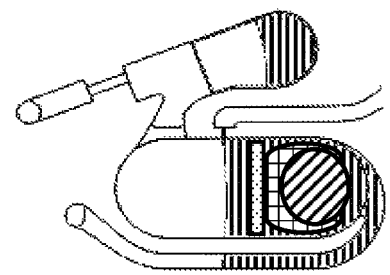
FIG. 8E illustrates the pelleting at the bottom of the bottom-filling chamber of elements 308 and 307.
Figure 8F:
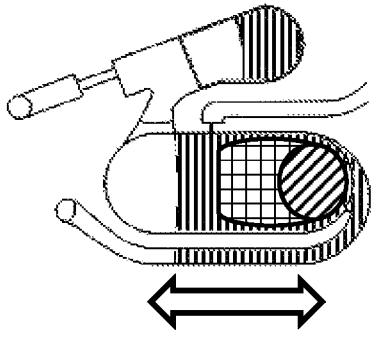
FIG. 8F illustrates the translocation of the metered volume from the bottom chamber to chamber 313.

FIG. 7A illustrates a bottom-fillable chamber having some of the optional configurations described above. The intake receptacle 5 is fluidly connected to entry channel 302, the bottom-fillable chamber 315 and the bottom inlet 304. An overflow chamber 309 is fluidly connected to the bottom-fillable chamber through the overflow outlet 310 and overflow channel 311. The exit outlet 312 allows transferring liquids located between the overflow outlet and the exit outlet to a subsequent chamber 313 through the outlet channel 312. The chamber contains translocatable member 307 and solid material 308.

FIG. 7B illustrates a bottom-fillable chamber with a target stopper 316. The stopper is placed in order to force the sample through it. Water and small molecule will go through but the target will be retained. Since the majority of the liquid loaded into the intake receptacle 5 will flow through the overflow 309 via the target stopper 316, the target will be concentrated into the small percentage of liquid present in the bottom-fillable chamber.

FIG. 7C shows the release of the trapped bacteria after the pathogen stopper is being dissociated by the translocatable movement of the translocatable member 307. The target can be at least one of cells, bacteria, fungi, virus, etc. In one embodiment, the target stopper 316 is a size exclusion filter. In another embodiment, the target stopper 316 is an ion exchange resin. In another embodiment, the pathogen stopper 316 includes beads functionalized with specific antibodies.

FIG. 8 illustrates the fluidic progression in the bottom-fillable chamber described in FIG. 7. FIG. 8A to FIG. 8F describe the sequential fluid movement in the bottom-fillable chamber. Filling of the chamber occurs in FIG. 8A, liquid overflow out to overflow chamber occurs in FIG. 8B and FIG. 8C, sample homogenization and lysis actuated by translocatable movement occurs in FIG. 8D, clarification by sedimentation of insoluble materials occurs in FIG. 8E and transfer of the metered liquid to the next chamber occurs in FIG. 8F.

Figure 9A:
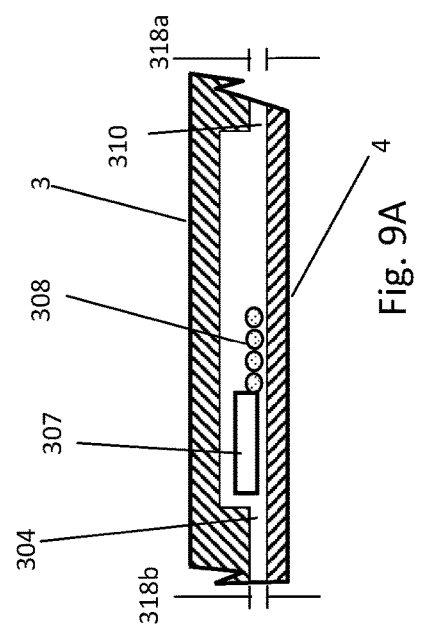
FIG. 9A illustrates a section view of the inlet and outlet geometry to help prevent the translocatable object and/or beads located in the solid phase material to exit from the bottom-filling chamber.
Figure 9B:
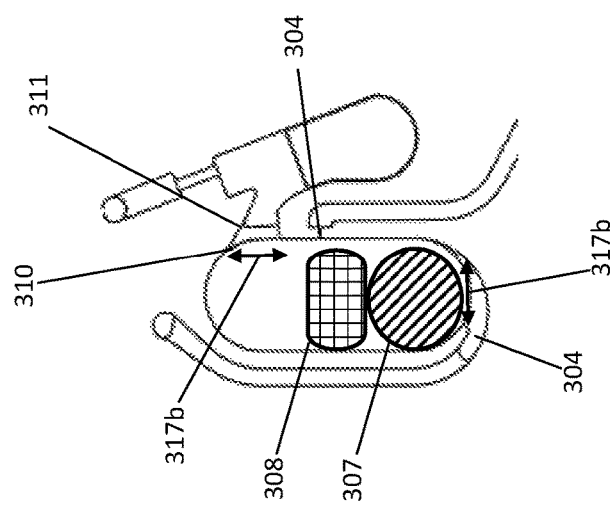
FIG. 9B illustrates a top view of the inlet and outlet geometry to help prevent the translocatable object and/or beads located in the solid phase material to exit from the bottom-filling chamber.

Referring now to FIG. 9A and FIG. 9B, the geometry of the bottom inlet 304 and the optional overflow outlet 310 and optional exit outlet 312 are adapted to help prevent the translocatable object and/or beads from exiting the bottom-fillable chamber. In one embodiment, the smallest dimension of the translocatable object and the beads contained in the solid material should be greater than width 317a or depth 318a and greater than width 317b or depth 318b.

Retention Chamber

One example embodiment of a fluidic structure to retain and/or dilute a sample is illustrated in FIGS. 10A to 10D. In this embodiment, a fluid entry channel 401 is fluidly connected to the inlet 402, located on the inner side of chamber 403. The vent outlet 404 is located on the inner side of the chamber to allow the air displacement in the chamber. The reservoir has a volume from about 1 μl to about 2 ml. The outlet 405 of the reservoir is located on the outer side of the chamber and is generally a burst valve.

Figure 10B:
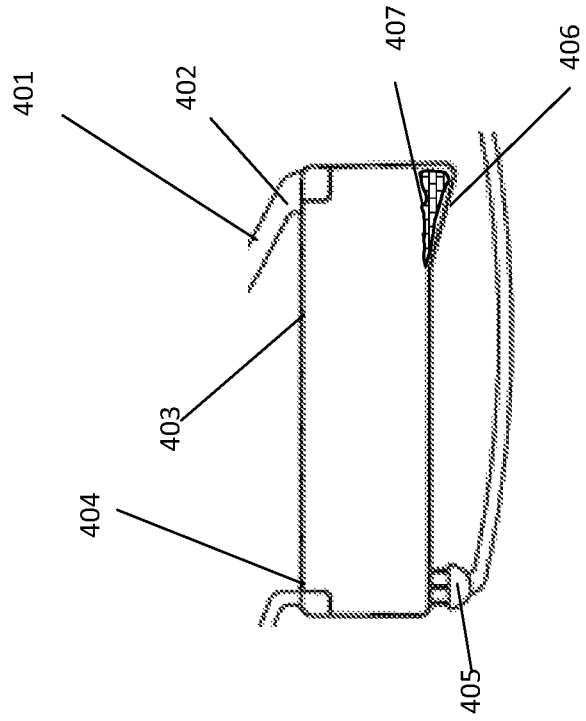
FIG. 10B illustrates fluid contained in a retention chamber receptacle.
Figure 10A:
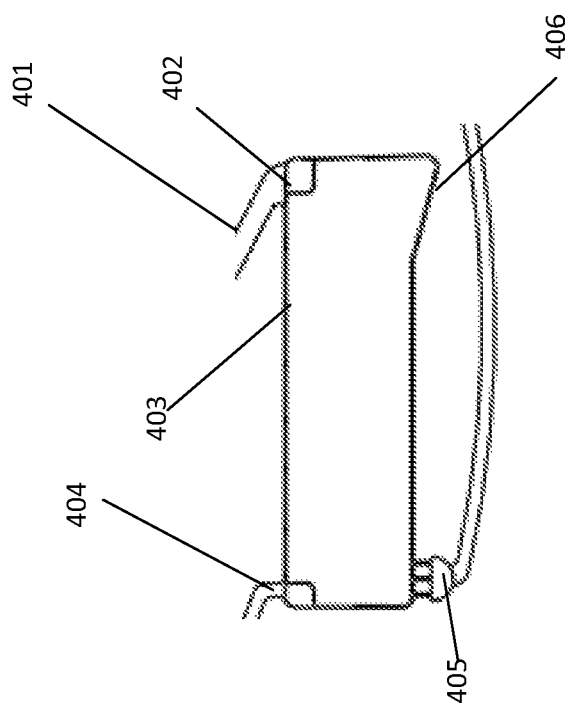
FIG. 10A illustrates a fluidic structure to mix or to dilute sample.

In the example embodiment of FIG. 10A, the retention chamber has an optional receptacle 406 located on the outer side of the chamber. The receptacle is generally adapted to contain liquid 407 coming from the inlet channel to help prevent the liquid from being in contact with the chamber outlet 405 upon initial entry into the retention chamber as shown in FIG. 10B.

Figure 10D:
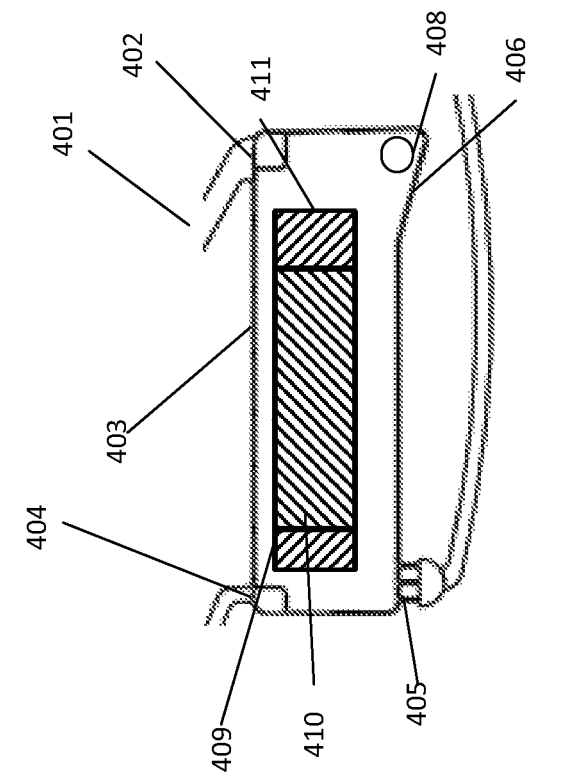
FIG. 10D illustrates a liquid container inside a retention chamber.
Figure 10C:
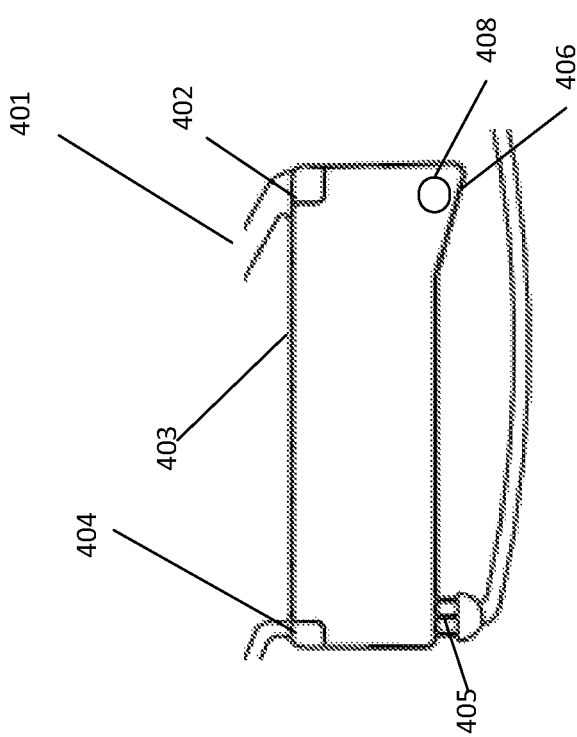
FIG. 10C illustrates dried reagents in the receptacle of a retention chamber.

Optionally, the receptacle may contain dried reagents 408 as shown in FIG. 10C. Dried reagents 408 can be, but are not restricted to, enzymes, buffer and/or chemicals.

In the example embodiment illustrated in FIG. 10D, the retention chamber may optionally include a liquid container 409 placed inside the retention chamber and containing a diluent 410. The diluent can be, but is not limited to, water, buffer or some part of buffer which cannot be dried. The liquid container 409 is generally, but not necessarily, made of a heat tolerant material and/or sensitive phase-change material. The heat tolerant material may have a melting point over 100° C. and may be one of glass, polymer thermoplastic as well as other materials known to those skilled in the art. The phase-change material may melt and solidify at a certain temperature. The solid phase may be below about 45° C. and the melt phase temperature may be between about 45° C. and 85° C. The phase-change material may be wax, paraffin wax, microcrystalline wax, synthetic wax, natural wax, glue or other sealing materials known to those skilled in the art.

The above described structures can be used as a novel valve type we call Flow Decoupling Valve. The Flow Decoupling Valve contains two elements, a flow decoupling receptacle to interrupt the fluidic connection between the inlet and outlet of a retention chamber, and a liquid container enclosing a diluent which can be released upon application of an external force. Release of the diluent restores fluidic connection within the circuit.

In an example embodiment, a phase-change material extremity 411 of the container 410 releases the liquid when the retention chamber is heated above a certain temperature. The liquid container can help prevent evaporation of the enclosed liquid for a period of about 1 to 3 years and has a capacity of one microliter to two milliliters.

FIG. 11 illustrates the fluidic progression of the sequential fluid movement in the retention chamber embodiment. Shown in FIG. 11A is the liquid 407 coming from the inlet which is in the receptacle, in FIG. 11B, the retention chamber is heated 416 and the phase-change material extremity is melting 411a, 411b, in FIG. 11C, the diluent 410 is released, in FIG. 11D, the liquid 407 coming from the inlet is mixed with the diluent 410, and in FIG. 11E, the diluted 415 is evacuated by the burst valve outlet 405.

Figure 12:
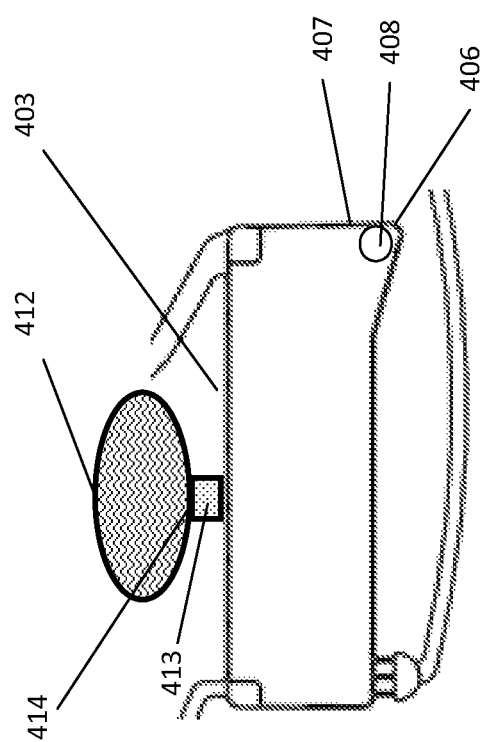
FIG. 12 illustrates an alternative construction of the liquid container.

An alternative example embodiment is illustrated in FIG. 12 to dilute a fluid in a retention chamber. A diluent chamber 412 may be located above or on the inner side of the retention chamber 403. The liquid is released in the retention chamber by activating a phase-changing material valve 413 placed at the diluent outlet 414. In this example embodiment, the phase-changing material valve is a wax valve activated by heat above about 50° C. In another embodiment, the heat is generated by electromagnetic wave such as infrared radiation, laser, microwaves and any other materials known to those skilled in the art. In an alternative embodiment (not illustrated), the liquid from the liquid container may be released mechanically. For example, a piercing mechanism can be activated by a plunger. In another alternative embodiment (not illustrated), the liquid from the diluent container may be released by an electromagnetic actuator.

Figure 13:
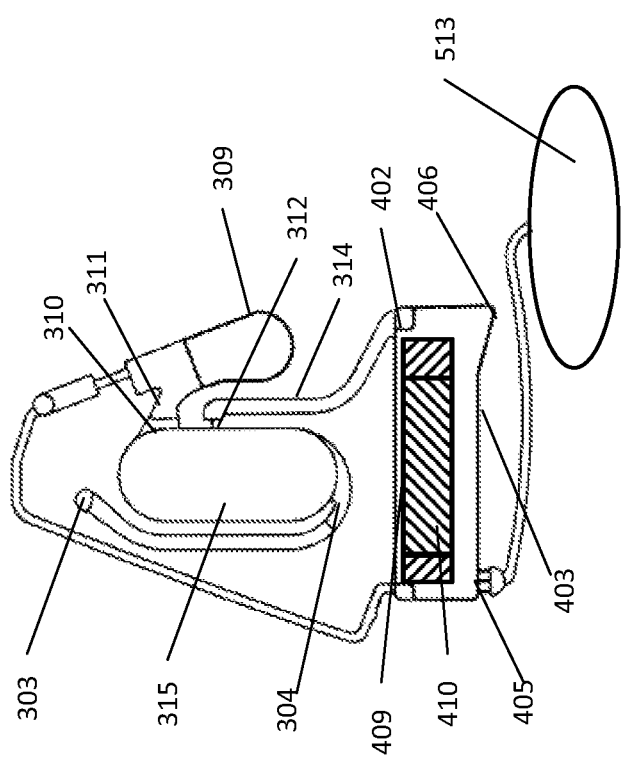
FIG. 13 depicts a fluidic construction including a bottom-filling chamber with overflow chamber and a metering outlet fluidly connected to a retention chamber.

An example embodiment of a fluid metering system connected to retention chamber is shown in FIG. 13. In this example, sample outlet 303 is fluidly connected to bottom-fillable chamber 315, through the bottom inlet 304. An overflow chamber 309 is connected to bottom-fillable chamber 315 with overflow outlet 310 and overflow channel 311. The metering outlet 312 allows transferring the liquid contained, between the overflow outlet 310 and the metering outlet 312 of chamber 315, to the retention chamber receptacle 406 via the metering channel 314 and retention chamber inlet 402.

Upon heating, the diluent 410 contained in the dilution container 409 is released into the retention chamber 403. The released liquid 410 mixes with the measured volume contained in the retention chamber receptacle 406. Once the diluent and the measured volume are mixed together, the total volume is large enough to bring the dilution in contact with outlet 405 acting as a burst valve. Thus, release of the liquid from container 409 brings a liquid in the right place at the right time and also reactivates the fluidic circuitry. Indeed, before the liquid container is heated, the liquid coming from chamber 315 is retained into the receptacle 406. In this particular embodiment, the retention chamber receptacle allows a high RPM burst rate for the metering outlet burst valve 312 and helps prevent the liquid from coming out of the retention chamber by controlling the localization of the fluid to help prevent contact with the retention chamber outlet valve 405. The mechanism of this novel Flow Decoupling Valve dissociates the passive metering outlet burst valve 312 from passive outlet valve 405, enabling a robust fluidic control without the need for complex active valving.

In another example embodiment, the phase change material 411 of the liquid container 409 has a density superior to the measured liquid 407 retained in the receptacle 406 and the diluent 410. When heated, the liquid 410 contained in the liquid container 409 is released into chamber 403. The phase change material 411 will move below the mixture of diluent 410 and fluid 407 and displace the latter so it can be in contact with outlet 405 which can act as a burst valve. In this particular embodiment, the retention chamber can be emptied once the higher density liquid is released.

In some embodiments, dried reagents 408 can be stored into the retention chamber 403.

Cuvette, Detection Chamber and Distribution Chamber

FIG. 14 illustrates an embodiment of an arrangement of fluidic detection cuvettes. In the example embodiment of FIG. 14A, a sample reservoir 601 is fluidly connected to one or more detection cuvette 602a, 602b and 602c through entry channel 603, distribution channel 604 and cuvettes inlets. In the example shown, the number of cuvettes is three. The end of the distribution channel 604 is fluidly connected to the waste chamber 605 and a vented outlet 606 is located near the end of distribution channel 604.

In an example embodiment of FIG. 14B, dried reagents 607a, 607b and 607c have been stored into respective cuvettes 602a, 602b, 602c. Dried reagents can be sets of primers, enzymes mixes, fluorescence probes and salts to perform enzymatic amplification process and/or detection. The fluid transferred in the cuvettes will resuspend dried reagents.

Figure 14C:
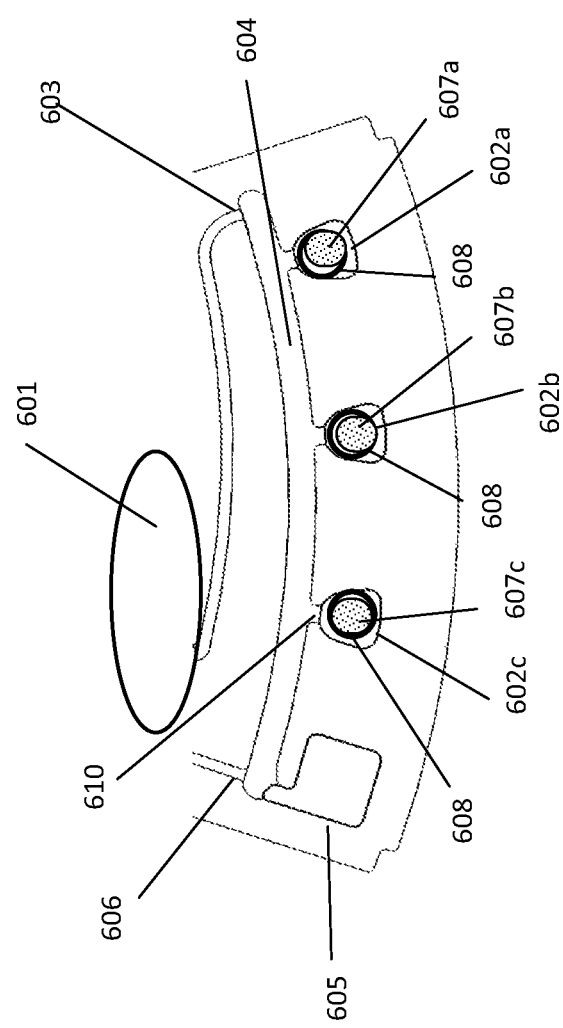
FIG. 14C illustrates an alternative construction of the detection cuvette with pre-stored dried reagents in the cuvettes and cuvette wax pre-stored in the cuvettes themselves.

In another embodiment shown in FIG. 14C, a heat sensitive phase-change material 608 can be placed directly inside each cuvette for example, on top of dried reagents 607. The heat sensitive phase-change material 608 can have a specific gravity lower than the incoming fluid specific gravity. For example, the melting point of material 608 is above 50° C. and has a specific gravity below one. In an example embodiment, the phase-change material is wax. In this embodiment, the volume of the cuvette minus the volume of the phase-change material defines the volume of the amplification reaction which is generally between 5 and 100 µl. Upon heating, the phase-change material will melt and under centripetal force will move up to the cuvette inlet 610. In this embodiment, a well designed cuvette inlet when filled with the phase-change material will help prevent evaporation and cross contamination between each cuvette.

Figure 14D:
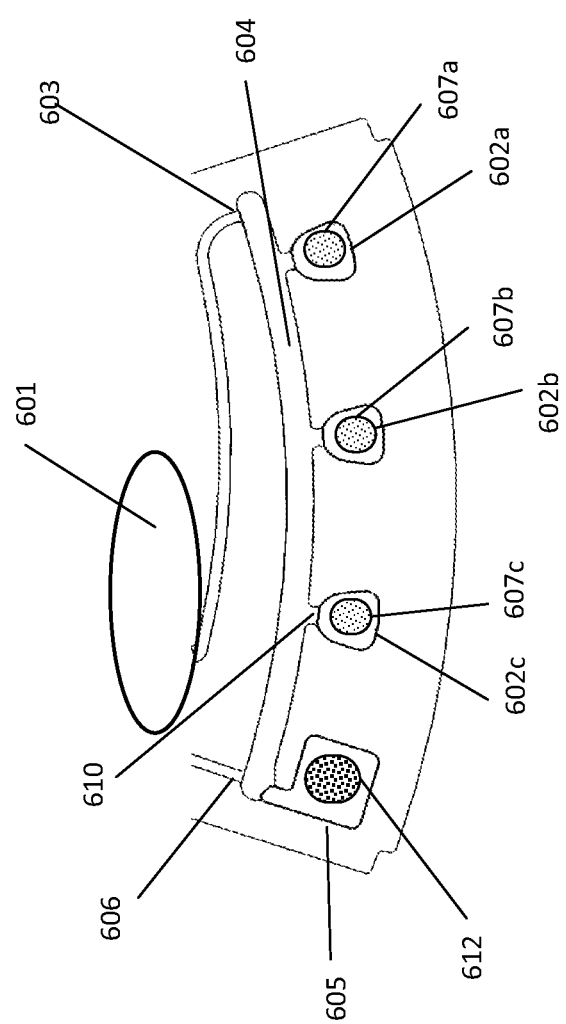
FIG. 14D illustrates an alternative construction of the detection cuvette with pre-stored dried reagents in the cuvettes and cuvette wax pre-stored in a waste chamber.
Figure 15:
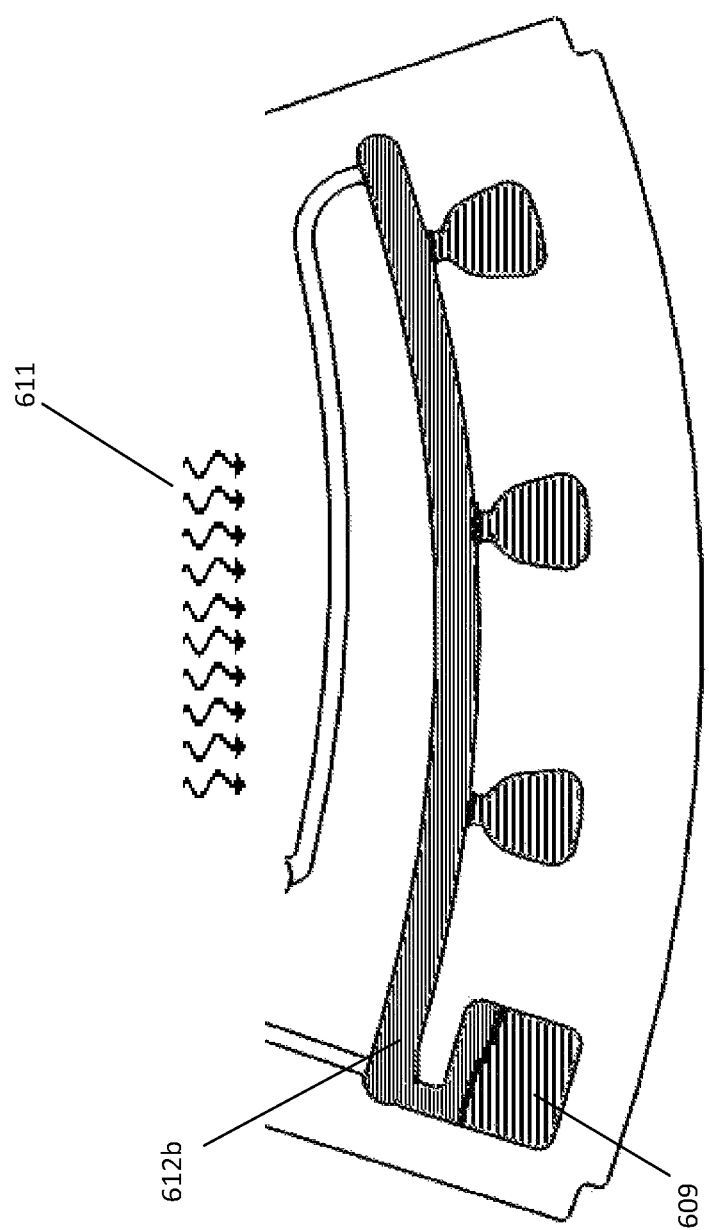
FIG. 15 illustrates the fluidic construction described in FIG. 14D when the cuvettes are heated and filled by a sample.

In another embodiment illustrated in FIG. 14D, the waste chamber may contain a heat sensitive phase-change material 612 with a specific gravity lower than the sample specific gravity. For example, the melting point of the material is above 50° C. and has a specific gravity below 1. In an example embodiment, the phase-change material is wax. As illustrated in FIG. 15, when the waste chamber 605, the distribution channel 604 and the cuvettes 602 are heated 611, and when a surplus of fluid 609 enters in the waste chamber 605, the melted wax 612b moves within the distribution channel 604 on top of the cuvette inlets.

In another embodiment, a phase-change material 612 is placed into the waste. The liquid coming from the retention chamber is brought to the distribution canal with a temperature inferior to the melting point of the phase-change material present in the waste.

In an embodiment, a phase-change material is placed both into the cuvettes and into the waste. In this particular embodiment the melting point of the phase-change material 612 placed into the waste is equal or lower than the melting point of the phase-change material 608 placed into the cuvettes.

Figure 16:
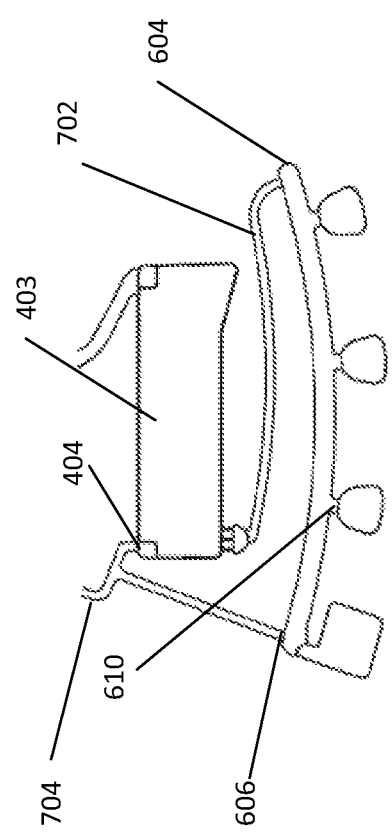
FIG. 16 depicts a fluidic construction including retention chamber and detection cuvettes.

FIG. 16 shows another example embodiment in which a retention chamber 403 as described above is fluidly connected to the distribution channel 604. In an embodiment, vent outlet 606 of the distribution channel and vent outlet 404 of the retention chamber may optionally be merged into a single vent channel 704 near the vent outlet 404 of the retention chamber 403.

Figure 17:
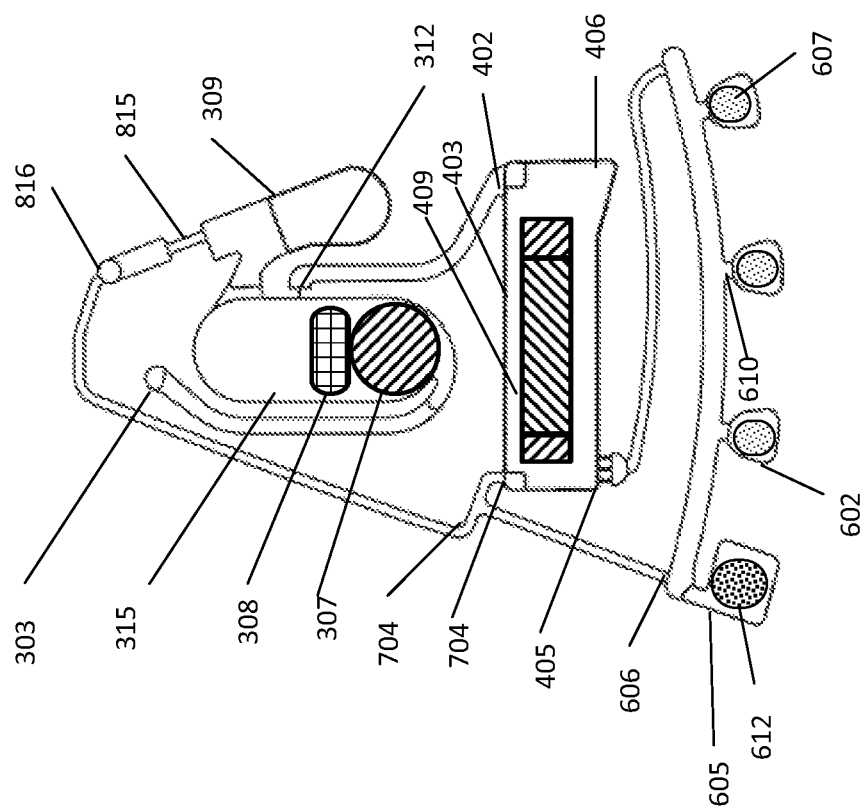
FIG. 17 depicts a fluidic construction for sample preparation and detection.

FIG. 17 shows another example embodiment in which a sample port 303 is fluidly connected to the bottom-fillable chamber 315, in which the chamber includes a translocatable member 307 and hard beads 308. The bottom-fillable chamber is connected to an overflow chamber 309 and a burst valve metering outlet 312 is fluidly connected to a retention chamber inlet 402. The retention chamber 403 contains a receptacle 406 and a liquid container 409 as described above to allow dilution of the fluid. The diluted fluid reaches the outlet 405 and is transferred to the cuvettes 602 through the burst valve outlet 405 of the retention chamber 403 and the waste 605 contains wax 612. In this example embodiment, dried reagents 607 and wax (not illustrated) are stored in the cuvettes. The vented outlet 606, 404 and 815 of the cuvettes, the retention chamber and the bottom-Tillable chamber are merged together to allow venting of the complete fluidic circuitry through a single venting port 816.

Exemplary Configuration of Instrument

Figure 18:
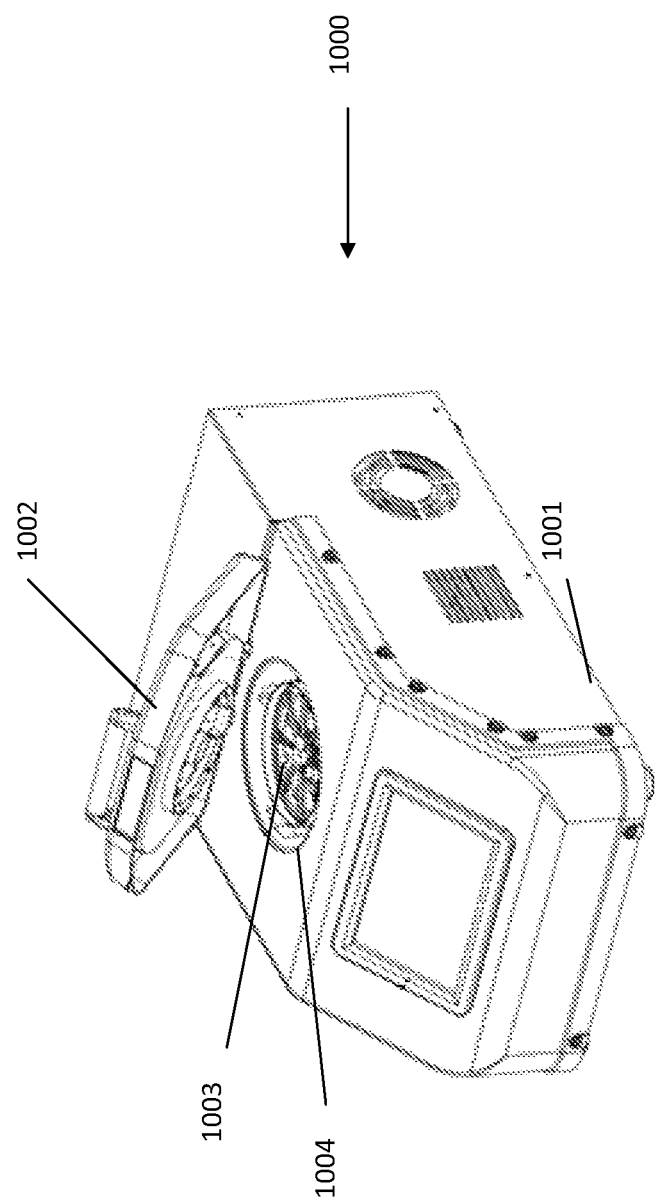
FIG. 18 depicts a perspective view of an instrument which may be used to carry out a number of simultaneous fluidic centripetal devices.

FIG. 18 illustrates an example instrument 1000 to process a fluidic centripetal device as presented above. The apparatus 1000 is, in this example embodiment, 30 cm wide×30 cm deep×20 cm high. It includes a base 1001, a hinge lid 1002 and a rotor assembly 1003 placed inside the centrifugation enclosure 1004. The rotor assembly 1003 placed inside the centrifugation enclosure 1004 revolves in a plane parallel to the base of the instrument.

Figure 19:
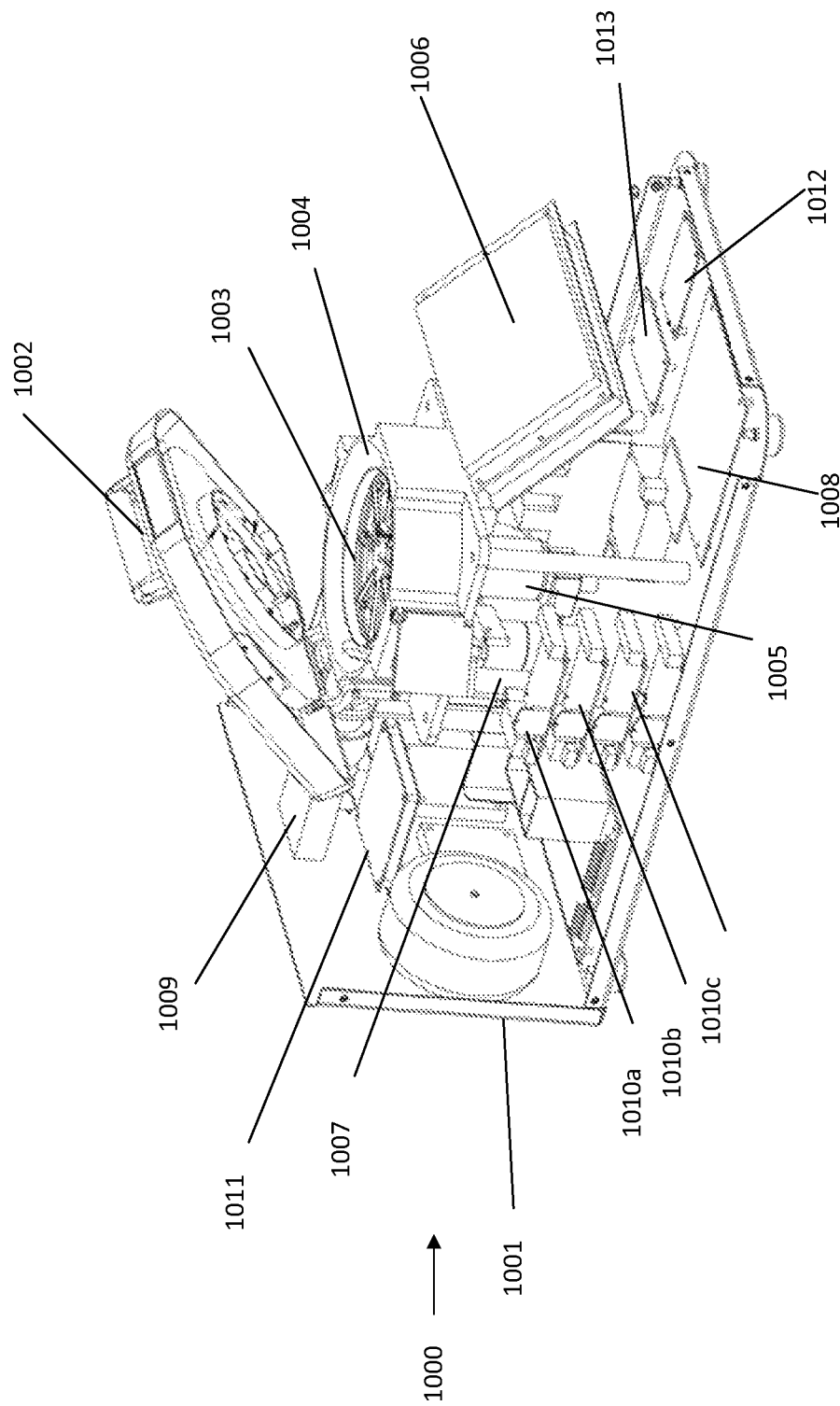
FIG. 19 depicts an oblique view of the inside architecture of the instrument illustrated in FIG. 18.

FIG. 19 shows the instrument 1000 in more detail, especially the components located inside base 1001. The rotational movement of rotor assembly 1003 is produced by motor 1005, located below the centrifugation enclosure 1004. The controller 1008 provides a microprocessor, a memory, electronics and software to control instrument 1000. In this example, the controller provides hardwire communications protocol interface such as Ethernet, serial, digital I/O and analog I/O. In this example embodiment, the touch screen LCD 1006 provides a graphical user interface (GUI) used to operate the instrument software embedded on controller 1008. The LCD communicates with the controller using a serial communication protocol. The controller communicates with motor controllers 1010 and optical signal acquisition board 1011 using serial links. The temperature conditioning board 1012 is connected to analog inputs and excitation sources control board 1013 is connected to digital output of controller 1008.

This example instrument 1000 provides multiple temperature zone controls to control the temperature at predetermined regions of interest of a fluidic centripetal device. In this example embodiment, centrifugation enclosure 1004, rotor assembly 1003 and lid 1001 are designed to ensure a dual zone air temperature control.

Excitation module 1007 provides at least one excitation wavelength. The excitation beam path goes upward to excite fluorescent species inside the cuvettes of the fluidic centripetal devices from the bottom face.

The detection module 1009 is located at the back of the centrifugation enclosure. The detection module 1009 houses the optical elements which collect light emitted by fluorescent species in the fluidic centripetal device at at least one wavelength. In this example embodiment, the detector is a PMT.

Instrument Functions Overview

Figure 20:
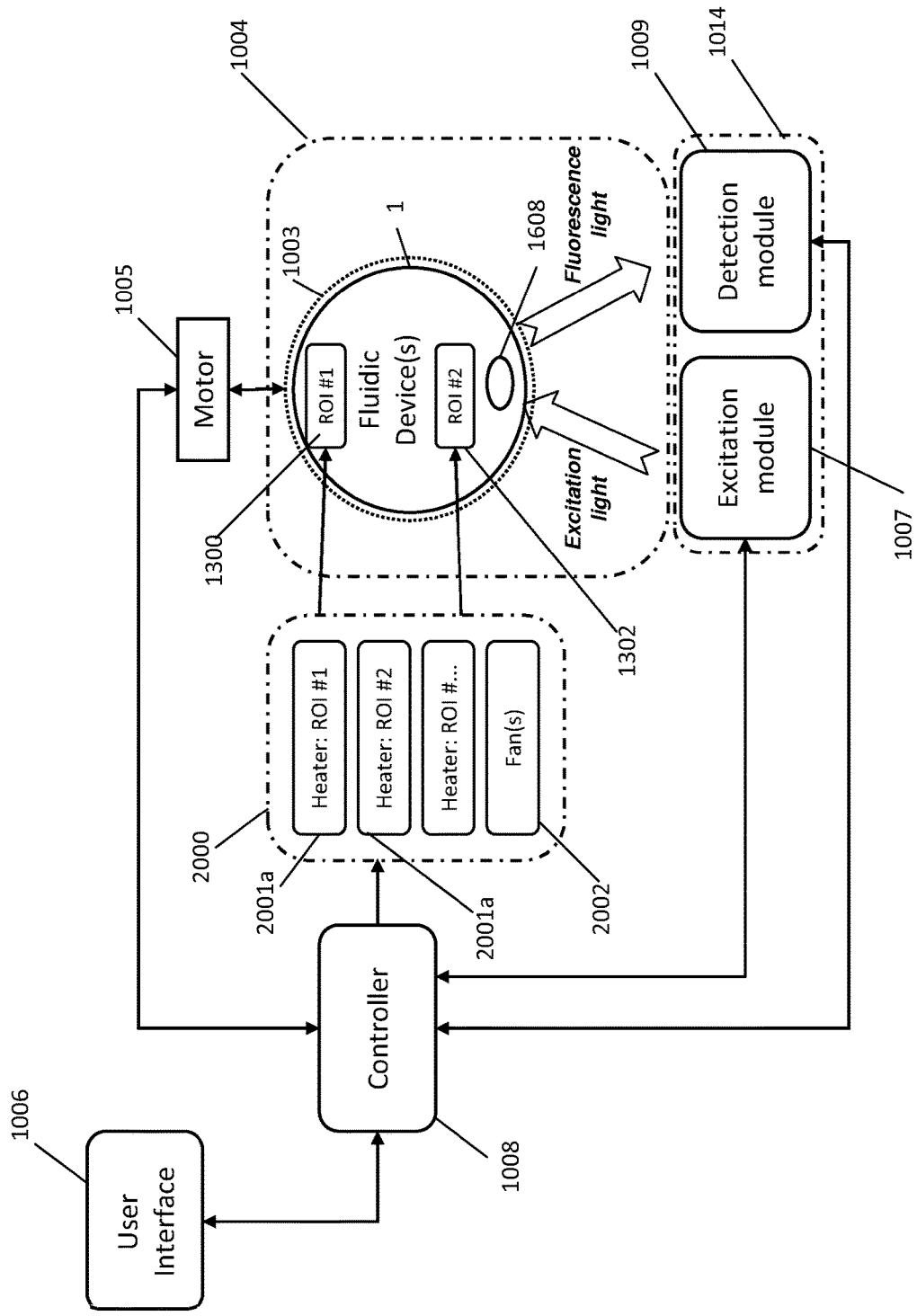
FIG. 20 shows a diagram of various modules of an instrument.

The instrument includes integrated modules: motor 1005, centrifugation enclosure 1004, multiple zone temperature controller 2000, optics 1014, controller 1008 and a human machine interface 1006. It will be understood that arrangement of the various components or modules shown in FIG. 20 is exemplary and is not intended to be limiting.

Centrifugation Enclosure

The rotor assembly 1003 is placed inside a centrifugation enclosure 1004 which revolves to control fluid motion into fluidic centripetal device 1. The rotational movement of the rotor assembly is produced by motor 1005. The rotor assembly may be permanently fixed inside the centrifugal enclosure or may be removed from the centrifugal enclosure to allow placing fluidic centripetal device(s) onto the rotor before placing the rotor inside the centrifugal enclosure. The rotor assembly may revolve in a plane parallel to the base of the instrument or alternatively in a plane perpendicular to the base of the instrument. Revolution speeds of the rotor assembly may vary between 0 and 10000 RPM clockwise and/or counter clockwise with an acceleration rate between 0 and 20000 RPM/s. For example, the rotating sequence is performed automatically by controller 1008.

A permanent magnet (not shown) may be placed inside the centrifugation enclosure to magnetically activate translocatable member 307 located in the bottom-filling chamber of some fluidic centripetal device embodiments. An example of magnetic action for a centrifugal fluidic disc has been described by Kido et al., in "A novel, compact disk-like centrifugal microfluidics system for cell lysis and sample homogenization", Colloids Surfaces B: Biointerfaces, 58 (2007) 44-51.

Multiple Zone Temperature Control

Instrument 1000 also allows multiple zone temperature controller 2000 to modulate the temperature of predetermined regions of interest (ROI) 1300, 1302 of a fluidic centripetal device. Heating/cooling may be achieved with resistive techniques (nichrome wire, ceramic heater), with or without fan, thermoelectric (Peltier) techniques, halogen bulb heating as well as other heating/cooling systems known to those skilled in the art.

Figure 21:
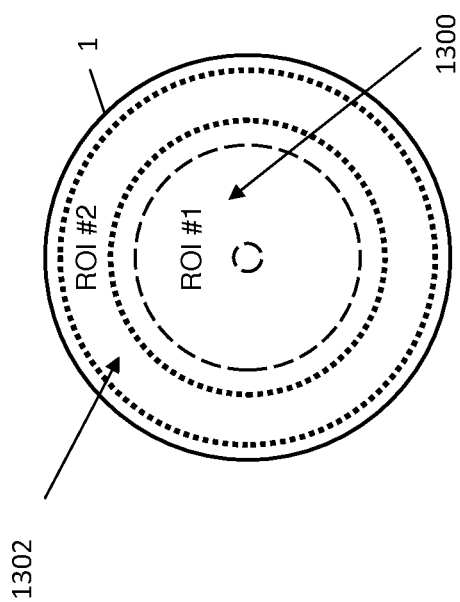
FIG. 21 illustrates multiple zone temperature control regions on a fluidic centripetal device.

Now referring to FIG. 21, a simplified top view of a fluidic centripetal device schematically illustrates two ROI areas 1300, 1302. In this example embodiment, the two ROI areas are non-overlapping and ring-shaped. The heating/cooling of different ROI can be achieved independently at specific time points.

Referring back to FIG. 20, heaters 2001a and 2001b may heat air and the hot air forces the selected ROI of the fluidic centripetal device to be heated and consequently the fluid to be heated. Centrifugation enclosure 1004 may comprise an insulating structure to confine heated air to respective compartments of the centrifugal enclosure to ensure temperature control of the fluidic centripetal device ROI. The temperature of the heated air in each compartment can be measured by a temperature sensor. The temperature sensor may be thermocouples, thermistor, resistance temperature detector (RTD) as well as other temperature sensor known to those skilled in the art. A temperature feedback loop control may be implemented on the controller 1008 to precisely control the temperature of the air.

In some embodiments, a fan can be used to recirculate hot air around a ROI. Alternatively or in addition, a fan can force fresh air to be heated by a heater before contacting the ROI of interest.

In some embodiments, a least one vent (not shown) allows hot air to exit the compartment of the centrifugal enclosure. The vent can be momentary or permanently opened.

In some embodiments, fan 2002 may be used to cool a specific ROI of the fluidic centripetal device. A fan can be used to force cold air (room temperature) to enter into a specific compartment of the centrifugal enclosure to cool a specific ROI of the fluidic centripetal device.

In some embodiments, a least one ROI of the fluidic centripetal device can be maintained below 35° C. when heating another ROI between 25° C. and 99° C.

Preferably, a temperature feedback loop algorithm may be implemented on the controller 1008 to make an isothermal incubation of at least one of the ROI of the fluidic centripetal device. Alternatively or in addition, temperature feedback loop algorithms may be implemented to perform thermal cycling into at least one ROI of the fluidic centripetal device.

In one embodiment, isothermal incubation of one ROI may be used to control nucleic acid amplification inhibition, more specifically, to control inhibition of PCR amplification. Alternatively or in addition, isothermal incubation may be used to heat phase-change material. In a more specific embodiment, the ROI of interest into the fluidic centripetal device includes at least the retention chamber of fluidic centripetal device embodiment described above.

In one embodiment, isothermal incubation of at least one ROI of a fluidic centripetal device may be used to perform an isothermal acid nucleic amplification. In a more specific embodiment, the ROI comprises the cuvettes of an embodiment fluidic centripetal device described above.

In another embodiment, thermal cycling of at least one ROI of a fluidic centripetal device may be used to performed PCR amplification. In a more specific embodiment, the ROI comprises the cuvettes of an embodiment fluidic centripetal device described above.

Figure 22:
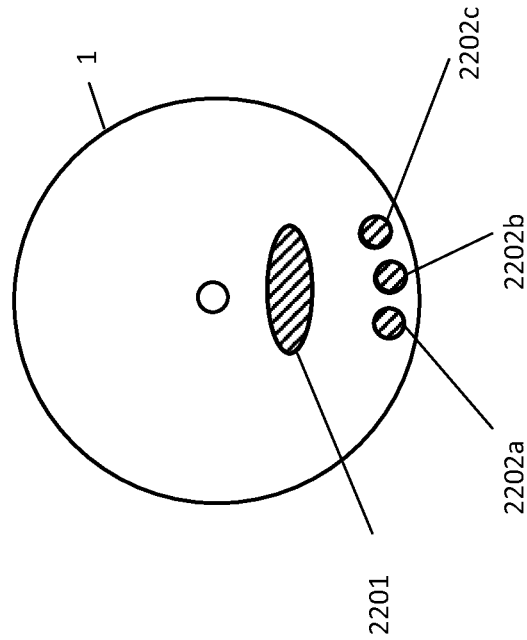
FIG. 22 illustrates an alternative embodiment of the multiple zone temperature control regions on a fluidic centripetal device.

Now referring to FIG. 22, the temperature of the fluid may be controlled in more specific ROI 2201, 2202a, 2202b, 2202c of a fluidic centripetal device. It may be suitable to avoid the heating of unnecessary areas of the fluidic centripetal device to minimize thermal mass and increase heating/cooling rate. The temperature in each specific ROI may be controlled by placing heating/cooling elements and temperature sensors in contact with the bottom face and/or upper face of the fluidic centripetal device on the rotor. The power may be transmitted to heating elements via slip rings (not shown) placed between the motor and the rotor assembly. Temperature sensor data may also be transmitted through the slip ring assembly and/or wirelessly.

In another alternative embodiment, a sub-controller can be integrated into the rotating rotor assembly to implement the temperature control feedback loop of one or more heating elements directly onto the rotor. Electric power may be supplied to the rotating electronic board by one of the batteries placed on the rotating electronic board, induction power transfer between non-rotating part and the electronic board placed on the rotor or with a slip ring interface between the motor and the rotor. A communication interface between this sub-controller and controller 1008 may be implemented through serial communication via a slip ring, RF communication or any other wireless transmission mode. In some embodiments, temperature may be measured into different ROIs of a fluidic centripetal device. Conditioning of the sensing element and conversion from analog to digital may be implemented directly on the rotating controller, thereby avoiding analog sensor signal transmission through a slip ring and diminishing the noise. This embodiment is suitable to calibrate enzymatic amplification reaction such as PCR amplification. In an alternative embodiment, rotating controller may be used to measure electric signal of electrode coated on one of the layer of the fluidic centripetal device. Electrode may be used to detect the presence of liquid in various ROI of the fluidic centripetal device.

Figure 23:
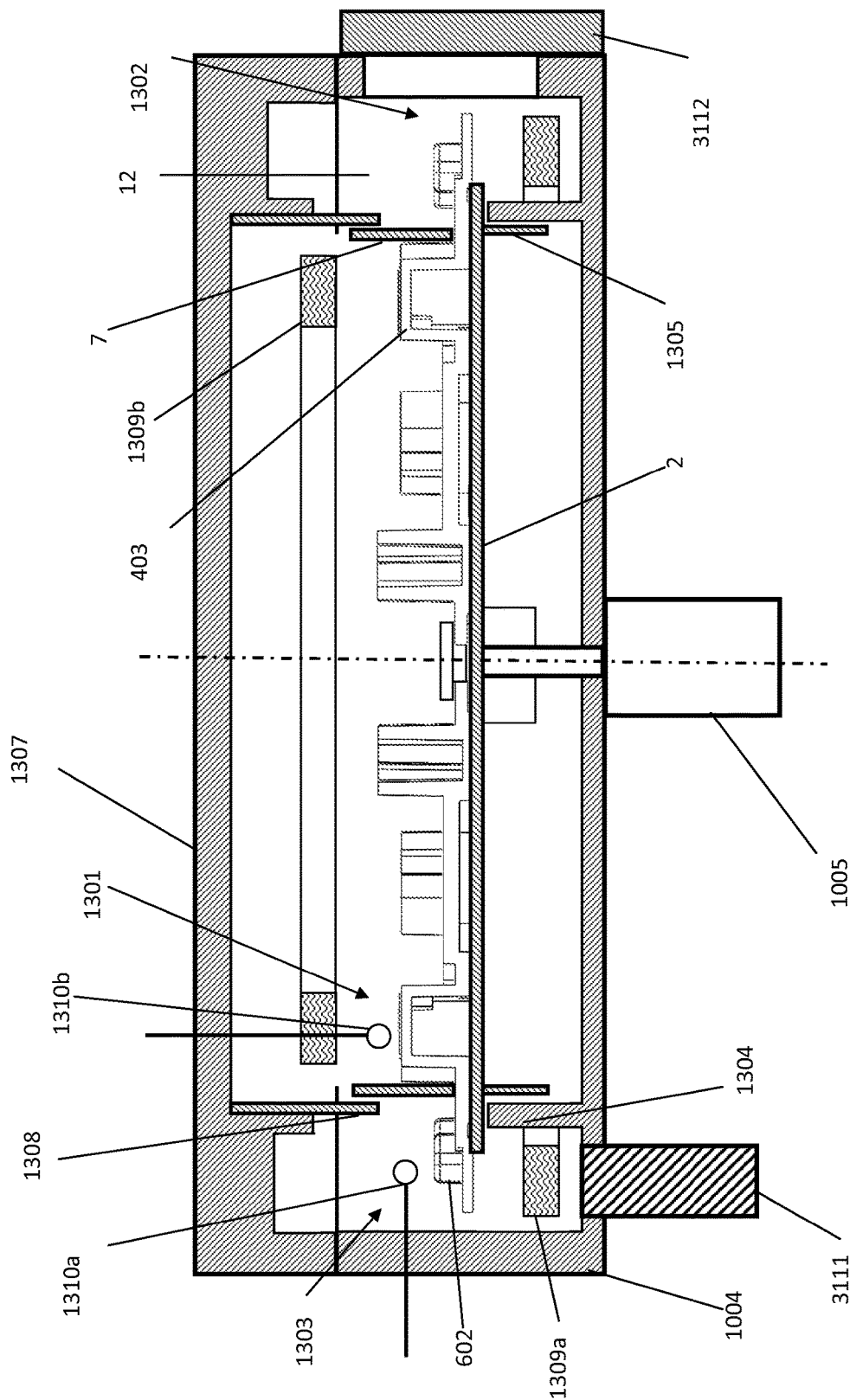
FIG. 23 is a cross-sectional view of the dual zone air temperature control system of the instrument illustrated in FIG. 18.

FIG. 23 illustrates the dual zone air temperature control. In this example, there are two compartments: compartment #1 1301 to heat the retention chamber 403 and the compartment #2 1303 to heat and cool the cuvettes 602 area of the fluidic centripetal device 1. The confinement of air in each area is achieved through a combination of compartments delimited by centrifugation enclosure 1004, centrifugation enclosure separation wall 1304, bottom part of rotor 2, rotor insulation wall 1305, snap ring 7, lid insulation 1307 and the lid insulation wall 1308. Insulating materials can be used to control the heat transfer between adjacent and/or mated components and also to avoid non-controlled heat flux outside centrifugation enclosure 1004. To generate heat inside each compartment, a thermal element 1309a is placed under the fluidic centripetal device in compartment #2 1303, and a heating element 1309b is placed above the fluidic centripetal device in the compartment #1 1301. Thermocouples 1310a and 1310b are placed inside each compartment to measure individual temperature of compartment. In instrument 1000, the heating elements in both compartments are resistive heating coils. To control the cooling rate of compartment #2 1303, blower 3111 forces room temperature air to enter in compartment #2 1303. When blower 3111 is blowing air inside, outlet gate 3112 is opened to eject hot air outside compartment #2 1303. A temperature feedback loop algorithm is implemented on electronic controller 1008 to precisely control the temperature in each compartment. This configuration allows an air heating rate for both compartments to be, for example, between 1 to 20° C./s. The air cooling rate of compartment #2 1303 is, for example, between 0.1 to 20° C./s. Control feedback loop algorithms can be implemented to perform isothermal incubation of each region of interest of the fluidic centripetal device and thermal cycling programs such as PCR amplification for compartment #2 1303.

Optics

Referring back to FIG. 20, optics 1014 of example instrument 1000 include two modules: excitation module 1007 and detection module 1009. These two modules are configured to optically interrogate a liquid 1608 into fluidic centripetal device 1. It is suitable for measuring fluorescent species in the cuvettes of fluidic centripetal device 1. In some embodiments, fluorescence optics may be used to perform real-time PCR or real-time isothermal detection.

In another embodiment, optics 1014 only include a detection module to interrogate the liquid in the fluidic centripetal device.

Excitation module 1007 includes light source(s) and mechanical and optical elements to both spectrally and spatially shape an excitation beam. Several light sources may be housed into an excitation module and their outputs may be coupled to a single beam path. Alternatively, an actuator may allow switching between light sources to excite fluorescent species at different wavelength. In one embodiment, wavelength selection and output power adjustment is performed automatically by controller 1008 of the instrument.

In one embodiment, light sources are light emitting diode (LED). In another embodiment, laser, halogen or mercury lamps may be used.

In some embodiments, excitation module 1007 contains 1 to 6 LEDs to excite fluorescent species at 1 to 6 different wavelengths. Each LED may be spectrally filtered by a single bandpass interferential filter before being coupled to a single beam path. Alternatively, a multiple bandpass interferential filter may be used to filter LEDs after being coupled to a single beam path.

Detection module 1009 comprises optical elements to collect light emitted by species of interest within the fluidic centripetal device. Optical elements can be lens, to shape spatially collected light to a photodetector, interferential filter to select a wavelength band corresponding to the emission spectrum of the fluorescent species. In one embodiment, the detector is a PMT. In another embodiment, detectors can be photodiodes.

In some embodiments, the detection module may detect 1 to 6 different wavelengths onto a single detector. Each wavelength may be filtered by a single bandpass interferential filter and an actuator may allow switching between filter to sequentially detect fluorescent species. Alternatively, a multi bandpass interferential filter may be used to avoid the need of an actuator to switch between wavelengths. In this case, all wavelengths will be detected simultaneously by the detector. It may be necessary to excite fluorescent species sequentially with the excitation module to distinguish each species. For example, this task is performed automatically by controller 1008.

Figure 24:
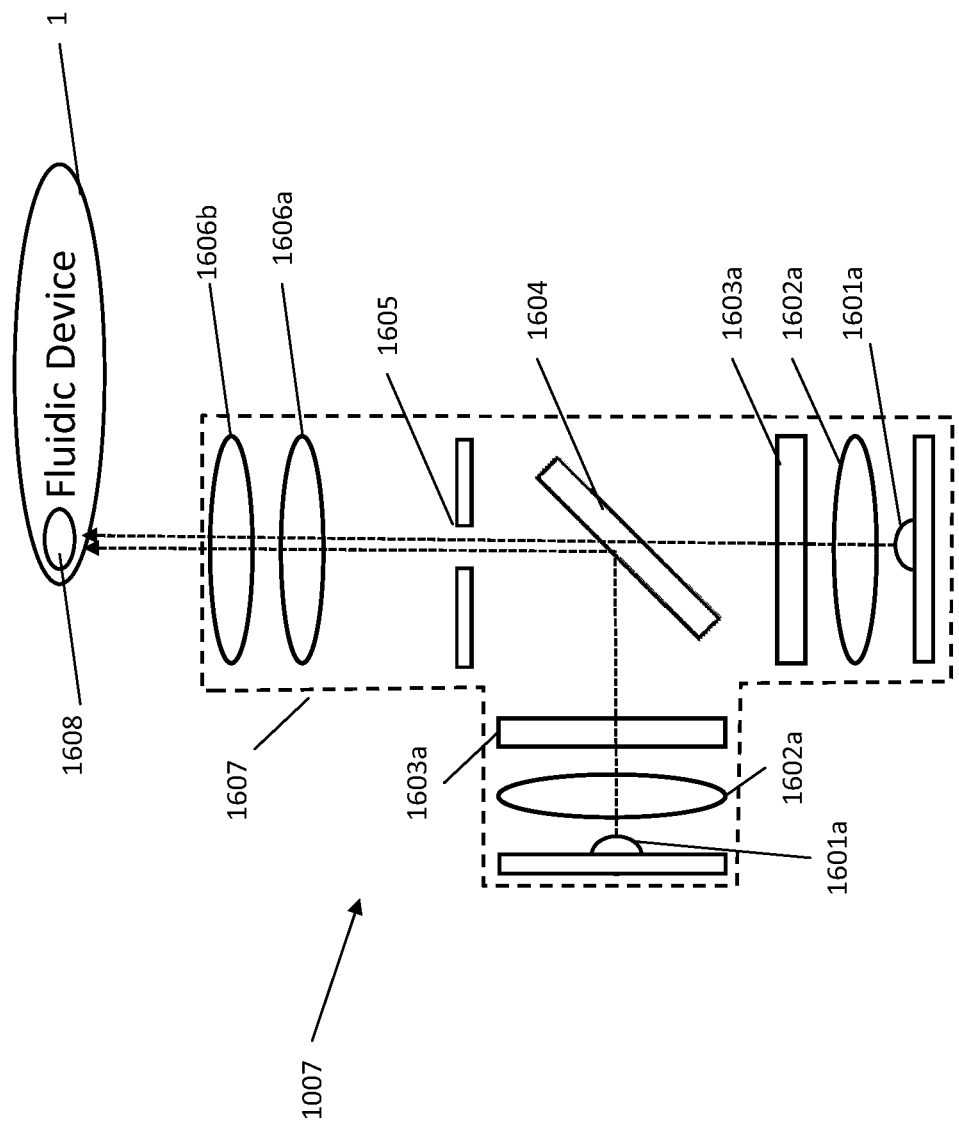
FIG. 24 shows a schematic section view of a multiple wavelength excitation module.

FIG. 24 illustrates a schematic section view illustrating an excitation module 1007 according to an embodiment of the invention. In this embodiment, the beam combiner 1607 is composed of two LEDs 1601a and 1601b, two source lenses 1602a and 1602b, two excitation filters 1603a and 1603b, a dichroic mirror 1604, an aperture 1605 and projection lenses 1606a and 1606b. After being focalised through a lens 1602a, the light from the LED 1601a is spectrally filtered by filter 1603a. Then, light passes through the dichroic beam splitter 1604 and focalisation from lens 1602a is at the aperture 1605. Light emitted by LED 1601b is shaped and filter using lens 1602b and filter 1603b and is also focalised onto the aperture 1605 by reflecting on the beam splitter 1604. Aperture 1605 spatially filters light emitted from the two LEDs 1601a and 1601b. The light is then projected to sample 1608 into fluidic centripetal device 1 through a pair of lenses 1606a and 1606b to excite fluorescent species.

Figure 25:
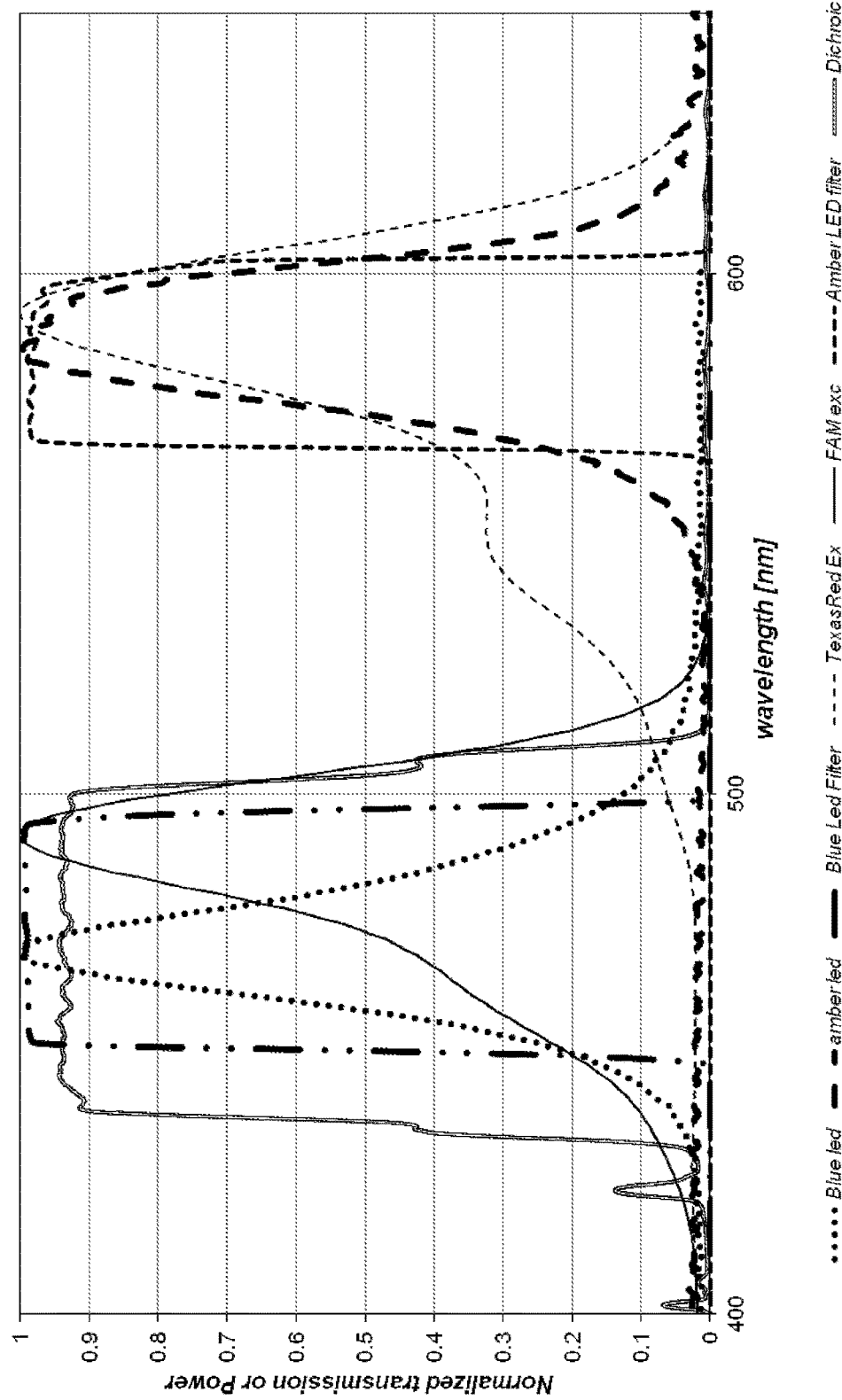
FIG. 25 illustrates spectral profiles of LEDs, excitation filter and dichroic beam splitters tailored to excite FAM and Texas Red fluorescent dyes.

FIG. 25 illustrates the spectral characteristics of example LEDs 1601a and 1601b, filters 1602a and 1602b and beam splitter 1604. The spectral characteristics of the beam splitter allow to combine blue LED and amber LED having peak power at respectively 471 nm and 590 nm. This spectral arrangement is well suited to excite both carboxyfluorescein (5-FAM) and/or Texas Red® commonly used in real-time PCR amplification.

Figure 26:
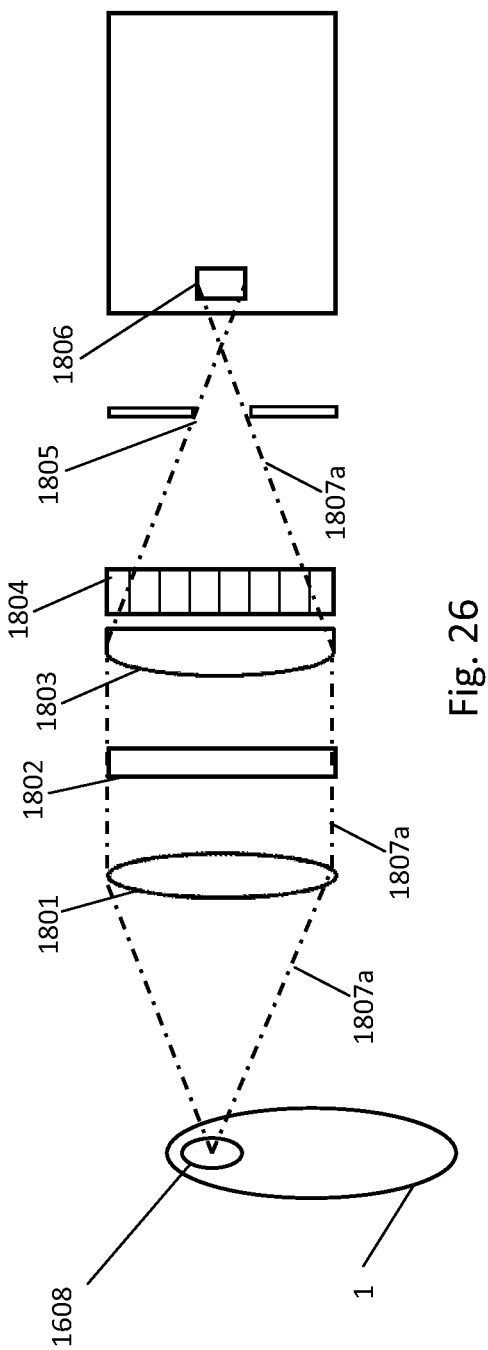
FIG. 26 illustrates a schematic section view of a detection module.

Now referring to FIG. 26, schematic side section views illustrate an example detection module to collect the light emitted by the fluorescent species of interest at two wavelengths from sample 1608 located into fluidic centripetal device 1. Fluorescence emitted is collected and collimated by the objective lens 1801. Then, after being spectrally filtered through interferential filter 1802 having two transmission bands corresponding to the emission spectrum of the fluorescent species, fluorescence beam path 1807 is shaped separately in both planes by two cylindrical lenses 1803 and 1804. The beam is then spatially filtered by the rectangular aperture field stop 1805 and the rectangular photocathode of the PMT 1806.

Figure 27:
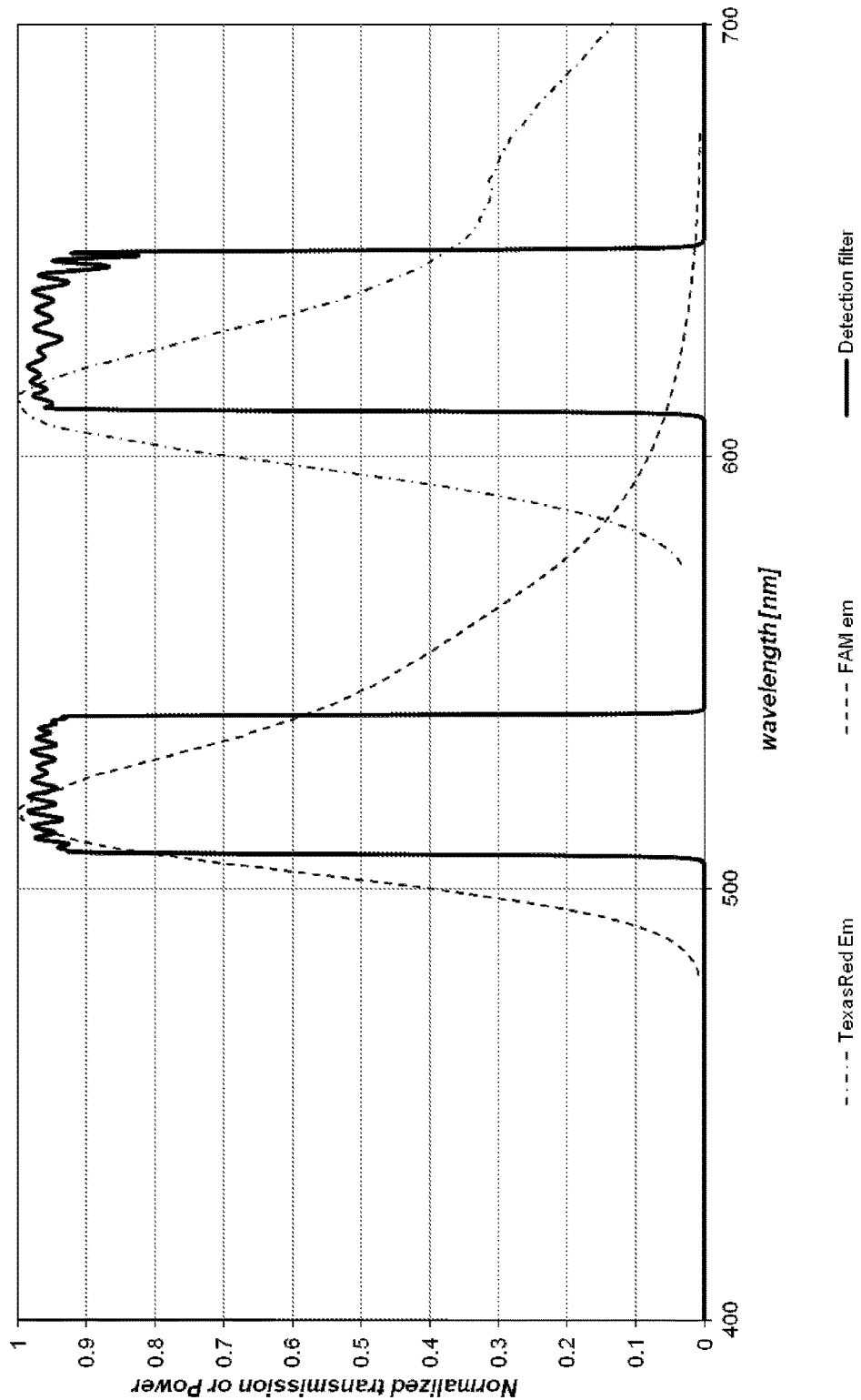
FIG. 27 illustrates spectral profiles of a dual-band bandpass interferential filter tailored for the detection of FAM and Texas Red fluorescent dyes.

FIG. 27 illustrates the spectral characteristic of the dual band filter. This spectral configuration allows transmission centered at 524 nm and 628 nm. This configuration is well suited for the detection of 5-carboxyfluorescein (5-FAM) and Texas Red® commonly used in real-time PCR amplification. Furthermore, this module can have several configurations depending on the needs of the intended application.

Figure 28:
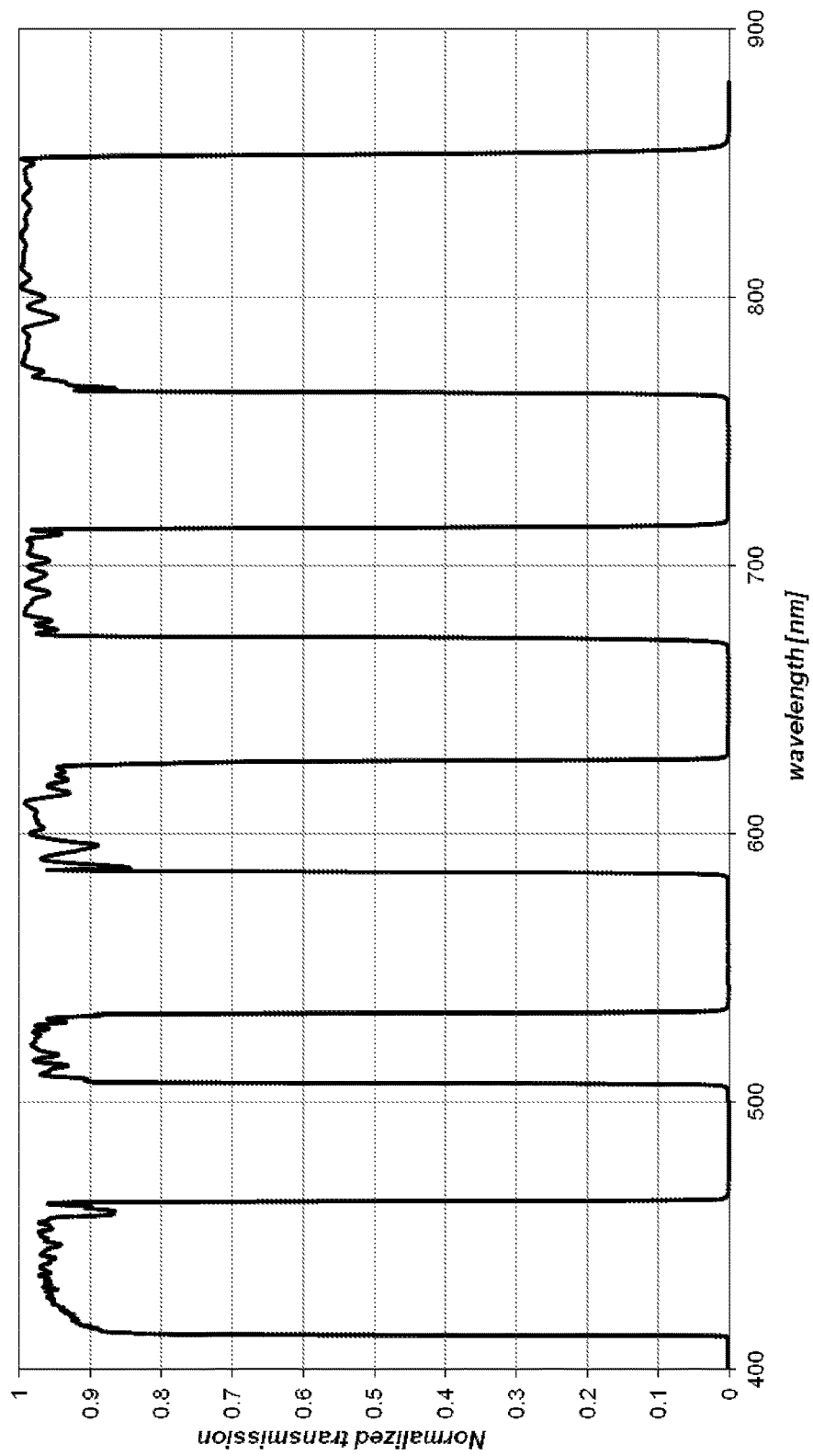
FIG. 28 illustrates spectral profiles of penta-band bandpass interferential filter tailored for the detection of common fluorescent dyes.

FIG. 28 shows more complex spectral characteristics with 5 transmission bands: [420-460 nm], [510-531 nm], [589-623 nm], [677-711 nm] and [769-849 nm]. This multi bandpass filter is well suited for the sequential detection of the five following dyes: AlexaFluor350, 5-carboxyfluorescein (5-FAM), Texas Red®, Cy5, and Alexa 750.

Testing Method for Thermocycling Amplification

Figure 29:
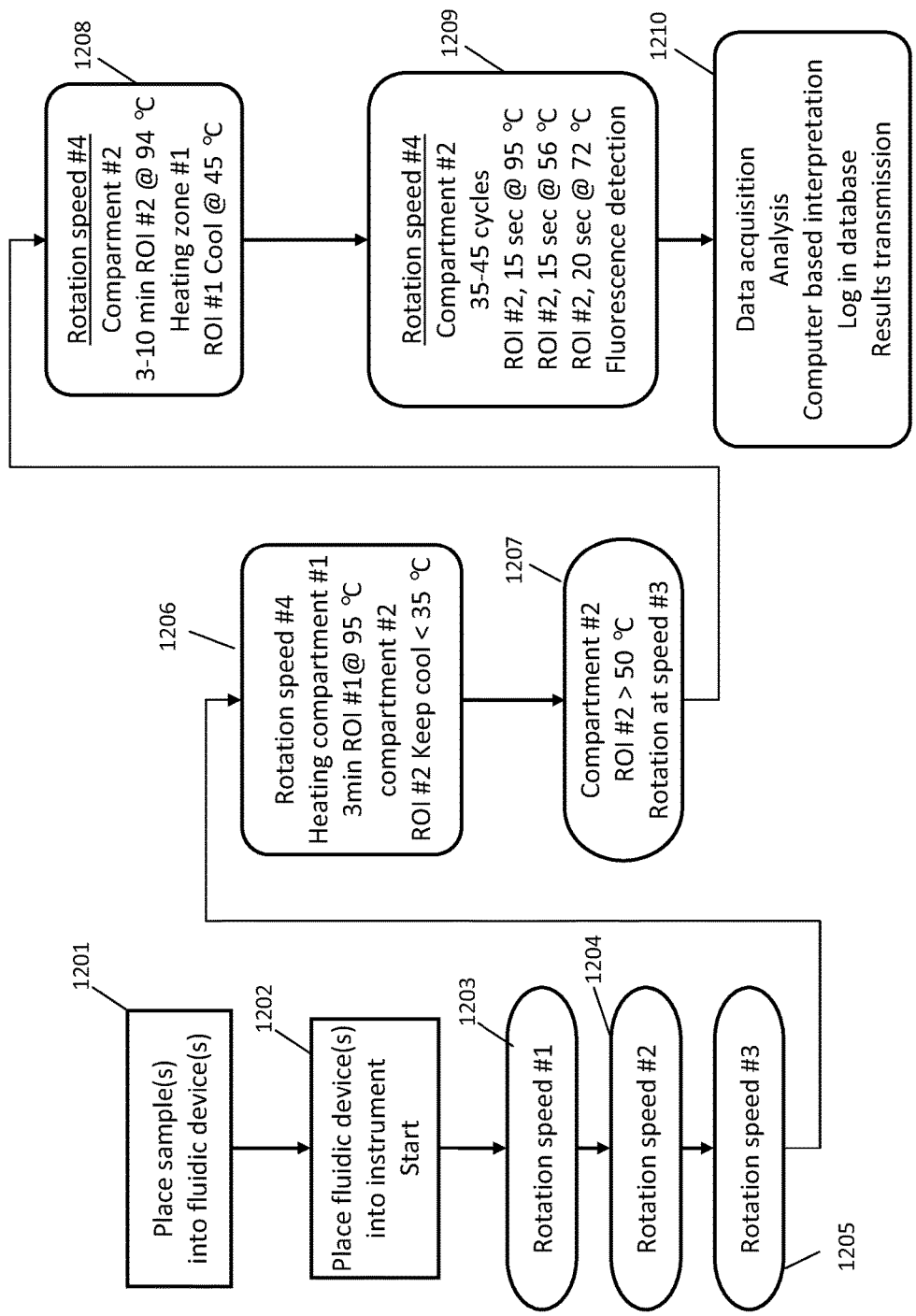
FIG. 29 is a flow chart of the steps involved to process a PCR assay using the instrument illustrated in FIG. 21.

FIG. 29 illustrates an example workflow using the instrument 1000 and example fluidic centripetal device of FIG. 17 to perform sample preparation of biological material, control the potential inhibitors and detect with a real-time PCR. This flowchart lists example temperatures, durations, speeds and steps.

First step 1201 consists in loading a biological sample into the intake receptacle 5. Then, place the fluidic centripetal device into the instrument and press start button 1202. From this point, the instrument will take care of the whole process. The rotation will start at speed #1 1203 to transfer the liquid from the intake receptacle 5 to the lysis chamber 315 and evacuate part of the sample into the overflow chamber 309. The rotation speed will change to speed #2 1204 to activate the movement of translocating member 307 inside the bottom-fillable lysis chamber. Permanent magnets placed under rotor 2 create a fluctuating magnetic field when fluidic centripetal devices rotate over it. After a predetermined amount of time, the rotation is changed again to speed #3 1205 to clarify the lysate and burst the metering outlet 312.

The metered volume is transferred into retention chamber receptacle 406. At step 1206, the rotation is changed again to speed #4. Compartment #1 is heated so the ROI #1 of fluidic centripetal device reaches 95° C. for 3 minutes, for example, to control inhibitors potentially present in the biological sample. This heating will also melt liquid container wax cap 411 to release diluent 410 inside retention chamber 403. It should be noted that compartment #2 of the instrument and ROI #2 of the fluidic centripetal device are kept at a temperature under 35° C., for example, by activating the blower if needed.

At the end of step 1206, the lysate is generally well mixed with the diluent and is ready to be transferred into the distribution channel and cuvettes 602. The transfer is done by heating compartment #2 at a temperature such that ROI #2 reaches a temperature above 50° C., for example, to melt wax 608 in waste chamber 605 and by changing the rotation to speed #3, step 1207. The dilution reservoir outlet 405 bursts and the liquid is transferred into cuvettes 602 to resuspend pre-stored PCR dried reagents 607. At step 1208, the rotation speed is changed to speed #4 and the hot start enzyme contained in reagents 607 is activated by heating compartment #2 so that ROI #2 of fluidic centripetal device reaches 94° C., for example, for a period between 3 to 10 minutes depending on the specific reagents used.

During this time, heating zone #1 naturally cools down to a temperature about 45° C. Continuing at rotation speed #4, real-time PCR cycling protocol 1209 is started. The temperature in compartment #2 is cycled so that temperature in ROI #2 is cycled between about 95° C., 56° C. and 72° C. for periods varying respectively from 1 to 15 s, 0 to 15 s and 1 to 20 s. At the end of each 72° C. cycle, the fluorescence measurement is taken at 1 to 6 different excitation/detection wavelengths simultaneously or sequentially. The cycling is done 35 to 45 times. The real-time-PCR fluorescence curve is then analyzed, and interpreted by a computer-based algorithm. Results are logged in a database and are optionally transmitted to the test operator or to a physician.

Figure 30A:
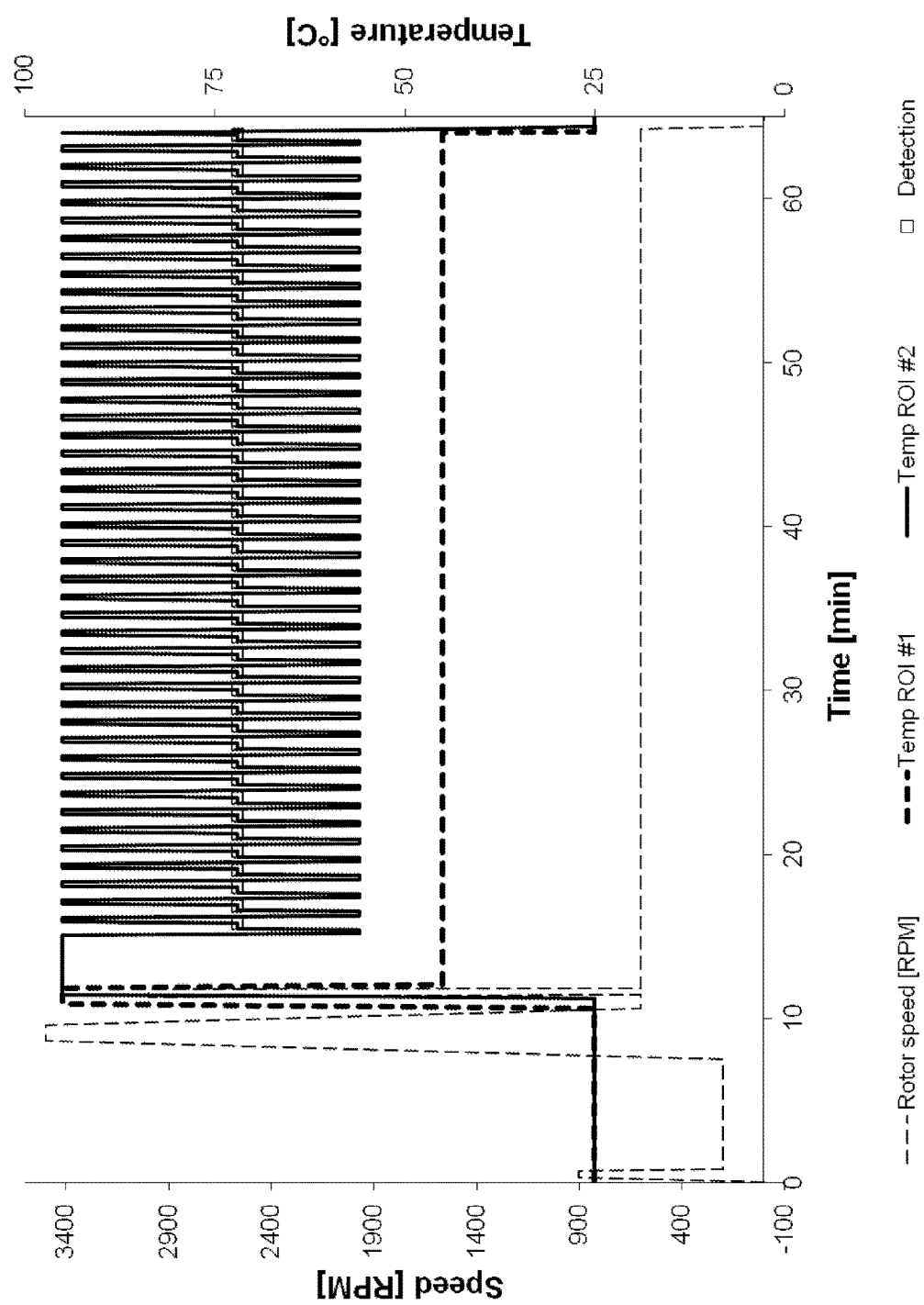
FIGS. 30A, 30B, 30C illustrate the speed of the rotor and temperatures of the fluidic centripetal device over the time to process a PCR, using the instrument illustrated in FIG. 18.
Figure 30B:
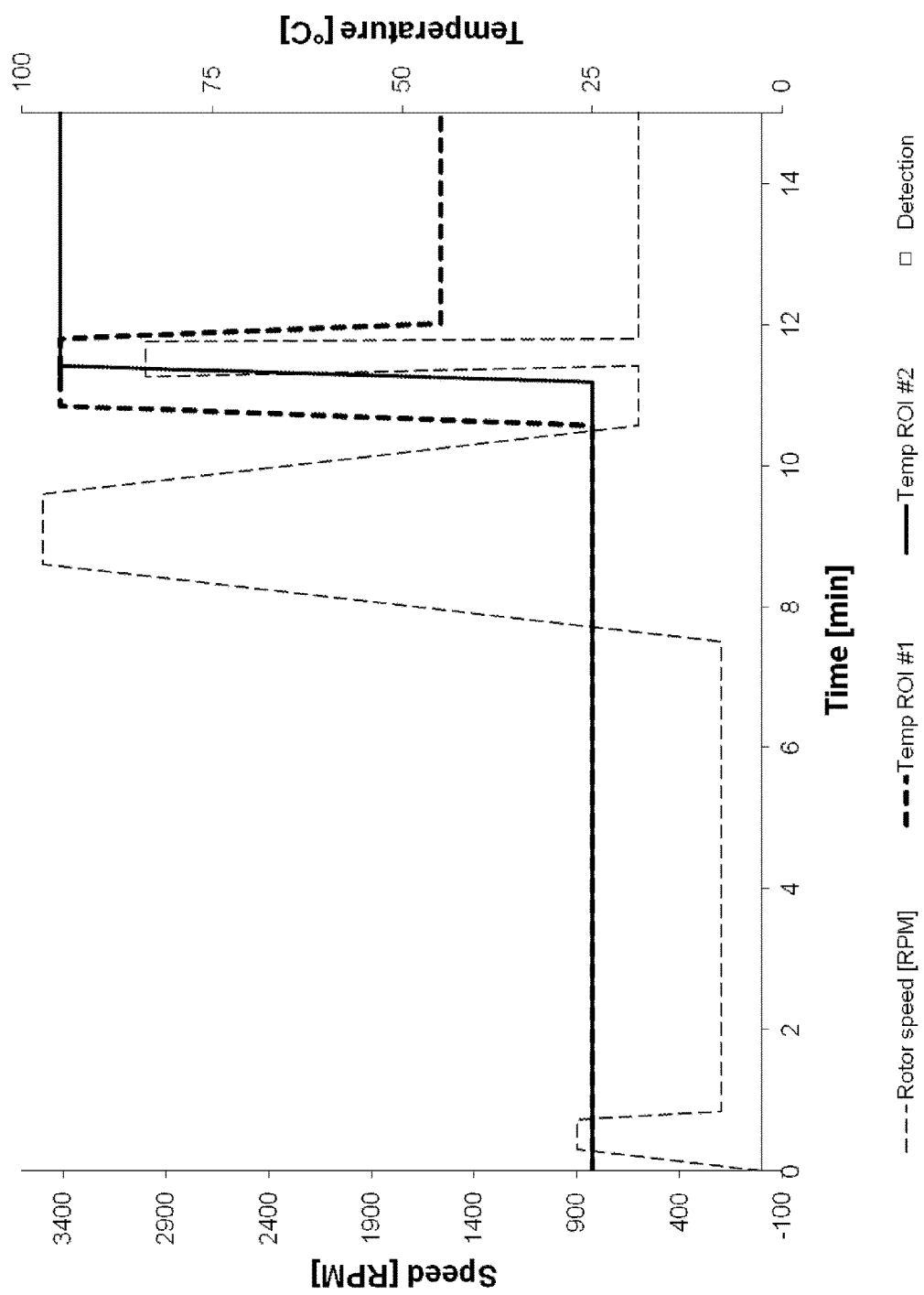
Figure 30C:
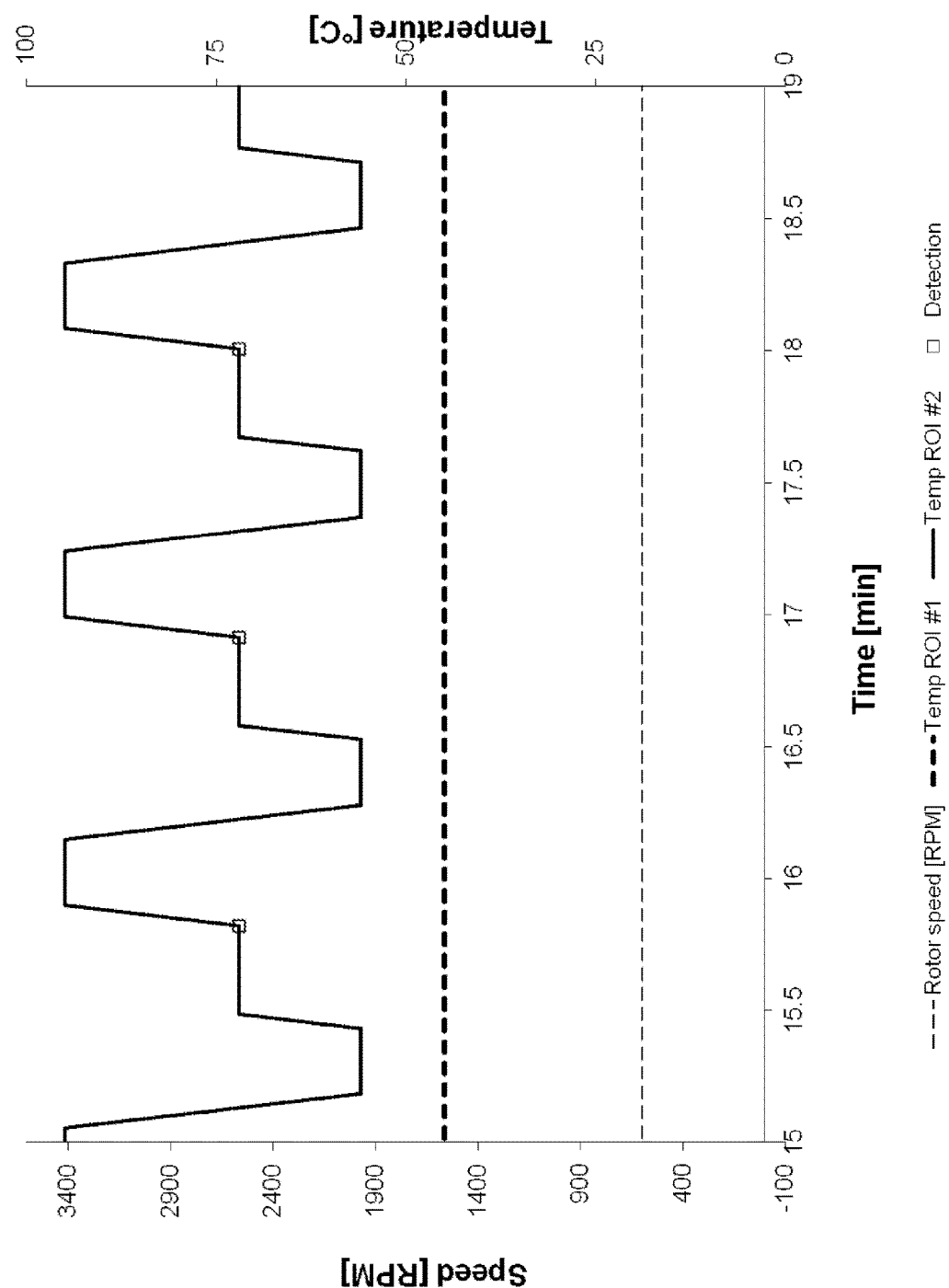

FIG. 30A illustrates the rotation speed profile, thermal temperature profile of ROI #1 and ROI #2 for the example embodiment described in relation with FIG. 29. FIG. 30B illustrates the period prior to real-time PCR and FIG. 30C illustrates 3 cycles of the real-time PCR detection.

In another embodiment, the instrument may alternatively process sample-preparation and real-time isothermal detection. The isothermal amplification used can be, but is not limited to, RMA (ribonuclease-mediated amplification), HDA (Helicase Dependent Amplification), RPA (Recombinase Polymerase Amplification) and SPIA (Single Primer Isothermal Amplification), LAMP (Loop mediated isothermal Amplification).), SDA (Strand displacement amplification), NASBA (Nucleic Acid Sequence Based Amplification), wGA (Whole Genome Amplification), pWGA (primase-based Whole Genome Amplification), ICAN (Isothermal and Chimeric primer-initiated Amplification of Nucleic acids), EXPAR (Exponential amplification reaction), NEAR (Nicking enzyme amplification reaction), RCA (Rolling circle amplification), TMA (Transcription-Mediated Amplification).

It will be recognized by those skilled in the art that a plurality of fluidic centripetal devices can be manufactured with specific applications in mind, permitting sample volume definition, sample homogenization, sample lysis, sample metering, sample dilution, sample mixing and sample detection.

Testing Method for Isothermal Amplification

In an alternative embodiment of the flow chart illustrated on FIG. 29, steps 1207, 1208, 1209 and 1210 are modified to perform sample preparation of biological material, control the potential inhibitors and detect with a real-time isothermal amplification. In a more particular embodiment, the isothermal real time amplification is real time Recombinase Polymerase Amplification (real time RPA).

The steps are as follows: load a biological sample into the intake receptacle 5. Then, place the fluidic centripetal device into the instrument and press the start button. From this point, the instrument will take care of the whole process. The rotation will start a speed #1 to transfer the liquid from the intake receptacle 5 to the lysis chamber 315 and evacuate part of the sample into the overflow chamber 309. The rotation speed will change to speed #2 to activate the movement of the translocating member 307 inside the bottom-fillable lysis chamber. Permanent magnets placed under the rotor 2 create a fluctuating magnetic field when fluidic centripetal devices rotate over it. After a predetermined amount of time, the rotation is changed again to speed #3 to clarify the lysate and burst the metering outlet 312.

The metered volume is transferred into the retention chamber receptacle 406. The rotation is changed again to speed #4. The compartment #1 is heated so that in ROI #1 of fluidic centripetal device the temperature is at 95° C. for 3 minutes, for example, to control inhibitors potentially present in the biological sample. This heating will also melt the liquid container wax cap 411 to release the diluent 410 inside the retention chamber 403. It should be noted that compartment #2 is kept at a lower temperature so that ROI #2 is kept at a temperature under 35° C., for example, by activating the blower if needed.

The lysate is generally well mixed with the diluent and is cooled down at a temperature equal or below 42° C. and ready to be transferred into the distribution channel and cuvettes 602. In this embodiment the diluent is water and magnesium. The transfer is done by keeping compartment #2 at a temperature so that ROI #2 is kept at 37-42° C., and by changing the rotation to speed #3. The dilution reservoir outlet 405 bursts and the liquid is transferred into cuvettes 602 to resuspend pre-stored PCR dried reagents 607. In this embodiment, dried reagent 607 comprises RPA fluorescent probe, primers, recombinase, polymerase, exonuclease, the crowding agent, GP32, uvsY, and uvsX. The rotation speed is changed to speed #4 and the compartment #2 is heated so that ROI #2 reaches 37-42° C.

During this time, heating zone #1 naturally cools down to a temperature below 45° C. The fluorescence measurement is taken at 1 to 6 different excitation/detection wavelengths simultaneously or sequentially every few minutes. The amplification step is stopped after 20 minutes. The real-time-RPA fluorescence signal is then analyzed, and interpreted by a computer-based algorithm. Results are logged in a database and are optionally transmitted to the test operator or to a physician.

In another embodiment, the instrument may alternatively process sample-preparation and real-time isothermal detection. The isothermal amplification used can be, but is not limited to, RMA (ribonuclease-mediated amplification), HDA (Helicase Dependent Amplification), RPA (Recombinase Polymerase Amplification) and SPIA (Single Primer Isothermal Amplification), LAMP (Loop mediated isothermal Amplification).), SDA (Strand displacement amplification), NASBA (Nucleic Acid Sequence Based Amplification), wGA (Whole Genome Amplification), pWGA (primase-based Whole Genome Amplification), ICAN (Isothermal and Chimeric primer-initiated Amplification of Nucleic acids), EXPAR (Exponential amplification reaction), NEAR (Nicking enzyme amplification reaction), RCA (Rolling circle amplification), TMA (Transcription-Mediated Amplification).

It will be recognized by those with skill in the art that a plurality of fluidic centripetal devices can be manufactured with specific applications in mind, permitting sample volume definition, sample homogenization, sample lysis, sample metering, sample dilution, sample mixing and sample detection.

Example 1

The following example is illustrative and is not intended to be limiting.

The present example concerns the detection of the presence of Group B *streptococcus* from a pregnant woman vaginal-anal swab.

The fluidic centripetal device used for the purpose of this example has the external shape described in FIG. 1C and is composed of the fluidic elements shown and described in FIG. 17.

TABLE 1

Summary of the details of the fluidic centripetal device structures

| | |
|---|---|
| Fluidic Layer | Material: clear polycarbonate (Lexan HP1-112) Fabrication process: injection molded + micromilling of lysis chamber outlet and retention chamber outlet |
| Thin bottom layer | Polycarbonate (thickness = 0.015") (McMaster Carr #85585K14) |
| Pressure sensitive adhesive | 9493R, 3M ™ |
| Translocatable member | Magnetic Stainless Steel Tumble Stir Elements V&P Scientific, Inc. #721-F (diameter = 4 mm, thickness = 0.5 mm) |
| Lysis chamber reagents | Slurry of glass beads G1145 in 1% PVP aqueous solution |
| PCR reagents | 2 µl of specific GBS primers Sag59 TTTCACCAGCTGTATTAGAAGTA (SEQ ID NO: 4) Sag190 GTTCCCTGAACATTATCTTTGAT (SEQ ID NO: 2) Taqman probe: (FAM)CCCAGCAAATGGCTCAAAAGC (SEQ ID NO: 3) (BHQ-1)OmniMix HS (Takara #700-2102) |
| Liquid container | Plastic restaurant straw (diameter = 4 mm) Hot glue arrow BAP 5-4 Paraffin wax (Calwax ® #CAL-140) PCR treated water |
| Waste chamber | Paraffin wax (Calwax ® #CAL-120) |

The liquid container was fabricated using the following protocol: close one extremity of the plastic straw with hot glue; load 140 µl of PCR treated water; seal the container with melted paraffin wax.

The fluidic centripetal device was assembled using the following protocol: place paramagnetic disc in the lysis chamber; load 60 µl of glass beads slurry; load 2 µl primers in each cuvette; load 0.5 µl of TaqMan probe; dry the slurry and the primers under vacuum overnight; place the liquid container in the retention chamber; dispense Low Melting Paraffin wax in the waste chamber.

The following steps are done in a glove box under Argon atmosphere: place one bead of OmniMix HS per detection cuvette; bond the thin bottom layer to the fluidic layer using the pressure sensitive adhesive; place assembled fluidic centripetal device in an aluminum pouch with desiccant and seal the pouch.

Experiment

During a clinical study, vaginal/anal swabs were collected from pregnant women using Clinical Packaging snap valve technology filled with 600 µl of Tris EDTA 10 mM (TE).

After resuspension of the swab with the 600 µl of TE, a quantity of 170 µl of the swab dilution is placed directly into the intake receptacle of the fluidic centripetal device described above.

The fluidic centripetal device is laced into the instrument and the following protocol is performed in the dual zone temperature control instrument for the sample preparation.

Parameters for metering, lysis and control of PCR inhibitors used in this example are the following:

TABLE 2

Bottom-fillable chamber loading

| Step | Parameters | Condition |
|---|---|---|
| 1 | Acceleration | Speed −900 RPM, acceleration rate 50 RPM/s |
| 2 | Waiting | 25 s |

TABLE 3

Lysis step

| Step | Parameters | Condition |
|---|---|---|
| 3 | Acceleration | Speed −200 RPM, acceleration rate 1000 RPM/s |
| 4 | Waiting | 300 s |

TABLE 4

Clarification step and transfer to retention chamber receptacle

| Step | Parameters | Condition |
|---|---|---|
| 5 | Acceleration | Speed -3500 RPM, acceleration rate 50 RPM/s |
| 6 | Waiting | 60 s |

TABLE 5

PCR Inhibitors control

| Step | Parameters | Condition |
|---|---|---|
| 7 | Acceleration | Speed -600 RPM, acceleration rate 50 RPM/s |
| 8 | Heat zone #1 | Temp 110° C., 180 s |
| 9 | Waiting | 20 s |

TABLE 6

PCR cuvette filling

| Step | Parameters | Condition |
|---|---|---|
| 10 | Acceleration | Speed -3000 RPM, acceleration rate 500 RPM/s |
| 11 | Wait | 155 s |
| 12 | Stop heating zone #1 | |
| 13 | Start blower zone #2 | |
| 14 | Waiting | 30 s |
| 15 | Stop Blower zone #2 | |
| 16 | Stop | |

The fluidic centripetal device is then transferred onto an adapted rotor specifically designed to work on a RotorGene to process the real-time PCR using the following conditions.

TABLE 7

Process conditions

| Cycle | Cycle point |
|---|---|
| Hold | @ 94° C., 3 min |
| Cycling (45) | Step 1 @ 95° C., hold 20 s |
|  | Step 2 @ 56° C., hold 60 s |
|  | Step 3 @ 72° C., hold 30 s |

Results:

Swab found positive for the presence of GBS detection at a CT of 28.30.

Example 2

The following example is illustrative and is not intended to be limiting.

The present example concerns the use of an example embodiment of the fluidic centripetal device to detect the presence of Group B *streptococcus* from pregnant women vaginal-anal swabs.

The fluidic centripetal device used for the purpose of this example has the external shape described in FIG. 1C and is composed of the fluidic elements shown and described in FIG. 17.

TABLE 8

Summary of the details of the fluidic centripetal device structures

| | |
|---|---|
| Fluidic Layer | Material: Clear polycarbonate (Lexan HP1-112) |
| | Fabrication process: Injection molded |
| Thin bottom layer | Polycarbonate (thickness = 0.015") |
| | (McMaster Carr #85585K14) |
| Pressure sensitive adhesives | 9795R, 3M ™, in contact with fluidic layer. |
| | 467 MP, 3M ™, in contact with bottom layer and 9795R layer |
| Translocatable member | Magnetic Stainless Steel Tumble Stir Elements V&P Scientific, Inc. #721-F (diameter = 4 mm, thickness = 0.5 mm) |
| Lysis chamber (Bottom-fillable chamber) reagents | Slurry of glass beads Sigma #G1145 (150-212 microns) in 0.5% PVP aqueous solution |
| PCR reagents, dried in each cuvettes, per reaction | Primers and probes for the GBS assays as listed in Table 15 at 0.4 µM for primers SEQ ID 1-2 and SEQ ID 4-5; 0.2 µM for probes SEQ ID 3 and SEQ ID 6; internal control target sequence SEQ ID 7 at 500 copies per reaction |
| | PCR buffer, 1X |
| | BSA, 3.3 mg/ml |
| | dATP, 0.2 mM |
| | dCTP, 0.2 mM |
| | dGTP, 0.2 mM |
| | dTTP, 0.2 mM |
| | GoTaq ™ polymerase, Promega #PRM3005 |
| | Trehalose, 6% |
| Liquid container | Polyallomer Tubes, 5 × 20 mm Beckman Coulter #34263 |
| | Hot glue Arrow BAP 5-4 |
| | Paraffin wax (Calwax ® #CAL-140) |
| | PCR diluent liquid (5.83 mM MgCl$_2$) |
| Waste chamber | Paraffin wax (Calwax ® #CAL-120) |

The liquid container was fabricated using the following protocol: load 120 ul of PCR diluent liquid; seal the polyallomer tube with Hot glue Arrow BAP 5-4.

The fluidic centripetal device was assembled using the following protocol: Place paramagnetic disc in the lysis chamber; load 60 µl of glass beads slurry; load 4.6 µl of PCR reagents in each cuvette; dry the slurry and the PCR reagents under heat and vacuum; place the liquid container in the retention chamber; dispense Low Melting Paraffin wax in the waste chamber.

Bind the pre-assembled layers 9795R/467 MP/polycarbonate to the fluidic layer and apply a pressure using a press with a torque of 90 in·lbs. Place assembled fluidic centripetal device in an aluminum pouch with desiccant and seal the pouch.

Experiment

During a clinical study, vaginal/anal swabs were collected from pregnant women using Medical Packaging snap valve technology filled with 600 µl of Tris EDTA 10 mM (TE).

After resuspension of the swab with the 600 µl of TE, 170 µl of the swab dilution are placed directly into the sample intake receptacle of the fluidic centripetal device described above.

The fluidic centripetal device is placed into the instrument and the following protocol is performed in the dual zone temperature control instrument for the sample preparation.

Parameters for metering, lysis and control of PCR inhibitors used in this example are the following:

TABLE 9

Bottom-fillable chamber loading

| Step | Parameters | Condition |
|---|---|---|
| 1 | Acceleration | Speed -1000 RPM, acceleration rate 300 RPM/s |
| 2 | Waiting | 30 s |

TABLE 10

Lysis step

| Step | Parameters | Condition |
|---|---|---|
| 3 | Acceleration | Speed -180 RPM, acceleration rate 1000 RPM/s |
| 4 | Waiting | 300 s |

TABLE 11

Clarification step and transfer to retention chamber receptacle

| Step | Parameters | Condition |
|---|---|---|
| 5 | Acceleration | Speed -1500 RPM, acceleration rate 50 RPM/s |
| 6 | Acceleration | Speed -3500 RPM, acceleration rate 300 RPM/s |
| 7 | Waiting | 30 s |

TABLE 12

PCR Inhibitors control by heating and fluid dilution

| Step | Parameters | Condition |
|---|---|---|
| 8 | Acceleration | Speed -450 RPM, acceleration rate 1000 RPM/s |
| 9 | Heat zone #1 | Temp 165° C., 180 s |
| 10 | Waiting | Speed -3000 RPM, acceleration rate 300 RPM/s |

TABLE 13

| Step | Parameters | Condition |
|---|---|---|
| | PCR cuvette filling | |
| 11 | Acceleration | Speed -3000 RPM, acceleration rate 500 RPM/s |
| 12 | Wait | 155 s |
| 13 | Stop heating zone #1 | |
| 14 | Start blower zone #2 | |
| 15 | Waiting | 30 s |
| 16 | Stop Blower zone #2 | |
| 17 | Stop | |

The fluidic centripetal device is then transferred onto an adapted rotor specifically designed to work on a RotorGene to process the real-time PCR using the following conditions.

TABLE 14

| Cycle | Cycle point |
|---|---|
| Thermocycling conditions | |
| Hold | @ 94° C., 3 min |
| Cycling (45) | Step1 @9 7° C., hold 20 s |
| | Step2 @ 58° C., hold 20 s |
| | Step3 @ 72° C., hold 20 s |

Results:

Swabs were found positive for the presence of GBS detection at CT between 27 and 32.

Example 3

The following example is illustrative and is not intended to be limiting.

The present example concerns the use of an example embodiment of the fluidic centripetal device to detect the presence of human beta-globin gene from a human cheek swab sample, *Escherichia coli* from human urine samples, and methicillin resistant *Staphyloccus aureus* (MRSA) from human nose swabs samples.

TABLE 15

List of selected amplification primers and detection probes for the different assays

| Assay combination | Oligonucleotide type | SEQ ID | Sequence$^a$ |
|---|---|---|---|
| GBS | Amplification primer | SED ID 1 | TTTCACCAGCTGTATTAGAAGTA |
| | Amplification primer | SED ID 2 | GTTCCCTGAACATTATCTTTGAT |
| | Detection Taqman probe FAM-BHQ | SED ID 3 | CCCAGCAAATGGCTCAAAAGC |
| | IC Amplification primer | SED ID 4 | TTTCACCAGCTGTATTAGAAGTA |
| | IC Amplification primer | SED ID 5 | GTTCCCTGAACATTATCTTTGAT |
| | IC Detection Taqman probe Cal Red-BHQ | SED ID 6 | TCTCTTGGATCTTGCTCATGCCCC |
| | IC Target | SED ID 7 | TTTCACCAGCTGTATTAGAAGTAAGCTT GTAATGGACCTCCCGGTGGAACACGGT TTACTTCTAGATAATCTCTTGGATCTTG CTCATGCCCCATTCACTCATACATCCAC TTTTGCAAAAGGCTGGAGTGTCCCAAG TTTGGTGAAGTTTTTAACACCTACCTCG GGTCTCCAAGGATACTGGGATCCATAT CCAATCGATATCAAAGATAATGTTCAG GGAAC |
| Bglobin | Amplification primer | SED ID 8 | GAAGAGCCAAGGACAGGTAC |
| | Amplification primer | SED ID 9 | CAACTTCATCCACGTTCACC |
| | Detection Taqman probe FAM-BHQ | SED ID 10 | CATCACTTAGACCTCACCCTGTGGAG |
| UTI/*E. coli* | Amplification primer | SED ID 11 | GTGGGAAGCGAAAATCCTG |
| | Amplification primer | SED ID 12 | CCAGTACAGGTAGACTTCTG |
| | Detection Taqman-LNA probe FAM-BHQ | SED ID 13 | CTTCTTcacCAAcTTTgATG |
| | IC Amplification primer | SED ID 14 | GTGGGAAGCGAAAATCCTG |
| | IC Amplification primer | SED ID 15 | CCAGTACAGGTAGACTTCTG |
| | IC Detection Taqman probe Cal Red-BHQ | SED ID 16 | TCTCTTGGATCTTGCTCATGCCCC |
| | IC Target | SED ID 17 | GGGAAGCGAAAATCCTGCTTCTTTACA GCCTCCATCAGGGTTTTTAATTCATGCT GAGCTTGTAATGGACCTCCCGGTGGAA CACGGTTTACTTCTAGATAATCTCTTGG ATCTTGCTCATGCCCCATTCACTCATAC ATCCACTTTTGCAAAAGGCTGGAGTGT CCCAAGTTTGGTGAAGTTTTTAACACCT ACCTCGGGTCTCCAAGGATACTGGGAT CCATATCCAATCGATATGGAATTTAAA CCACCGTGTATTGTTTTATCGACAATCG GGATATCAAAACCCGGGAAACTAGAAG GCAAAAGCACACAGCAGTGAGCAACA CATCTTCATCAACTCCAGAAGTCTACCT GTACT |

TABLE 15-continued

List of selected amplification primers and detection probes for the different assays

| Assay combination | Oligonucleotide type | SEQ ID | Sequence[a] |
|---|---|---|---|
| MRSA | Amplification primer | SED ID 14 | GGATCAAACGGCCTGCACA |
| | Amplification primer | SED ID 15 | GTCAAAAATCATGAACCTCATTACTTATG |
| | Amplification primer | SED ID 16 | ATTTCATATATGTAATTCCTCCACATCTC |
| | Amplification primer | SED ID 17 | CAAATATTATCTCGTAATTTACCTTGTTC |
| | Amplification primer | SED ID 18 | CTCTGCTTTATATTATAAAATTACGGCTG |
| | Amplification primer | SED ID 19 | CACTTTTTATTCTTCAAAGATTTGAGC |
| | Detection Taqman probe FAM-BHQ | SED ID 20 | CGTCTTACAACGCAGTAACTACGCACT ATCATTCAGC |
| | IC Amplification primer | SED ID 21 | CAAATATTATCTCGTAATTTACCTTGTTC |
| | IC Amplification primer | SED ID 22 | CTCTGCTTTATATTATAAAATTACGGCTG |
| | IC Detection Taqman probe Cal Red-BHQ | SED ID 23 | ATGCCTCTTCACATTGCTCCACCTTTCC TGTG |
| | IC Target | SED ID 24 | TCTCGTAATTTACCTTGTTCGAAGGTCG GTACAAACAGTCACCGGAGTAGAGATG TTGAAATTGCAGGCAAATTGATTGATTT CACCAGCTGTATTAGAAGTACAAGAAG GTTGGTTACAACCCAAAGACAGCTGTG CATGAATTGCAGAAAATTTATTGCAGC TTCGCCACAGGAAAGGTGGAGCAATGT GAAGAGGCATCATGCCATCTGCTGTAG GCTATCAACCAATGGTAAGACTCTTCT GGAAGCAATTGAGCTATGGTCATGCCA GGTGACAACATATGATGAGTCATCAGC CGTAATTTTATAATATAAAGCAGAG |

[a]Lower case in Taqman-LNA probe indicates Locked nucleic acids (LNA ™).

TABLE 16

Summary of the details of the fluidic centripetal device structures

| Fluidic Layer | Material: Clear polycarbonate (Lexan HP1-112) Fabrication process: Injection molded |
| Thin bottom layer | Polycarbonate (thickness = 0.015") (McMaster Carr #85585K14) |
| Pressure sensitive adhesives | 9795R, 3M ™, in contact with fluidic layer. 467 MP, 3M ™, in contact with bottom layer and 9795R layer |
| Translocatable member | Magnetic Stainless Steel Tumble Stir Elements V&P Scientific, Inc. #721-F (diameter = 4 mm, thickness = 0.5 mm) |
| Lysis chamber (Bottom-fillable chamber) reagents | Slurry of glass beads Sigma #G1145 (150-212 microns) in 0.5% PVP aqueous solution |
| PCR reagents, dried in cuvettes, per reaction | Primers and probes for the different assays as listed in Table 15 at concentrations ranging from 0.2-1.0 µM depending on the assay. Internal controls when present in the multiplex assay were at 500 copies per cuvette BSA, 2.15 mg/ml 1.15 Units polymerase, HGS Diamond Taq (Eurogentec) Trehalose, 6% |
| Liquid container | Polyallomer Tubes, 5 × 20 mm Beckman Coulter #34263 Hot glue Arrow BAP 5-4 Paraffin wax (Calwax ® #CAL-140) 120 µL PCR diluent liquid (3.5 mM MgCl$_2$ in HGS PCR buffer 1X) |
| Waste chamber | Paraffin wax (Calwax ® #CAL-120) |

The fluidic centripetal devices used for the purpose of this example have the external shape described in FIG. 1C and are composed of the fluidic elements shown and described in FIG. 17.

The fluidic centripetal devices used for the purpose of this example contained the components listed in Table 16.

The liquid container was fabricated using the following protocol: load 120 µl of PCR diluent liquid; seal the polyallomer tube with Hot glue Arrow BAP 5-4.

The fluidic centripetal device was assembled using the following protocol: place paramagnetic disc in the lysis chamber; load 60 µl of glass beads slurry; load 4.6 µl of PCR reagents in each cuvette; dry the slurry and the PCR reagents under heat and vacuum; place the liquid container in the retention chamber; dispense Low Melting Paraffin wax in the waste chamber.

Bind the pre-assembled layers 9795R/467 MP/polycarbonate to the fluidic layer and apply a pressure using a press with a torque of 90 in·lbs.

Experiment

A cheek brushing swab was collected from a human volunteer using Medical Packaging swab with snap valve technology filled with 600 µl of Tris EDTA 10 mM (TE). The swab was placed in contact with the inside surface of the cheek and swirled for 30 s. The swab was placed back into its sleeve and the snap valve was broken to release the 600 µl of TE. After 5 minutes wait time, the swab is vortexed for 1 minute. This suspended diluted sample served for testing.

Urine samples collected from patients were diluted 1/56 in TE. This diluted sample served for testing.

During a clinical study, nose swabs were collected from volunteers and resuspended in 600 µl of TE. This suspended diluted sample served for testing.

A volume of 140 µl of the diluted samples is placed directly into the sample intake receptacle of the fluidic centripetal device described above.

The fluidic centripetal devices are placed into the instrument and the protocols were performed according to Tables 9, 10, 11, 12, and 13.

In some tests, the protocol was paused and resumed at step 8 to examine the position of the fluid in the retention chamber receptacle.

Thermocycling was performed either under conditions listed in Table 17 or Table 18, depending on the assay.

TABLE 17

Thermocycling conditions for beta-globin assay

| Cycle | Cycle point | |
|---|---|---|
| Hold | @ 94° C., 3 min | |
| Cycling (45) | | Step1 @ 95° C., hold 5 s |
| | | Step2 @ 55° C., hold 15 s |
| | | Step3 @ 72° C., hold 20 s |

TABLE 18

Thermocycling conditions for UTI and MRSA assays

| Cycle | Cycle point | |
|---|---|---|
| Hold | @99° C., 12 min | |
| Cycling (45) | | Step1 @ 95° C., hold 20 s |
| | | Step2 @ 61° C., hold 40 s |
| | | Step3 @ 72° C., hold 40 s |

Results:

Internal controls revealed no or only minimal inhibition by samples. All samples already known to contain the target DNA by another test method were indeed found positive with the fluidic centripetal device and similarly, samples already known to be negative for the target DNA were indeed found negative with the fluidic centripetal device.

This example illustrates the versatility of the fluidic centripetal technology of this invention for detecting nucleic acids from a variety of biological samples and cells. Diluted fecal samples were also successfully tested for the detection of bacterial pathogens responsible for diarrhea.

Example 4

The following example is illustrative and is not intended to be limiting.

The present example concerns the use of an example embodiment of the fluidic centripetal device and more specifically of the bottom-fillable chamber and other elements of this invention to concentrate cells and microbes.

TABLE 19

Summary of the details of the fluidic centripetal device structures.

| Fluidic Layer | Material: Clear polycarbonate (Lexan HP1-112) Fabrication process: Injection molded |
|---|---|
| Thin bottom layer | Polycarbonate (thickness = 0.015") (McMaster Carr #85585K14) |
| Pressure sensitive adhesives | 9795R, 3M ™, in contact with fluidic layer 467 MP, 3M ™, in contact with bottom layer and 9795R layer |
| Translocatable member | Magnetic Stainless Steel Tumble Stir Elements V&P Scientific, Inc. #721-F (diameter = 4 mm, thickness = 0.5 mm) |
| Lysis chamber (Bottom-fillable chamber) reagents | Slurry of glass beads Sigma #G1145 (150-212 microns) in 0.5% PVP aqueous solution |

The fluidic centripetal devices used for the purpose of this example have the external shape described in FIG. 1C and are composed of the fluidic elements shown and described in FIG. 17.

The fluidic centripetal devices used for the purpose of this example contained the components listed in Table 19.

The fluidic centripetal device was assembled using the following protocol: place paramagnetic disc in the lysis chamber; load 60 µl of glass beads slurry; dry the slurry overnight under vacuum; bind the pre-assembled layers 9795R/467 MP/polycarbonate to the fluidic layer and apply a pressure using a press with a torque of 90 in·lbs.

Experiment

10 µl ($10^5$ Colony Forming Units; CFU) of a diluted culture of the bacteria *Enterococcus faecalis* were mixed with 190 µl of TE.

The 200 µl mixture was placed directly into the sample intake receptacle of the fluidic centripetal device described above.

The fluidic centripetal devices were placed into the instrument and the following protocols were performed according to Tables 9 and 10.

The fluidic centripetal device were disassembled by removing the pressure sensitive layers so that the liquid in the bottom-fillable chamber and in the overflow chamber could be harvested and diluted to perform plate counts of the bacterial cells present in each chambers.

Results:

Plate counts revealed that the number of bacterial cells was superior in the bottom-fillable chamber compared to number of bacterial cells present in the overflow chamber by a factor of 1.5 to 3 times.

The embodiments described above are intended to be exemplary only. The scope of the invention is therefore intended to be limited solely by the appended claims.

We claim:

1. A fluidic centripetal device for testing components of a biological material in a fluid, said fluidic centripetal device having a shape adapted to be received within a rotatable holder, said rotatable holder having a center of rotation and an outer edge, said fluidic centripetal device extending radially between said center of rotation and said outer edge, an inner side of said fluidic centripetal device being located towards said center of rotation and an outer side of said fluidic centripetal device being located towards said outer edge, the device comprising:
   a fluidic component layer having fluidic features on at least a front face, said fluidic features including:
      a retention chamber for receiving said fluid, said retention chamber being coupled to a fluid entry channel for receiving said fluid into said retention chamber; and
      a container wholly provided in said retention chamber, said container containing a liquid diluent, said container further comprising a first phase-change material for releasing said diluent inside the retention chamber; and
   a bottom component layer bonded to said fluidic component layer, the fluidic component layer and the bottom component layer creating a fluidic network, said fluid flowing through said fluidic network under centripetal force.

2. The device as claimed in claim 1, wherein said retention chamber comprises a flow decoupling receptacle, wherein said flow decoupling receptacle is located at an outer side of said retention chamber between the fluid entry channel and an interior of the retention chamber, said flow decoupling receptacle interrupting a fluidic connection between the fluid entry channel and the retention chamber.

3. The device of claim 2, wherein said flow decoupling receptacle includes a dried reagent.

4. The device of claim 1, wherein said retention chamber has a distribution outlet for said retention chamber, said distribution outlet being located at an outer side of said retention chamber, said distribution outlet being coupled to a distribution channel at an inner side of said distribution channel at a first transversal end of said distribution channel, said distribution channel having at least one cuvette provided at an outer side of said distribution channel.

5. The device as claimed in claim 4, wherein said at least one cuvette includes at least one of a dried reagent and a second phase-change material.

6. The device as claimed in claim 4, wherein said cuvette is adapted to be optically queried for at least one parameter, wherein said parameter is one of fluorescence, absorbance, and colorimetry.

7. The device as claimed in claim 4, wherein said distribution channel includes a waste chamber at a second end of said distribution channel.

8. The device as claimed in claim 7, wherein said waste chamber includes a third phase-change material.

9. The device as claimed in claim 8, wherein said distribution channel, said at least one cuvette and said waste chamber are provided on a portion of said fluidic component layer which extends beyond said outer edge of said rotatable holder.

10. The device of claim 9, wherein said fluidic component layer comprises at least two distinct temperature-controllable sections.

11. The device of claim 1, wherein said container is adapted to maintain said liquid diluent in said container and to release said liquid diluent in said retention chamber upon application of an external force to said container, wherein said external force is one of mechanical, electrical, electromagnetic, heat, shock and acoustic force, thereby allowing a fluidic connection between said liquid diluent and said fluid in said retention chamber.

12. The device of claim 1, said device further comprising a bottom-fillable chamber, wherein said bottom-fillable chamber is coupled to said entry channel for providing fluid to the retention chamber.

13. The device of claim 12, wherein said bottom-fillable chamber includes at least one translocatable member that translocates within said bottom-fillable chamber in response to an external fluctuating magnetic field.

14. The device of claim 12, wherein the bottom-fillable chamber comprises at least one object irresponsive to a fluctuating magnetic field and wherein said object is at least one of a bead, a zeolite, a particle, a filtration particle, a glass bead, a zirconium bead, a resin, a bead and resin slurry.

15. The device of claim 14, wherein at least one of said object and said translocatable member is coated with at least one of a chelating and a ligand material adapted to interact with components of said fluid.

16. The device of claim 12, further comprising an overflow chamber coupled to a surplus outlet for said bottom-fillable chamber, said surplus outlet allowing exit of part of said fluid from said bottom-fillable chamber to said overflow chamber, wherein said surplus outlet is provided near said inner side of said bottom-fillable chamber on a longitudinal side of said bottom-fillable chamber.

17. The device of claim 16, further comprising an exit outlet for said bottom-fillable chamber, said exit outlet allowing exit of said fluid from said bottom-fillable chamber, wherein said exit outlet is located on said one longitudinal side of said bottom-fillable chamber, said exit outlet being located closer to said outer side of said bottom-fillable chamber than said surplus outlet, a metering volume of said bottom-fillable chamber being defined between said exit outlet and said surplus outlet.

18. The device of claim 17, further comprising a burst valve at said exit outlet, said burst valve opening at a predetermined centripetal force applied on said apparatus, said burst valve preventing said fluid from exiting said bottom-fillable chamber until said opening.

19. The device of claim 17, wherein said retention chamber is coupled to said exit outlet at an inner side of said retention chamber, said retention chamber being located closer to said outer side of said fluidic component layer than said bottom-fillable chamber, wherein said retention chamber is coupled to said exit outlet via a metering channel, said metering channel for circulating at least a portion of said fluid from said bottom-fillable chamber to said retention chamber.

20. The device of claim 16, further comprising an exit outlet for said bottom-fillable chamber, said exit outlet allowing exit of said fluid from said bottom-fillable chamber, wherein said exit outlet is located on one longitudinal side of said bottom-fillable chamber.

21. The device as claimed in claim 1, further comprising an intake receptacle for loading fluid comprising said biological material.

22. The device of claim 1, wherein said phase-change material is a heat tolerant material releasing said diluent at a certain temperature.

23. The device of claim 1, wherein said retention chamber comprises a flow decoupling receptacle located at an outer side of said retention chamber, the flow decoupling receptacle comprising a reagent.

24. The device of claim 23, wherein the reagent is isolated from an inside of the retention chamber by a fourth phase-change material that is a heat tolerant material releasing said reagent at a certain temperature.

25. A test apparatus using a fluidic centripetal device for testing components of a biological material in a fluid, the apparatus comprising:
at least one of said fluidic centripetal device as claim in claim 1;
a rotor assembly;
a holder for receiving said at least one of said fluidic centripetal device using said fluidic component layer, said holder being coupled to said rotor;
a motor for rotating said rotor assembly;
a speed controller for said motor for controlling at least one of a duration and a speed of rotation of said rotor assembly;
a temperature conditioning sub-system for controlling a temperature of at least a portion of said fluidic centripetal device;
a detection sub-system for detecting a characteristic of said fluid; and
a user interface for receiving a user command and for sending a command to at least one of said speed controller, said temperature conditioning sub-system, said excitation sub-system, and said detection sub-system.

26. The test apparatus as claimed in claim 25, wherein said temperature conditioning sub-system controls a temperature of at least two zones of said fluidic centripetal device.

27. A testing method using a fluidic centripetal device for testing components of a biological material in a fluid, the method comprising:
providing a test apparatus with at least one of said fluidic centripetal device as claimed in claim 25;
providing a fluid with biological material;
loading said fluid in said intake receptacle of said fluidic centripetal device;
placing said fluidic centripetal device in said holder of said test apparatus;
providing a user command to commence a test sequence;

rotating said rotor assembly for flowing said fluid though said fluidic network.

28. The testing method of claim 27, wherein the fluid is selected from the group consisting of blood, nasal pharyngeal aspiration, oral fluid, liquid from resuspended oral swab, liquid from resuspended nasal swab, liquid resuspended from anal swab, liquid resuspended from vaginal swab, saliva and urine.

29. The testing method of claim 27 for testing at least one component selected from the group consisting of ions, sugars, metabolites, fatty acids, amino acids, nucleic acids, proteins and lipids.

\* \* \* \* \*

SEQUENCE LISTING

```
<160> NUMBER OF SEQ ID NOS: 24

<210> SEQ ID NO 1
<211> LENGTH: 23
<212> TYPE: DNA
<213> ORGANISM: Artificial Sequence
<220> FEATURE:
<223> OTHER INFORMATION: Synthetic

<400> SEQUENCE: 1
tttcaccagc tgtattagaa gta                                          23

<210> SEQ ID NO 2
<211> LENGTH: 23
<212> TYPE: DNA
```

<213> ORGANISM: Artificial Sequence
<220> FEATURE:
<223> OTHER INFORMATION: Synthetic

<400> SEQUENCE: 2
gttccctgaa cattatcttt gat                                              23

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
cccagcaaat ggctcaaaag c                                                21

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
tttcaccagc tgtattagaa gta                                              23

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
gttccctgaa cattatcttt gat                                              23

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
tctcttggat cttgctcatg cccc                                             24

<210> SEQ ID NO 7
<211> LENGTH: 225
<212> TYPE: DNA
<213> ORGANISM: Artificial Sequence
<220> FEATURE:
<223> OTHER INFORMATION: Synthetic

<400> SEQUENCE: 7
tttcaccagc tgtattagaa gtaagcttgt aatggacctc ccggtggaac acggtttact      60
tctagataat ctcttggatc ttgctcatgc cccattcact catacatcca cttttgcaaa     120
aggctggagt gtcccaagtt tggtgaagtt tttaacacct acctcgggtc tccaaggata     180
ctgggatcca tatccaatcg atatcaaaga taatgttcag ggaac                     225

<210> SEQ ID NO 8
<211> LENGTH: 20
<212> TYPE: DNA
<213> ORGANISM: Artificial Sequence

```
<220> FEATURE:
<223> OTHER INFORMATION: Synthetic

<400> SEQUENCE: 8
gaagagccaa ggacaggtac                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
caacttcatc cacgttcacc                                               20

<210> SEQ ID NO 10
<211> LENGTH: 26
<212> TYPE: DNA
<213> ORGANISM: Artificial Sequence
<220> FEATURE:
<223> OTHER INFORMATION: Synthetic

<400> SEQUENCE: 10
catcacttag acctcaccct gtggag                                        26

<210> SEQ ID NO 11
<211> LENGTH: 19
<212> TYPE: DNA
<213> ORGANISM: Artificial Sequence
<220> FEATURE:
<223> OTHER INFORMATION: Synthetic

<400> SEQUENCE: 11
gtgggaagcg aaaatcctg                                                19

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
ccagtacagg tagacttctg                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
cttcttcacc aactttgatg                                               20

<210> SEQ ID NO 14
<211> LENGTH: 19
<212> TYPE: DNA
<213> ORGANISM: Artificial Sequence
<220> FEATURE:
<223> OTHER INFORMATION: Synthetic

<400> SEQUENCE: 14
gtgggaagcg aaaatcctg                                                19
```

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
ccagtacagg tagacttctg                                              20

<210> SEQ ID NO 16
<211> LENGTH: 24
<212> TYPE: DNA
<213> ORGANISM: Artificial Sequence
<220> FEATURE:
<223> OTHER INFORMATION: Synthetic

<400> SEQUENCE: 16
tctcttggat cttgctcatg cccc                                         24

<210> SEQ ID NO 17
<211> LENGTH: 361
<212> TYPE: DNA
<213> ORGANISM: Artificial Sequence
<220> FEATURE:
<223> OTHER INFORMATION: Synthetic

<400> SEQUENCE: 17
gggaagcgaa aatcctgctt ctttacagcc tccatcaggg tttttaattc atgctgagct    60
tgtaatggac ctcccggtgg aacacggttt acttctagat aatctcttgg atcttgctca   120
tgccccattc actcatacat ccactttgc aaaaggctgg agtgtcccaa gtttggtgaa    180
gtttttaaca cctacctcgg gtctccaagg atactgggat ccatatccaa tcgatatgga   240
atttaaacca ccgtgtattg ttttatcgac aatcgggata tcaaaacccg ggaaactaga   300
aggcaaaagc acacagcagt gagcaacaca tcttcatcaa ctccagaagt ctacctgtac   360
t                                                                  361

<210> SEQ ID NO 18
<211> LENGTH: 19
<212> TYPE: DNA
<213> ORGANISM: Artificial Sequence
<220> FEATURE:
<223> OTHER INFORMATION: Synthetic

<400> SEQUENCE: 18
ggatcaaacg gcctgcaca                                               19

<210> SEQ ID NO 19
<211> LENGTH: 29
<212> TYPE: DNA
<213> ORGANISM: Artificial Sequence
<220> FEATURE:
<223> OTHER INFORMATION: Synthetic

<400> SEQUENCE: 19
gtcaaaaatc atgaacctca ttacttatg                                    29

<210> SEQ ID NO 20
<211> LENGTH: 29
<212> TYPE: DNA
<213> ORGANISM: Artificial Sequence
<220> FEATURE:
<223> OTHER INFORMATION: Synthetic

```
<400> SEQUENCE: 20
atttcatata tgtaattcct ccacatctc                                              29

<210> SEQ ID NO 21
<211> LENGTH: 29
<212> TYPE: DNA
<213> ORGANISM: Artificial Sequence
<220> FEATURE:
<223> OTHER INFORMATION: Synthetic

<400> SEQUENCE: 21
caaatattat ctcgtaattt accttgttc                                              29

<210> SEQ ID NO 22
<211> LENGTH: 29
<212> TYPE: DNA
<213> ORGANISM: Artificial Sequence
<220> FEATURE:
<223> OTHER INFORMATION: Synthetic

<400> SEQUENCE: 22
ctctgcttta tattataaaa ttacggctg                                              29

<210> SEQ ID NO 23
<211> LENGTH: 27
<212> TYPE: DNA
<213> ORGANISM: Artificial Sequence
<220> FEATURE:
<223> OTHER INFORMATION: Synthetic

<400> SEQUENCE: 23
cactttttat tcttcaaaga tttgagc                                                27

<210> SEQ ID NO 24
<211> LENGTH: 37
<212> TYPE: DNA
<213> ORGANISM: Artificial Sequence
<220> FEATURE:
<223> OTHER INFORMATION: Synthetic

<400> SEQUENCE: 24
cgtcttacaa cgcagtaact acgcactatc attcagc                                     37
```